(12) United States Patent
Naqvi et al.

(10) Patent No.: US 11,522,705 B2
(45) Date of Patent: Dec. 6, 2022

(54) TESTING AND OTHER DATA COMMUNICATED USING TRUST MODELS IN DECENTRALIZED AND DISTRIBUTED SYSTEMS

(71) Applicant: Safelishare, Inc., Morristown, NJ (US)

(72) Inventors: Shamim A. Naqvi, Morristown, NJ (US); Robert Frank Raucci, New York, NY (US); Goutham Puppala, Basking Ridge, NJ (US)

(73) Assignee: Safelishare, Inc., Morristown, NJ (US)

( * ) Notice: Subject to any disclaimer, the term of this patent is extended or adjusted under 35 U.S.C. 154(b) by 147 days.

(21) Appl. No.: 16/940,702

(22) Filed: Jul. 28, 2020

(65) Prior Publication Data
US 2022/0038284 A1  Feb. 3, 2022

(51) Int. Cl.
*H04L 9/32* (2006.01)
*G06F 21/62* (2013.01)
*G06Q 20/06* (2012.01)
*G16H 40/67* (2018.01)
*H04L 9/08* (2006.01)

(52) U.S. Cl.
CPC ........ *H04L 9/3218* (2013.01); *G06F 21/6245* (2013.01); *G06Q 20/065* (2013.01); *G16H 40/67* (2018.01); *H04L 9/0819* (2013.01)

(58) Field of Classification Search
CPC . H04L 9/3218; H04L 9/0819; G06F 21/6245; G06Q 20/065; G16H 40/67
See application file for complete search history.

(56) References Cited

U.S. PATENT DOCUMENTS

| | | | | |
|---|---|---|---|---|
| 8,280,838 | B2 * | 10/2012 | Ferrucci | G06N 5/04 706/54 |
| 2009/0178138 | A1 * | 7/2009 | Weiss | G06F 21/577 726/22 |
| 2018/0225661 | A1 * | 8/2018 | Russinovich | G06Q 20/3829 |
| 2018/0341930 | A1 * | 11/2018 | Moir | G06Q 20/0655 |
| 2022/0036346 | A1 * | 2/2022 | Naqvi | G06Q 20/381 |

FOREIGN PATENT DOCUMENTS

CN  103136441 A  *  6/2013  .......... A61M 5/1723

* cited by examiner

*Primary Examiner* — Sanchit K Sarker
(74) *Attorney, Agent, or Firm* — Stuart H. Mayer; Mayer & Williams PC

(57) ABSTRACT

A method for communicating information relating to test results of a user includes obtaining test results of a user. An assertion is derived from the test results of the user. The test results are input to a pre-provisioned first algorithm. The assertion is encapsulated in a first data object by a PGE that controls an environment in which the first algorithm is executed. A first proof is generated which is configured to be usable to verify that the first algorithm used the test results to produce the assertion when provided to a PVE along with the first data object. The test results itself are excluded from the first proof and the first data object such that privacy of the test results is maintained. The first proof and the first data object are communicated to a receiving communication device from an enterprise communication device associated with the user and an enterprise.

21 Claims, 45 Drawing Sheets

Transaction from device "A" to device "B".

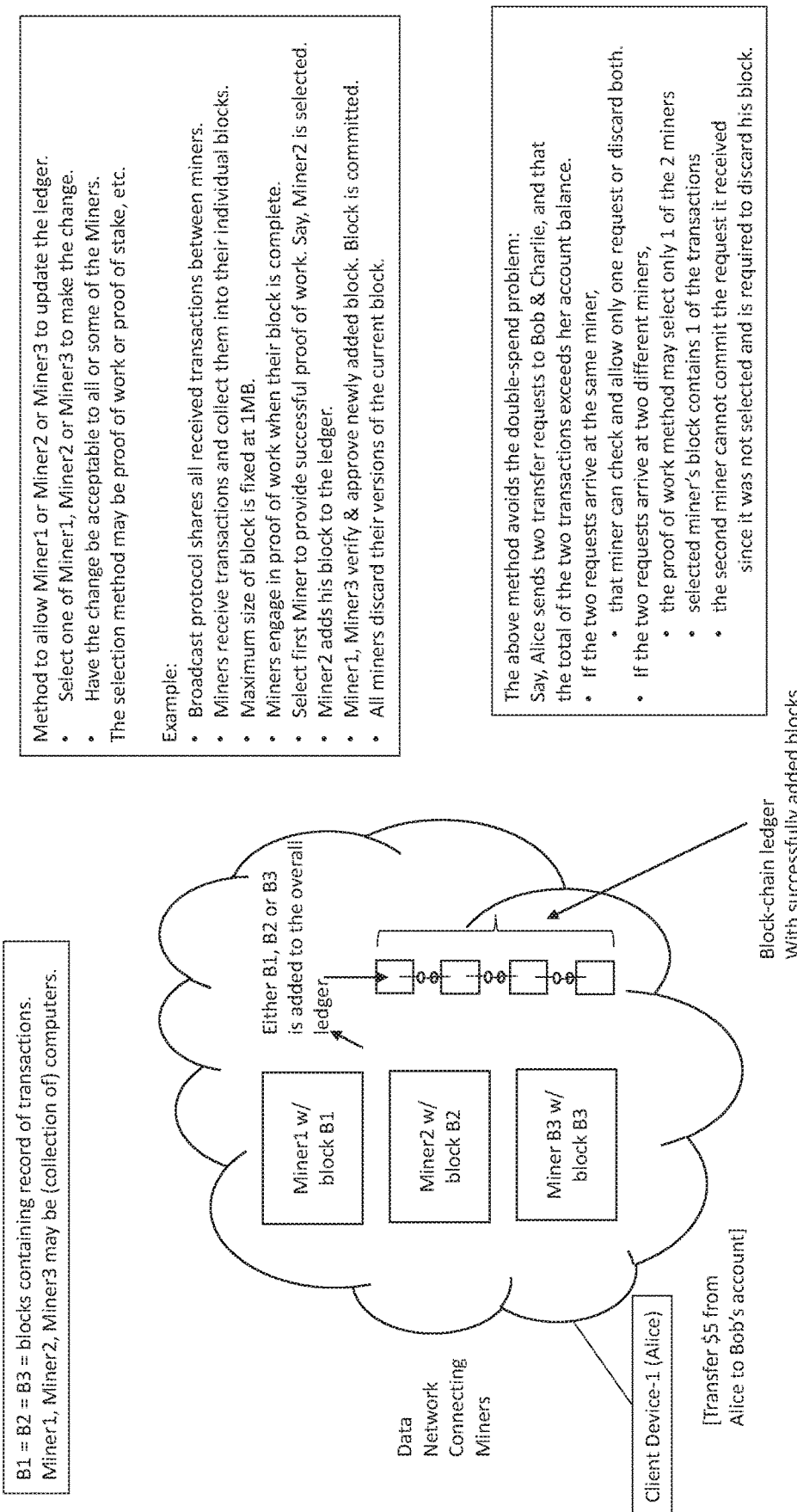
FIG. 1: Bitcoin-style decentralized transaction processing

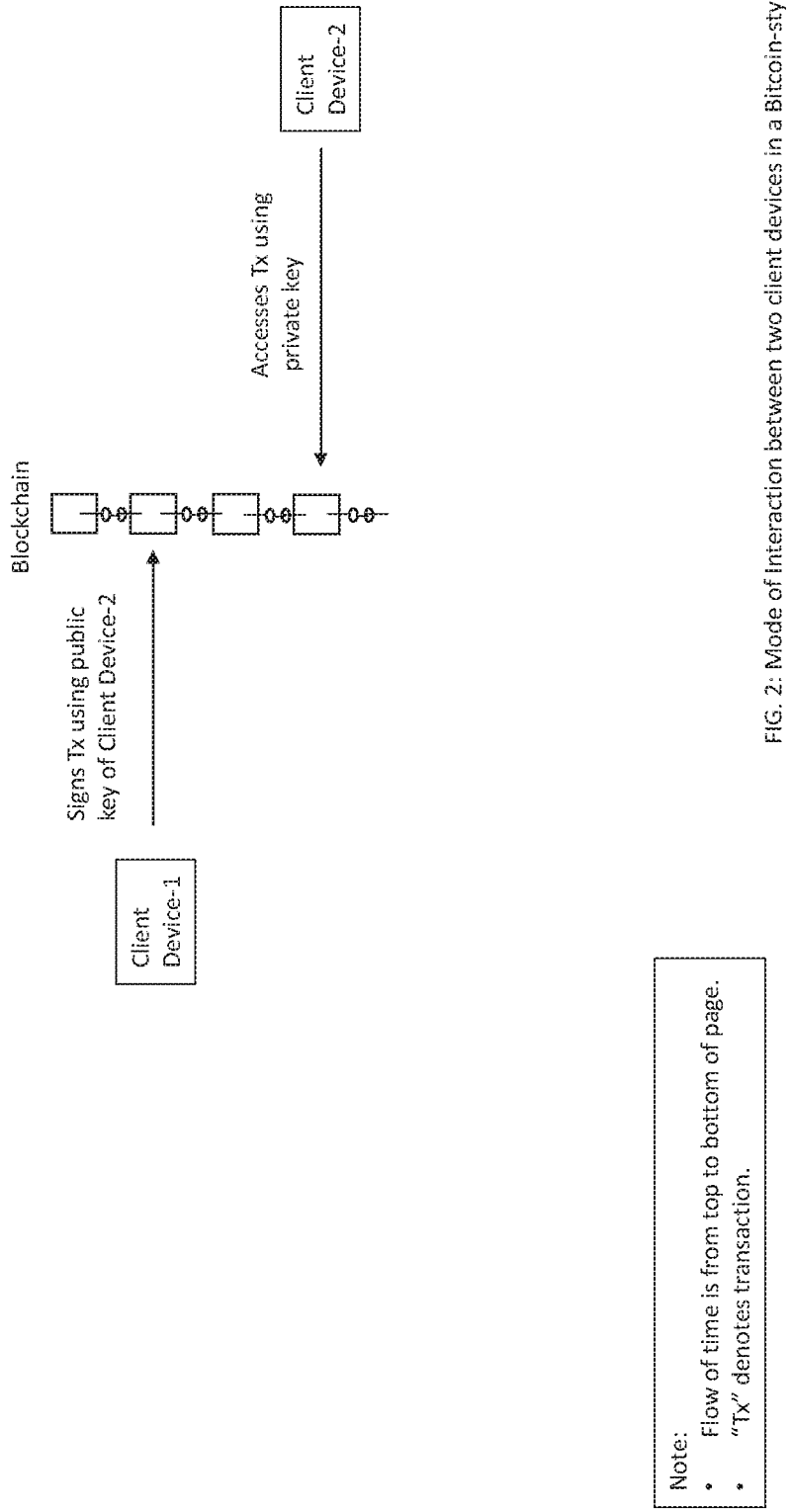
FIG. 2: Mode of interaction between two client devices in a Bitcoin-style network

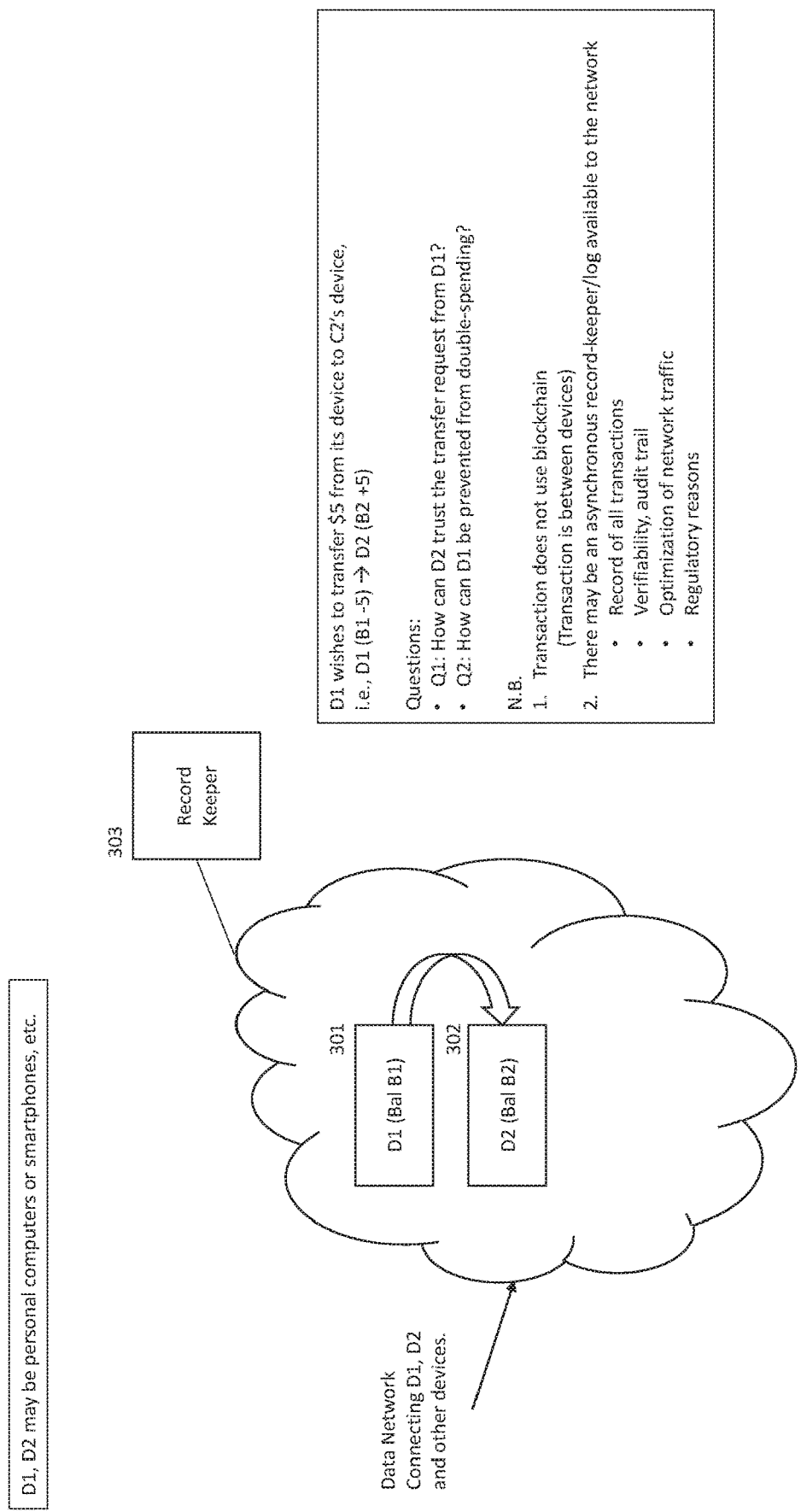
FIG. 3: Decentralized transaction processing without interacting with an overall ledger/blockchain

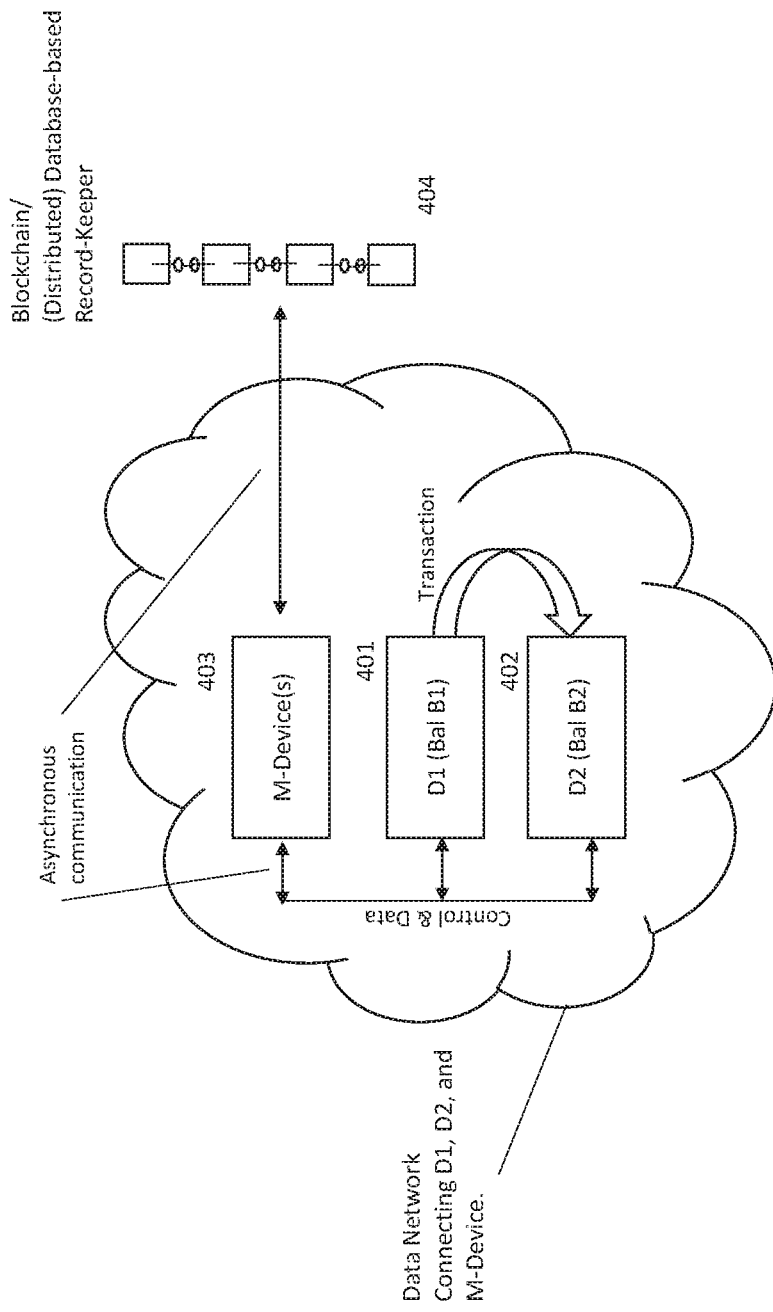
FIG. 4: Decentralized transaction processing with asynchronous updates to blockchain

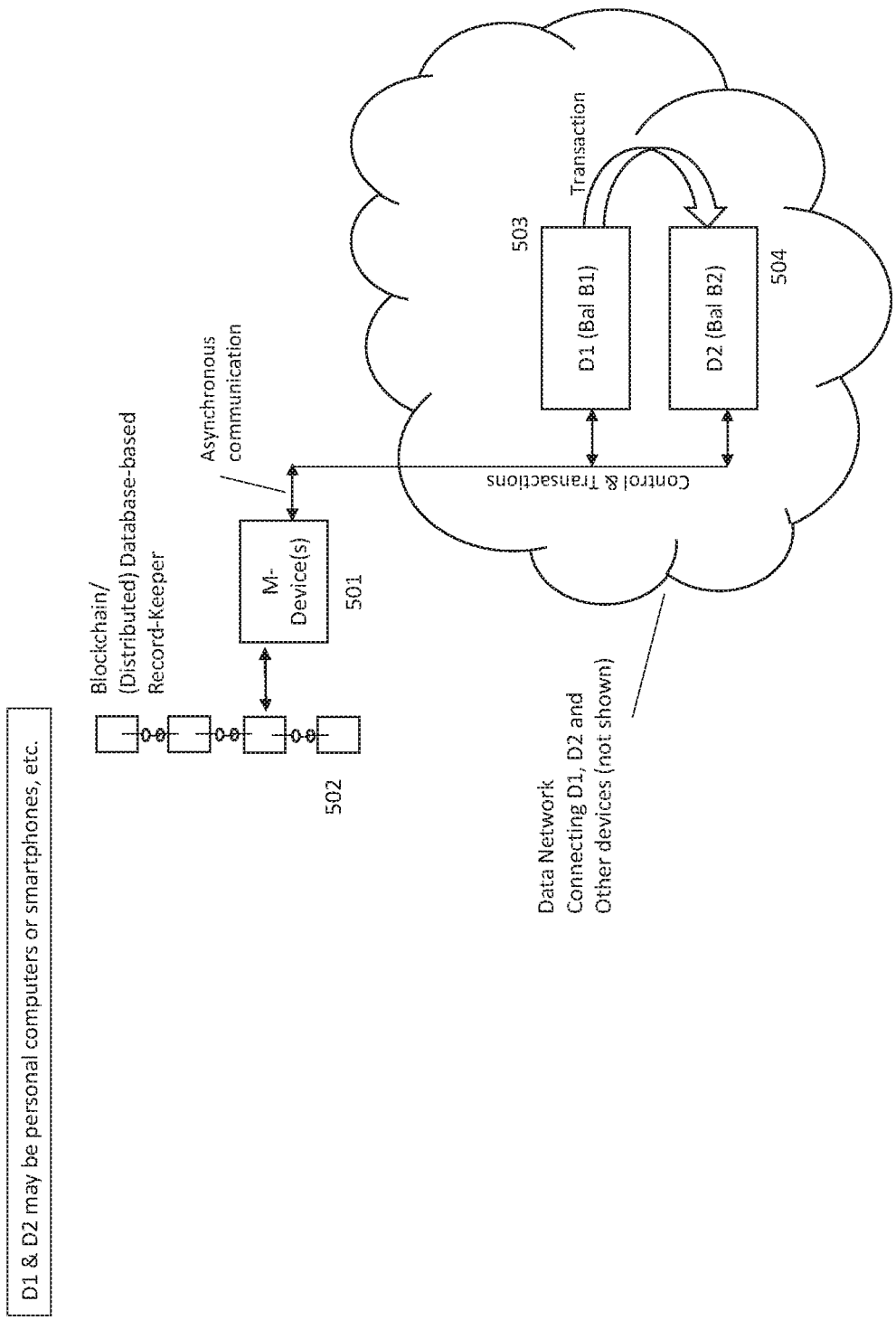
FIG. 5: Alternative Embodiment of Network with M-Device running a computer program on the blockchain

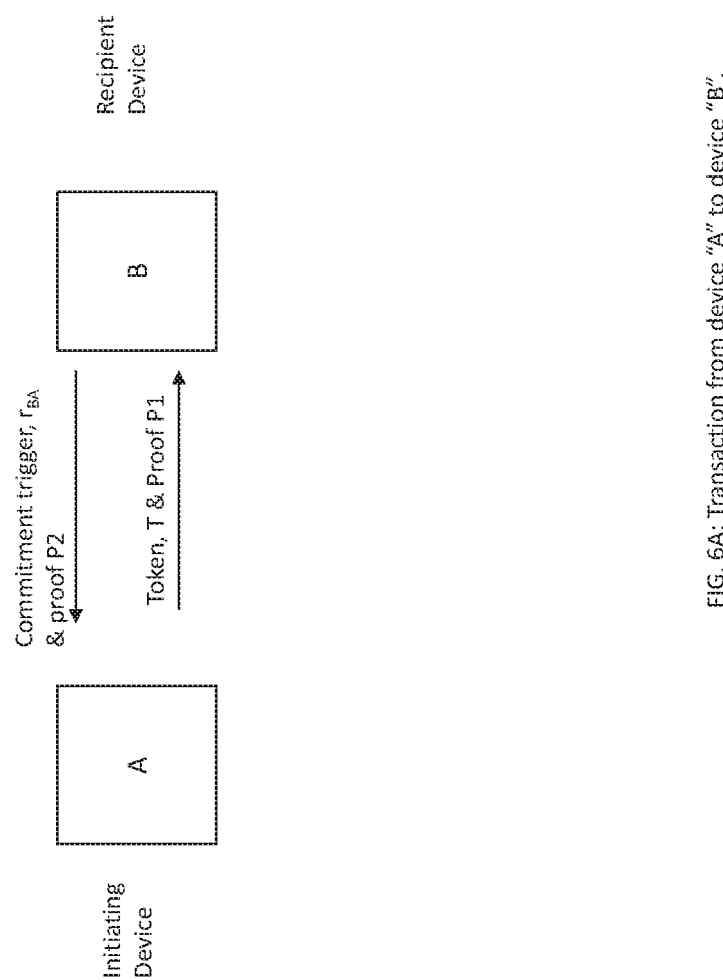
FIG. 6A: Transaction from device "A" to device "B".

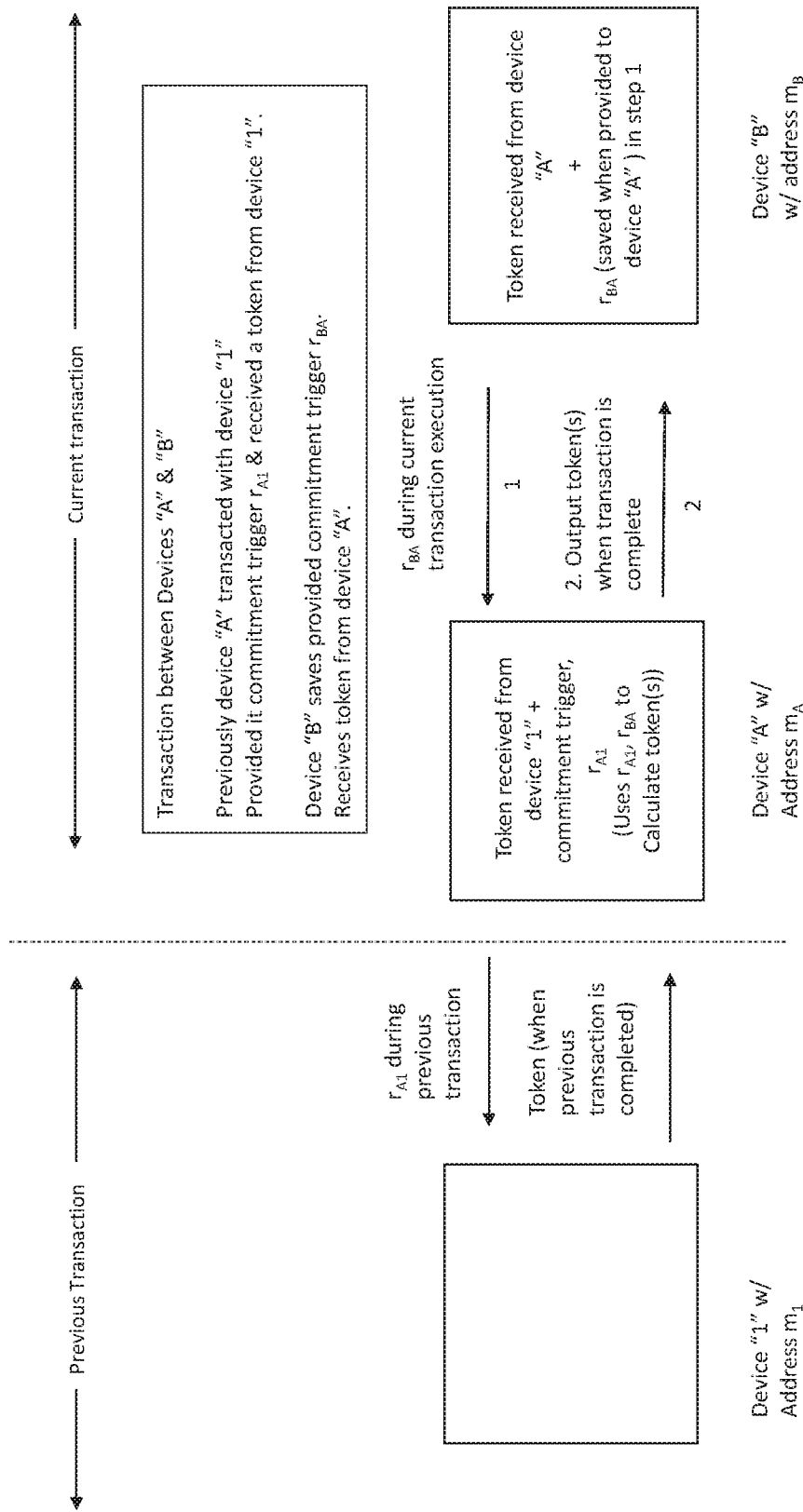
FIG. 6B: Transaction sequence between Device "A" & "2".

701: Commitment Function $F(r, m) = (g^r * h^m) \mod p = C_r$ $F(r_1, m_1) = (g^{r_1} * h^{m_1}) \mod p = C_1$
$F(r_2, m_2) = (g^{r_2} * h^{m_2}) \mod p = C_2$ $C_1 * C_2 = C_{12} = (g^{(r_1 + r_2)} * h^{(m_1+m_2)}) \mod p$ (g, h, p are known primes, $r_1, r_2, m_1, m_2$ are integers)

Calculating $C_1$ without knowing $r_1$ requires solving the discrete log problem. No known efficient solutions.

Given $C_1, C_2$:
Verifying $C_1 * C_2 = C_{12}$ is straight-forward & efficient.

702: Token (= spending right)

| Bal/Amt | $C_{A1} =$ $F(r_{A1}, m_A)$ | $C_{BA} =$ $F(r_{BA}, m_B)$ | $C_{A1,BA} =$ $C_{A1} * C_{BA}$ |

If device "A" is transacting with device "B"
$r_{BA}$ will be generated and provided by device "B" to device "A"
$m_B$ denotes the integer address of device "B"
$r_{A1}$ will have been provided by device "A" to device "1" for a previous transaction
& $m_A$ denotes the integer address of device "A".

Note: Integer "r" in function F(r,m) will be called the commitment trigger.

FIG. 7A: Commitment Calculations & Tokens

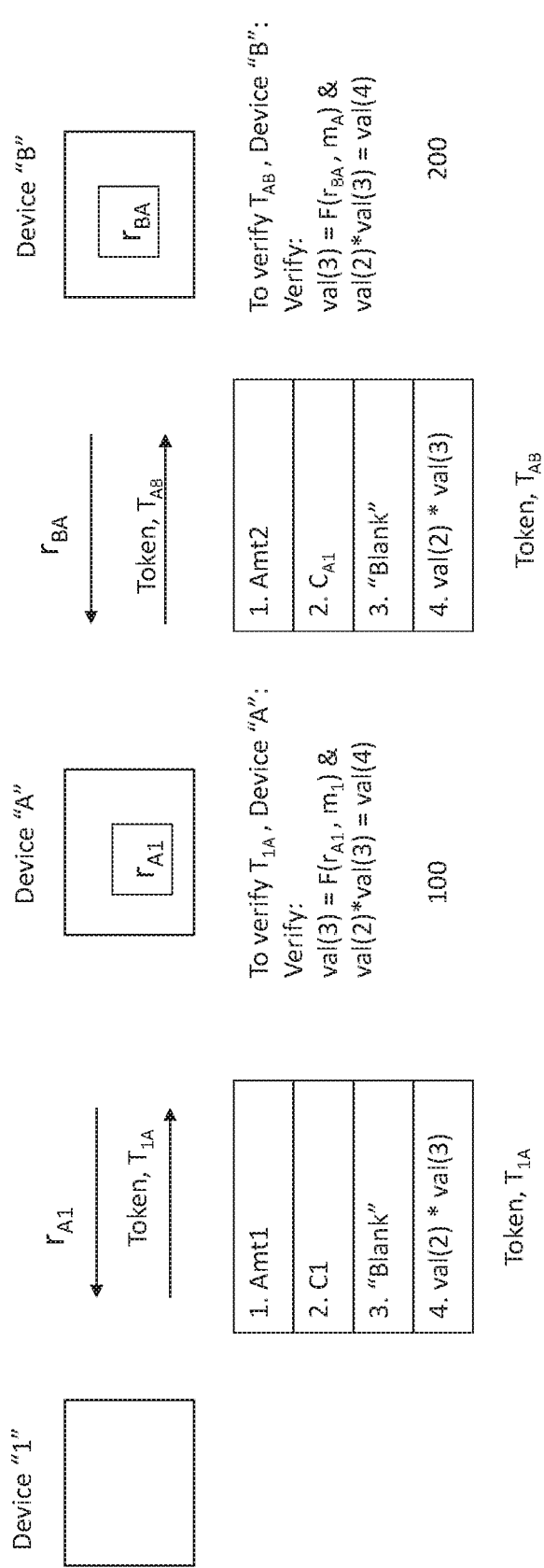
FIG. 7B: Verification of Tokens

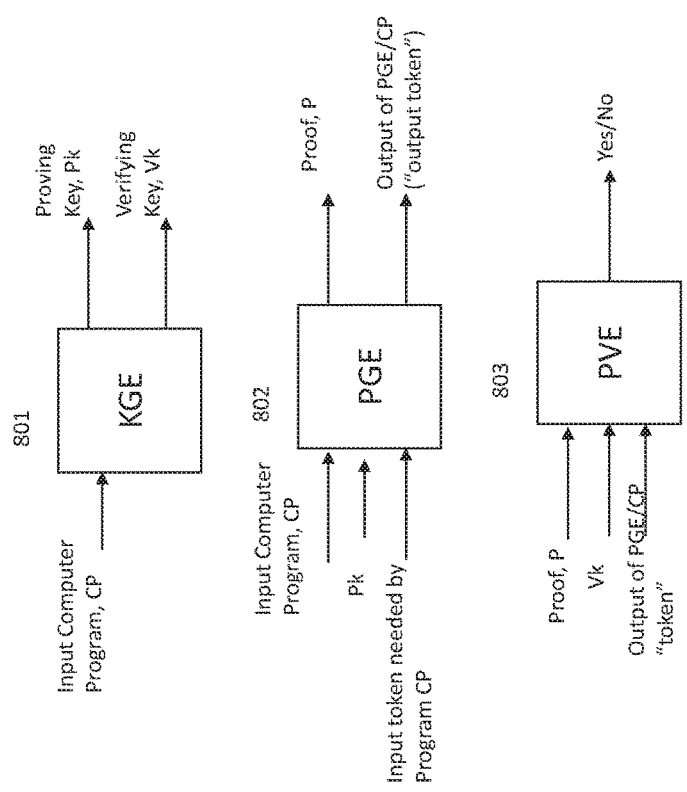
FIG. 8A: Program Proof Technology

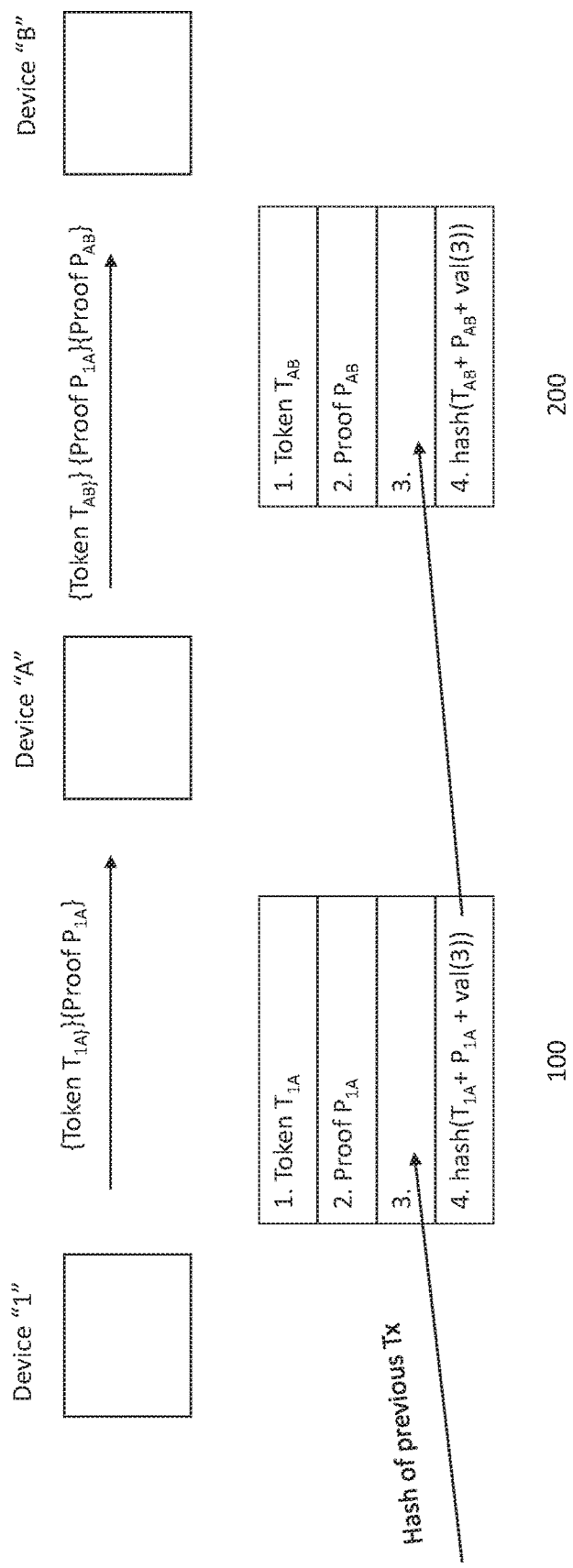
FIG. 8B: Verification of Tokens

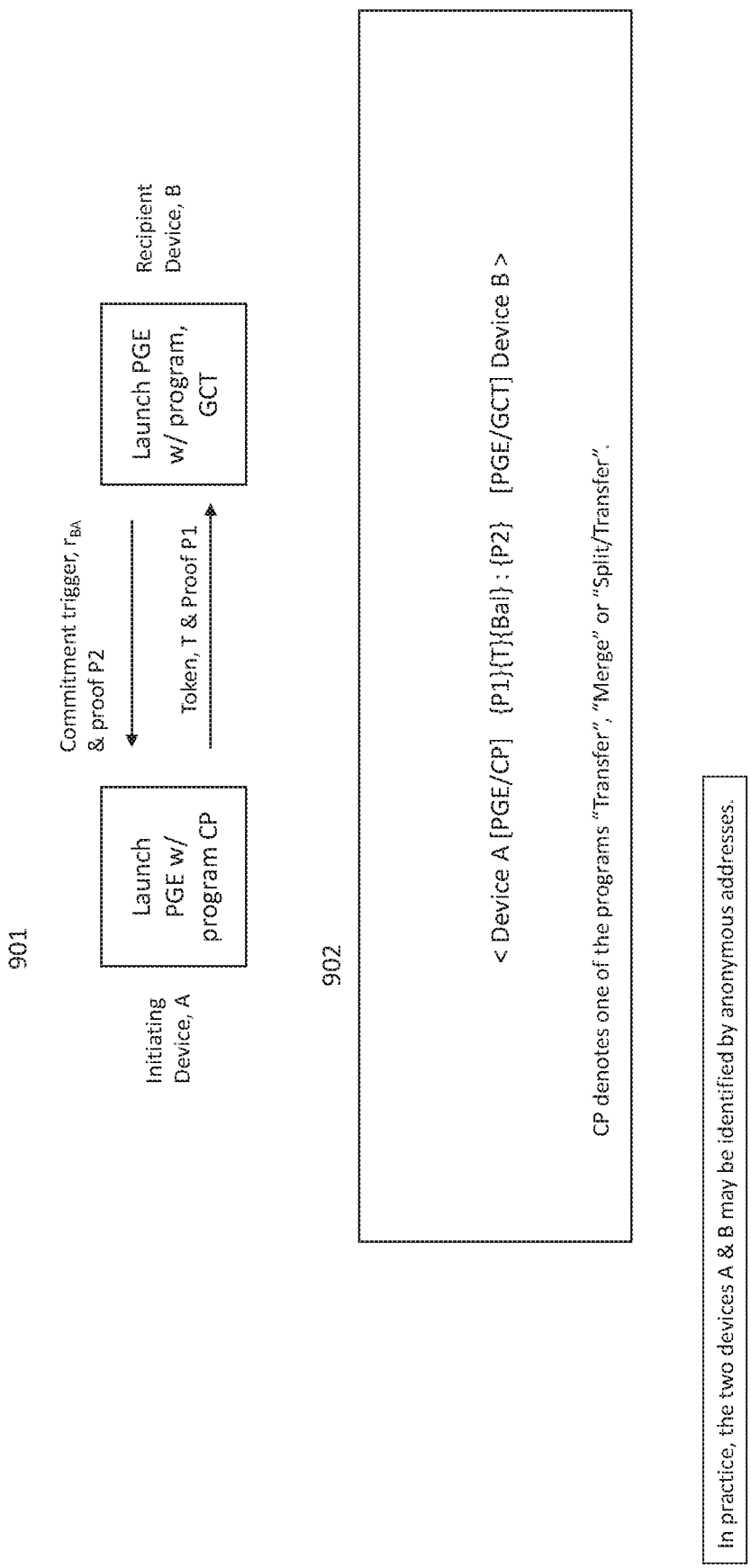
FIG. 9: Transaction from device "A" to "B"

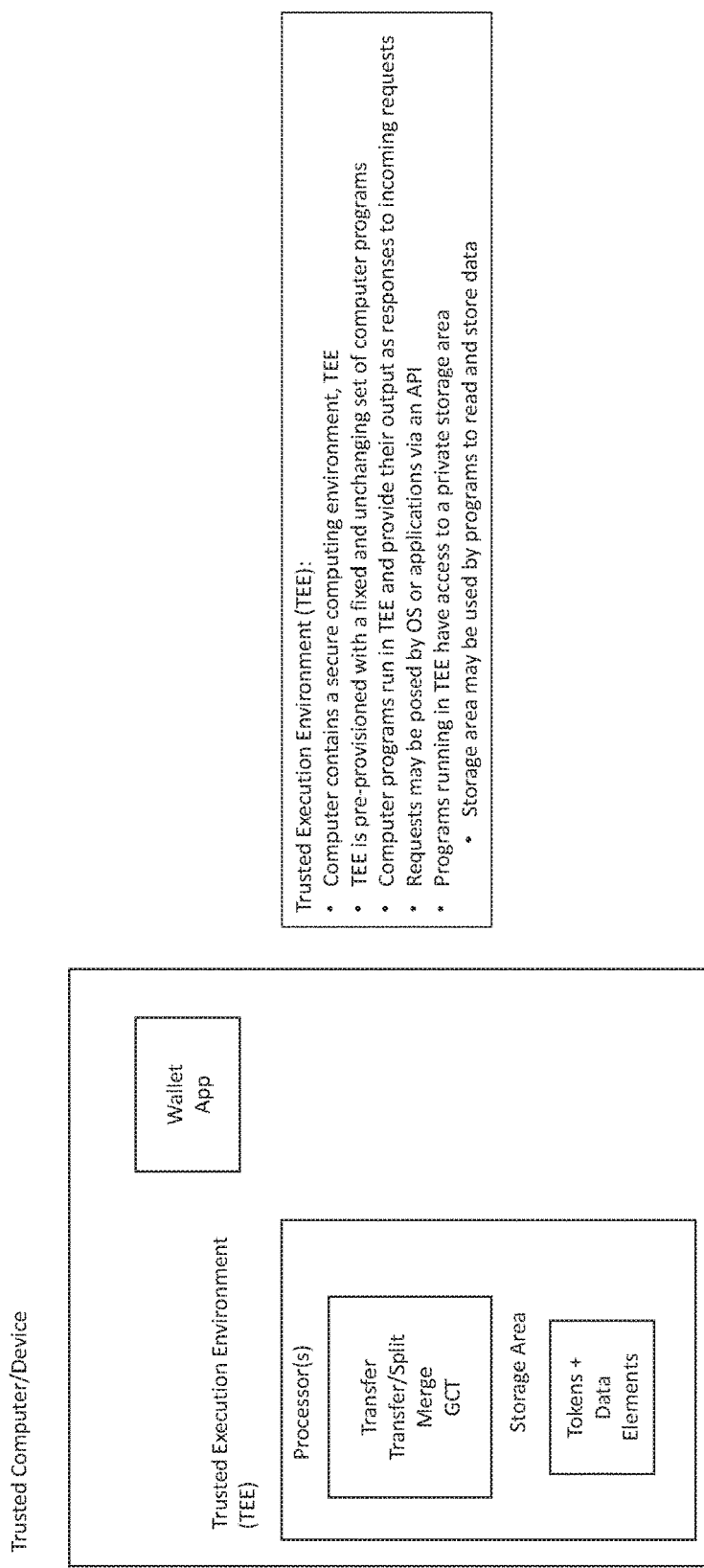
FIG. 10A: Trusted Computers/Devices

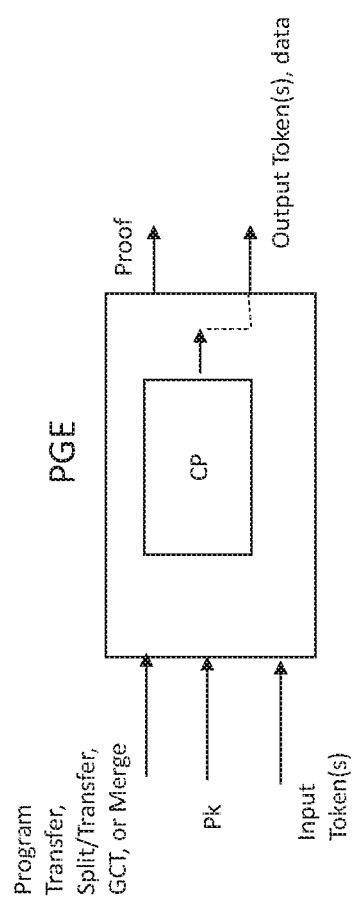
FIG. 10B: Running Programs using program proof execution technology

Method:

1. Launch PGE with one of the programs Transfer, Split/Transfer or Merge as input and input token(s), T.

2. PGE runs indicated program with input "T".

3. Indicated program creates "output token(s)" and data as output

4. PGE produces "proof" as output

5. Output proof and data & token(s), if any

6. Update ledger/record-keeper asynchronously

End Method

FIG. 10C: Method Running Programs using program proof execution technology

Method:

1. Launch PGE with program Generate Commitment Trigger, GCT, as input.
2. PGE runs program GCT as one input; second input to PGE is empty.
3. GCT receives request for commitment trigger, CT.
4. GCT generates and provides CT.
5. GCT receives token, T and proof, P.
6. GCT verifies token T and P.
7. GCT produces proof object "Proof" as output.
8. GCT updates ledger/record-keeper asynchronously.

End Method

FIG. 10D: Method Running GCT using program proof execution technology

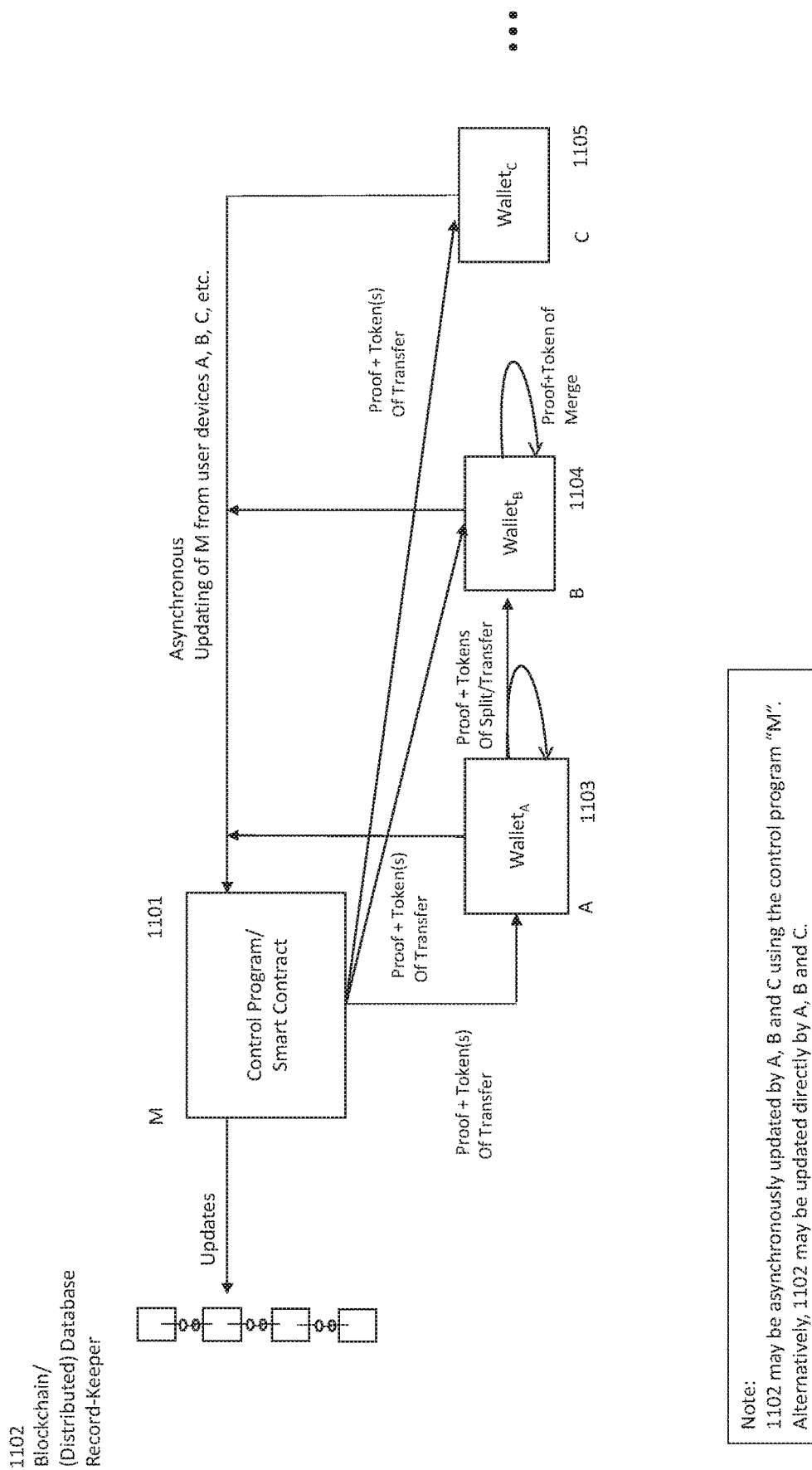
FIG. 11: Proof-based decentralized transactions with asynchronous state maintenance Device M has saved commitment trigger $r1_{MM}$
Device A generates new commitment trigger $r_{MM}$ upon request Program: Transfer "Amount" from device M to device A.

1. Transfer(Amount, device M, device B)
2. Read saved commitment trigger, $r1_{MM}$, from Store; if not available, exit.
3. Get new commitment trigger $r_{AM}$ from device A
4. Calculate $C_{MM} = F(r_{MM}, m_M)$ ⎫
5. Calculate $C_{AM} = F(r_{AM}, m_A)$ ⎬ Commitment calculation
6. Calculate $C_{MM,AM} = (C_{MM} * C_{AM})$ ⎭
7. [Verify Bal >= Amount && Create and output token = {Bal, $C_{MM}$, "blank", $C_{MM,AM}$} && Destroy $r1_{MM}$ ]

end program Transfer

FIG. 12: Program "Transfer" run by PGE on device "M" of FIG. 11

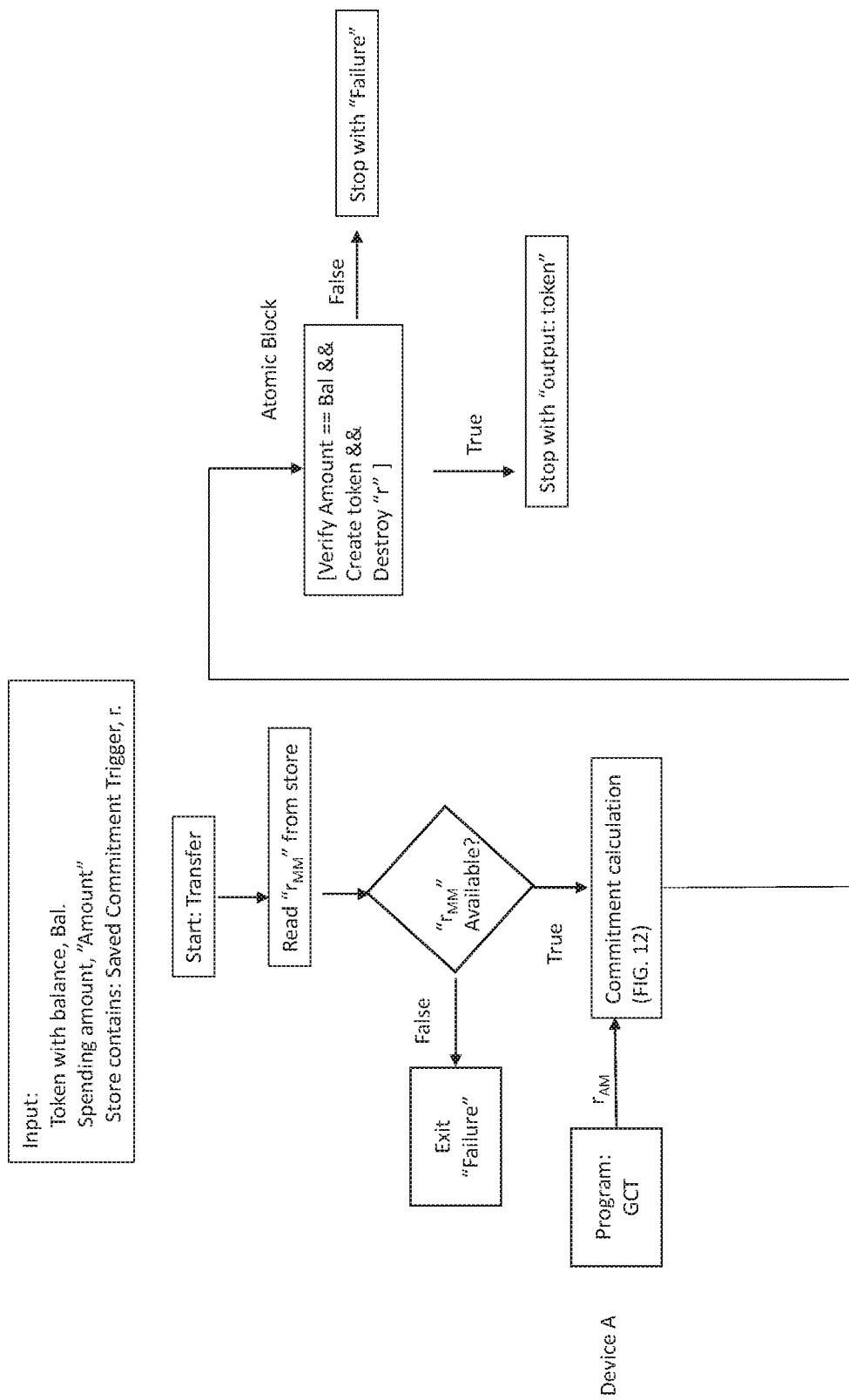
FIG. 13: Flow Chart For Program "Transfer"

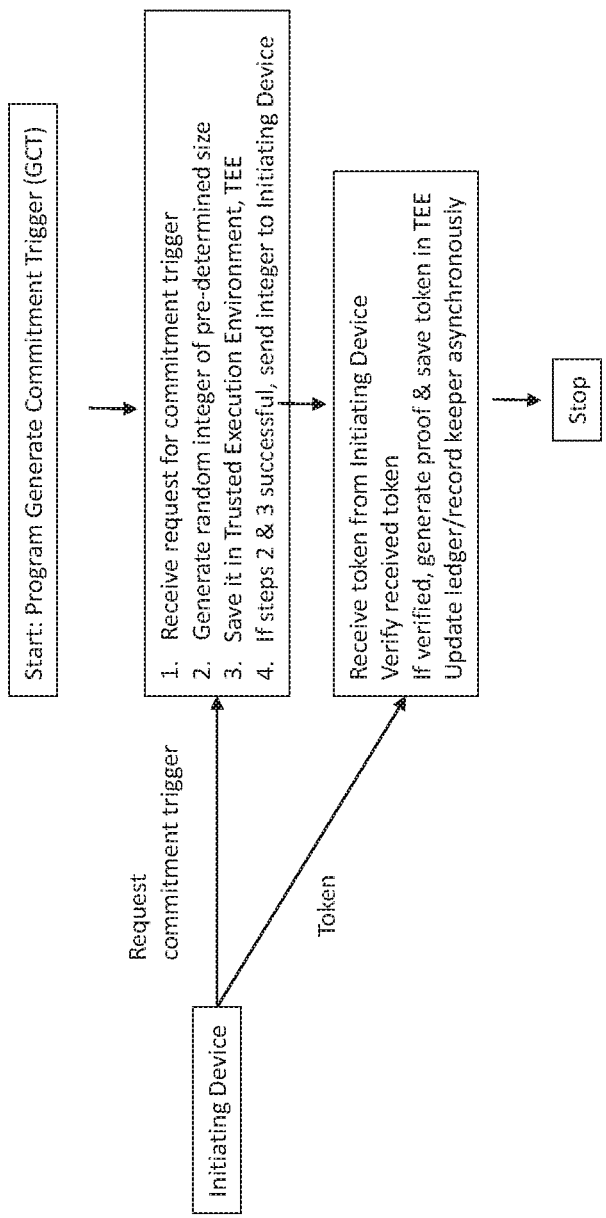
FIG. 14: Flow Chart For Program "Generate Commitment Trigger (GCT)"

< Device A [PGE/Split/Transfer] {Proof}{Token}{5G}:{Proof} [PGE/GCT] Device B>

&&

<Device A [PGE/Split/Transfer] {Proof}{Token}{95G}:{Proof} [PGE/GCT] >

FIG. 15: Succinct Representation of Split/Transfer

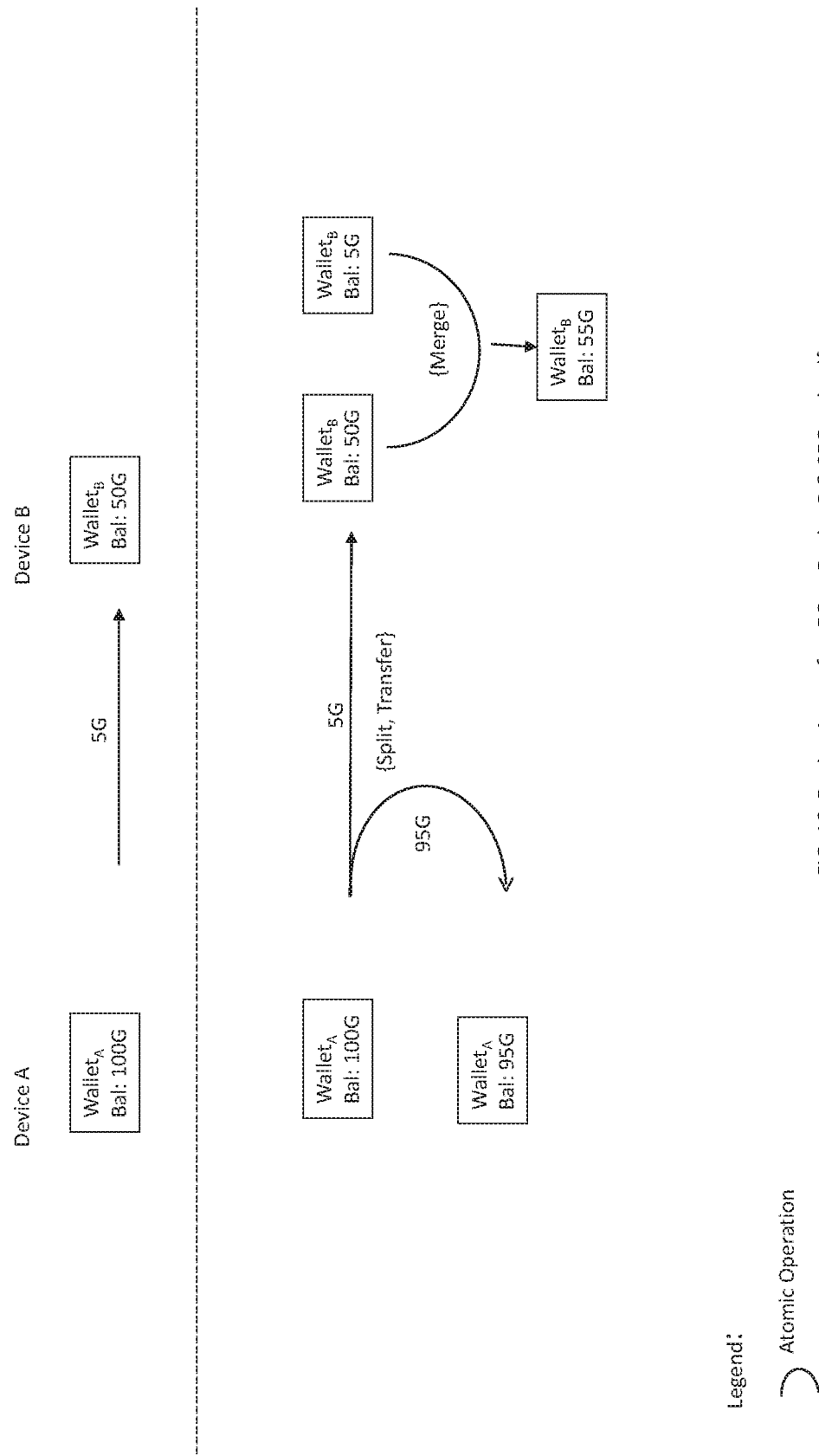
FIG. 16: Device A transfers 5G to Device B & 95G to itself

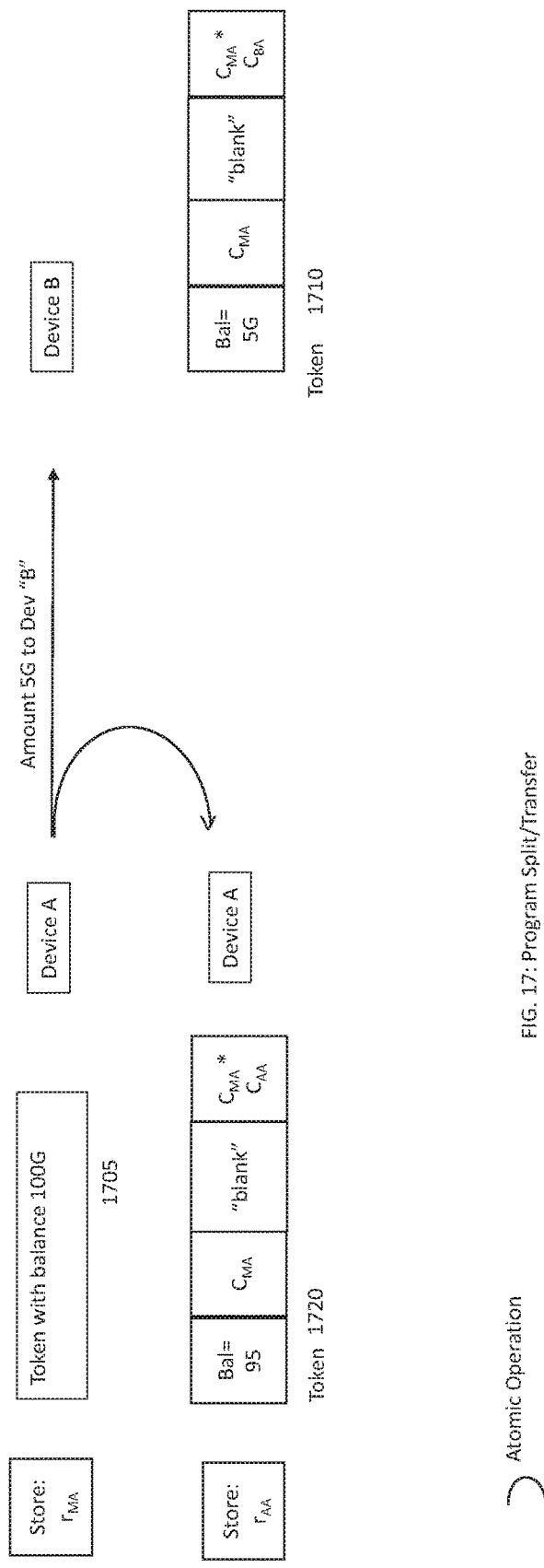
FIG. 17: Program Split/Transfer

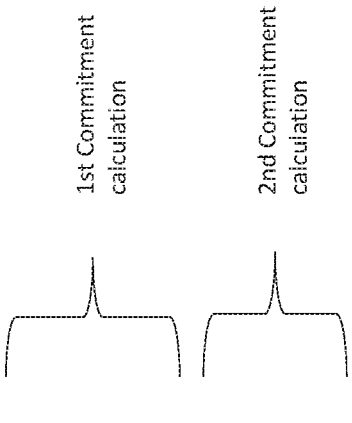
FIG. 18: Program: Split/Transfer

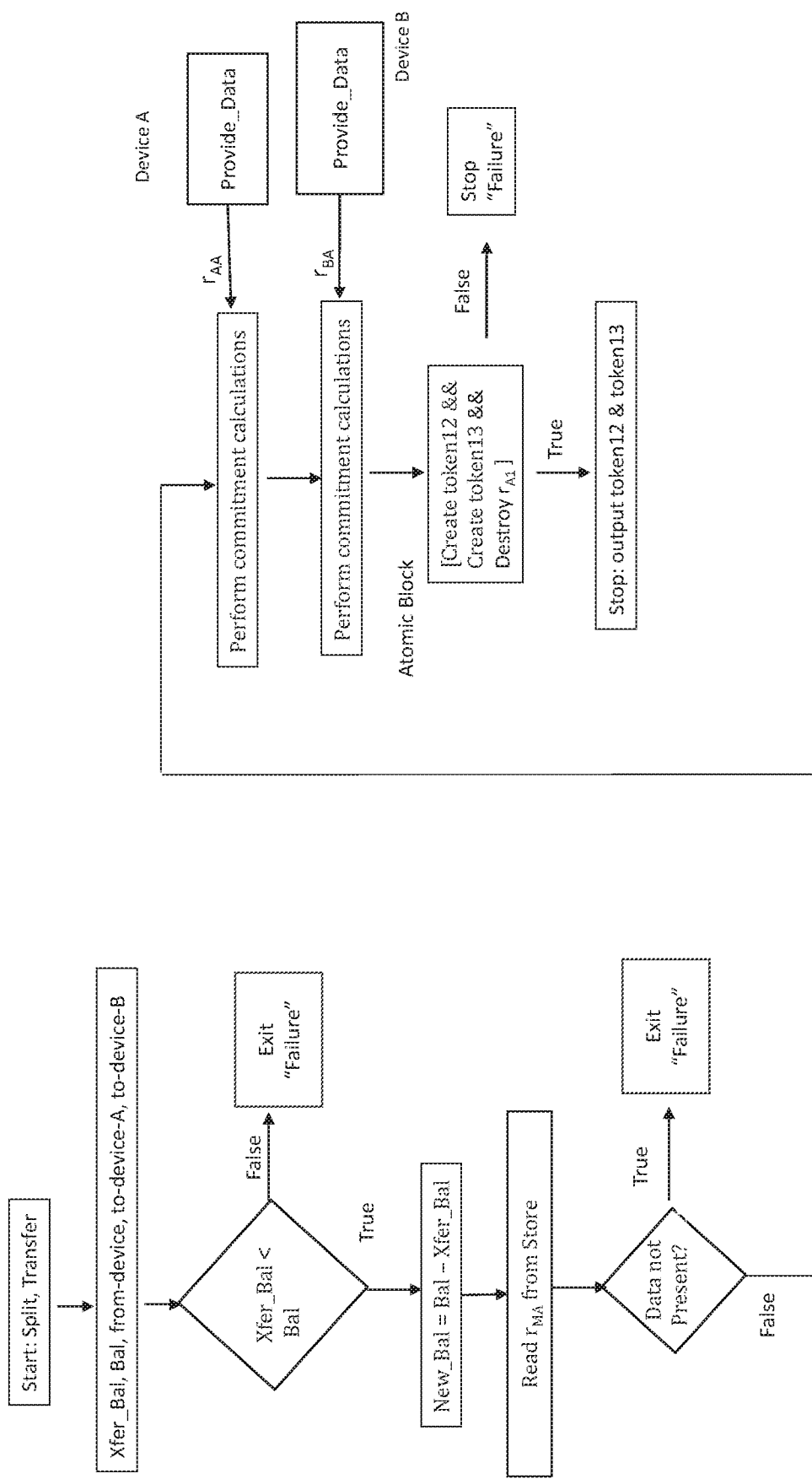
FIG. 19: Flow Chart for Program: Split/Transfer

< Device B [PGE/Merge] {Proof}[Token]{50G}{5G}:{Proof} [PGE/GCT]>

FIG. 20: Succinct representation for transaction using "Merge".

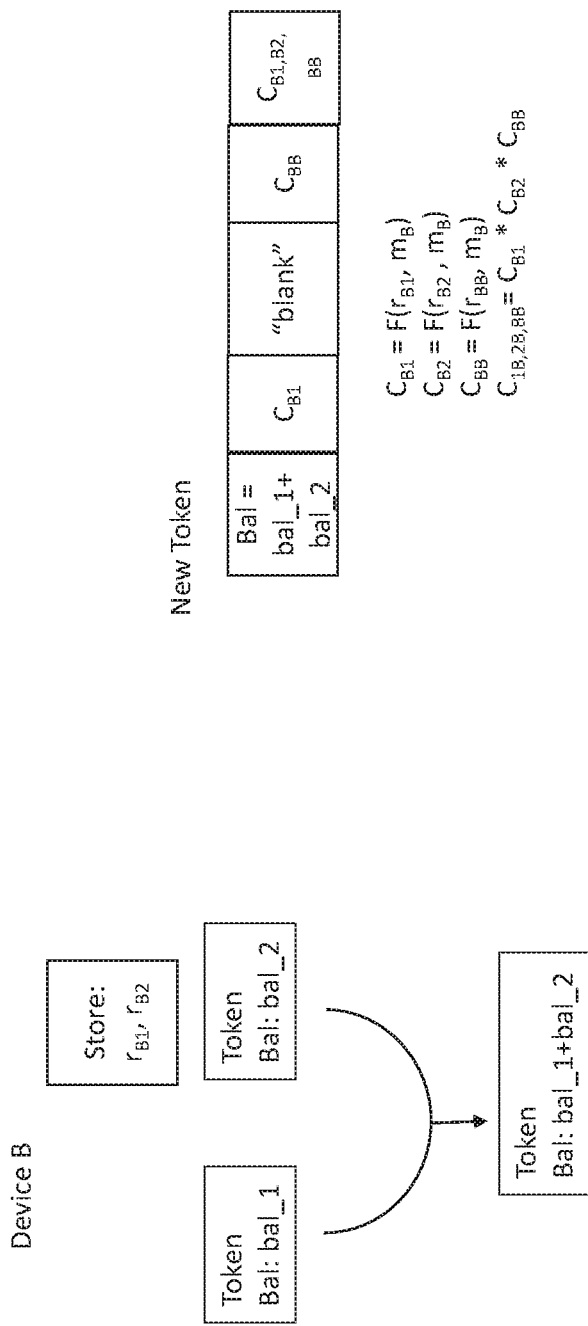
FIG. 21: Program "Merge"

Program: Merge [Device "B" has two tokens, say from devices "1" & "2" with 2 commitment triggers $r_{B1}$ and $r_{B2}$]

Merge(token1 with balance bal_1, token2 with balance bal_2)

Read $r_{B1}$ and $r_{B2}$ from store; if data not present, exit

Calculate New_Bal = bal_1 + bal_2

Calculate $C_{B1} = F(r_{B1}, m_B)$ ⎫

Calculate $C_{B2} = F(r_{B2}, m_B)$ ⎪

Get new commitment trigger from device "B" ⎬ Commitment calculation

Compute $C_{BB} = F(r_{BB}, m_B)$ ⎪

Compute $C_{B1,B2,BB} = C_{B1} * C_{B2} * C_{BB}$ ⎭

[Create token(New_Bal, $C_{B1}$, "blank", "blank", $C_{B1,B2,BB}$) &&

Destroy $r_{B1}$, $r_{B2}$]

End

FIG. 22: Program: Merge

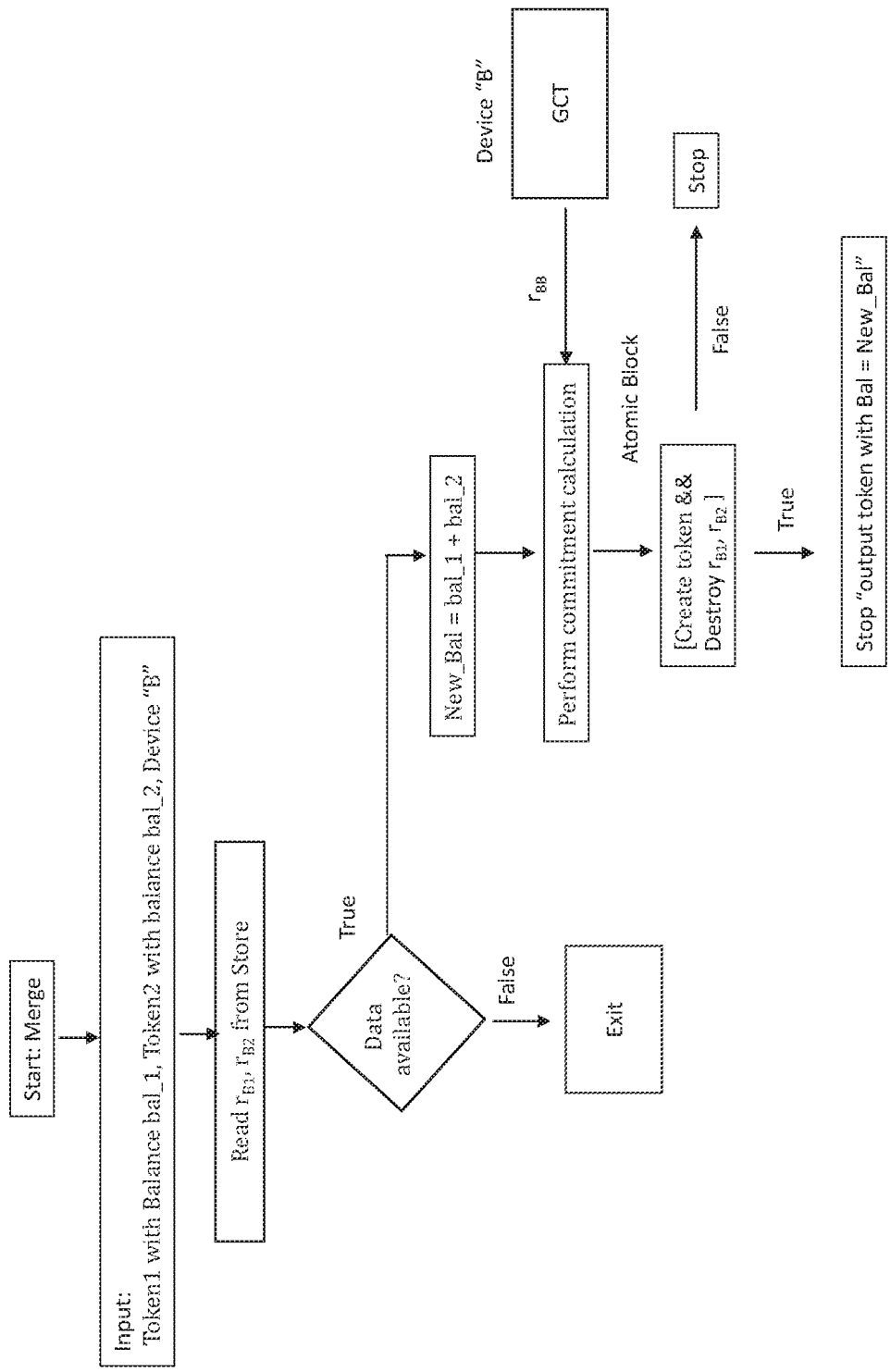
FIG. 23: Flow chart for program Merge

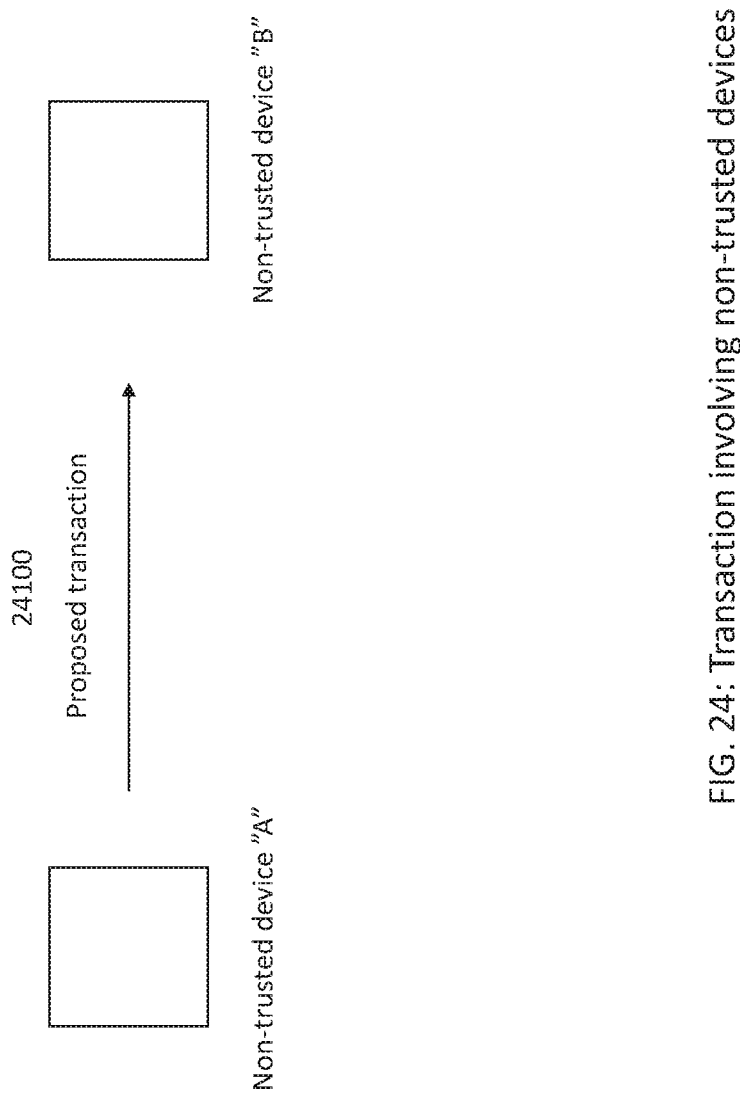
FIG. 24: Transaction involving non-trusted devices

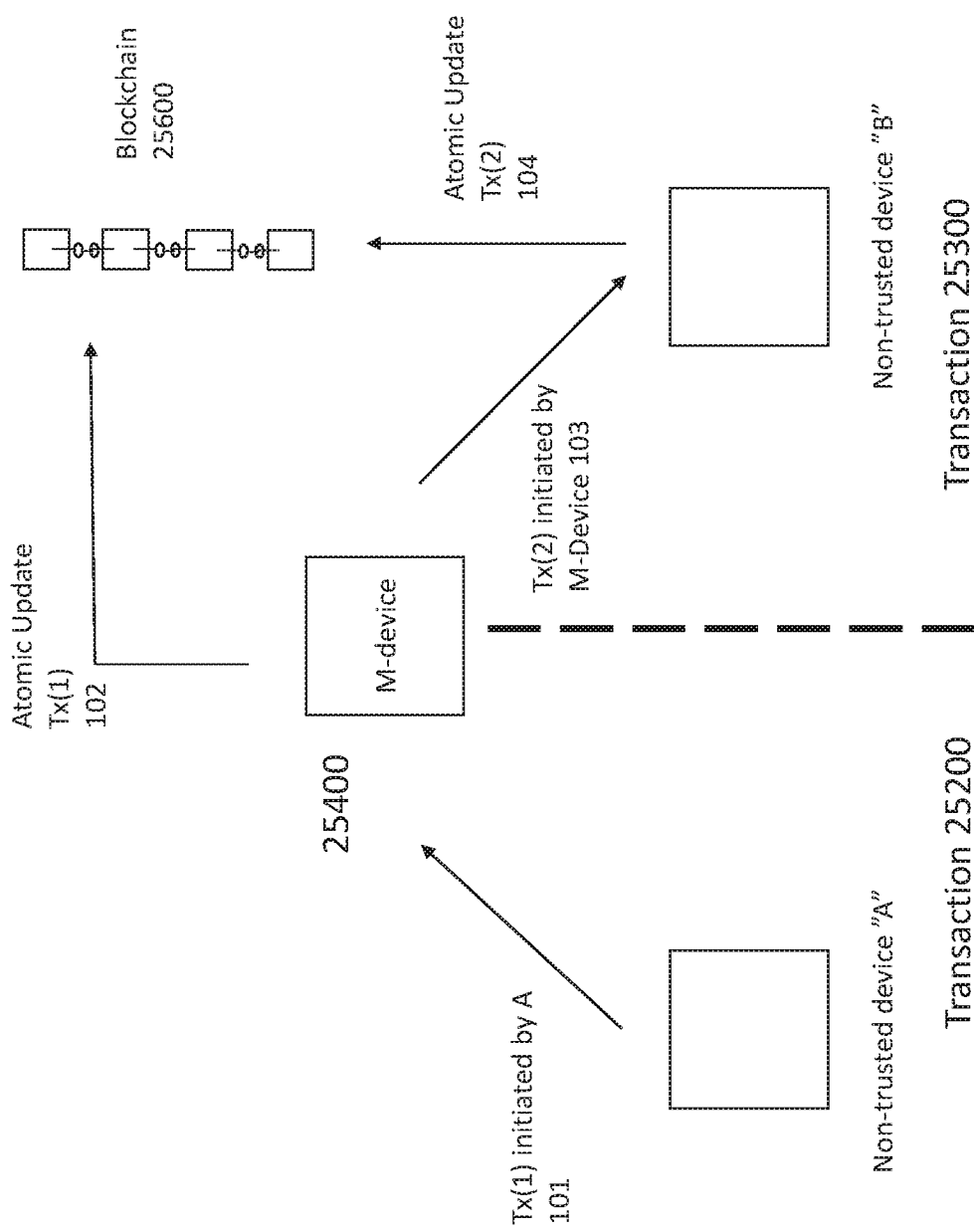
FIG. 25: Implementation of the Transaction of FIG. 24 Using a "Two-legged" Model

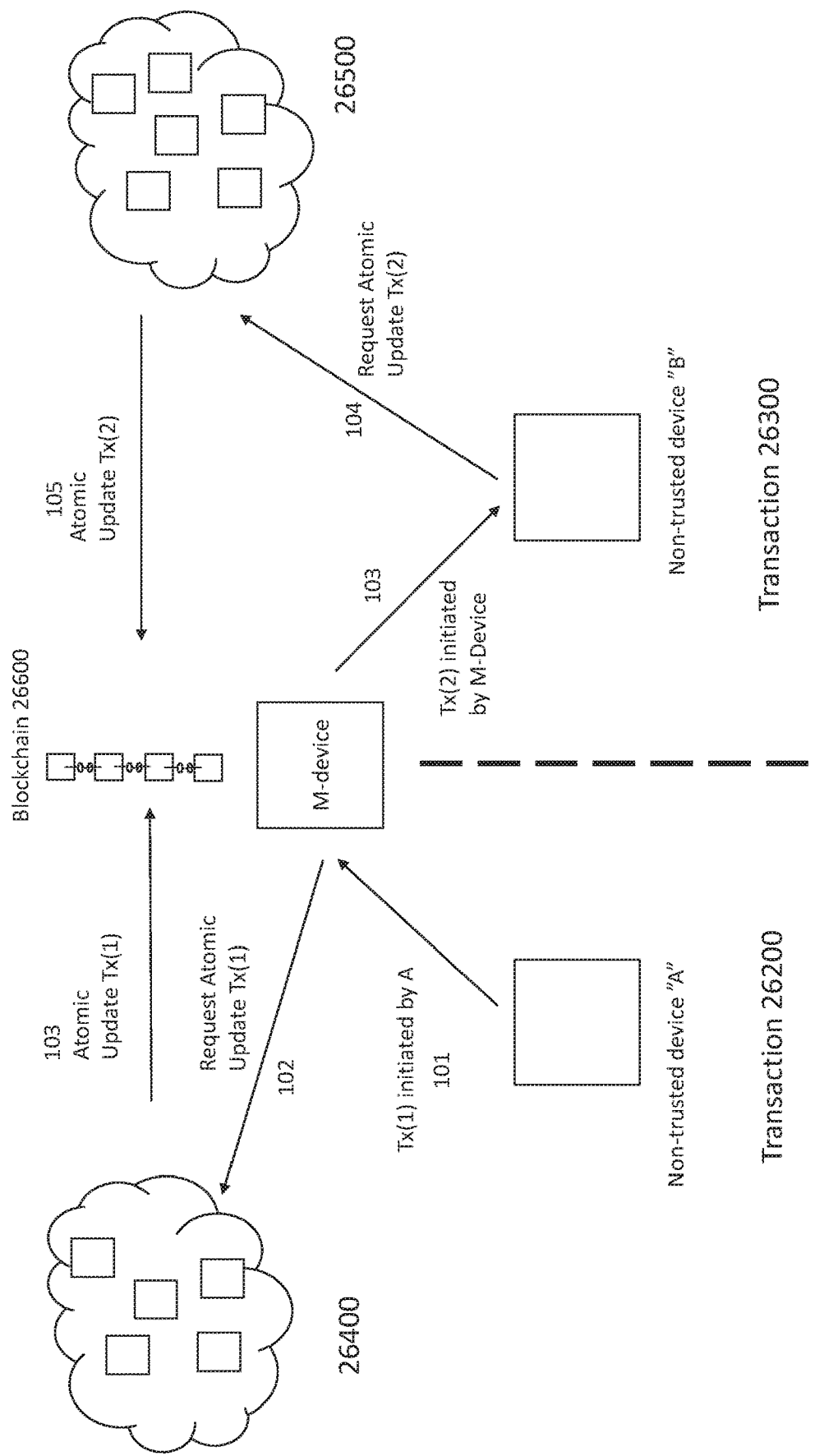
FIG. 26: Embodiment A.

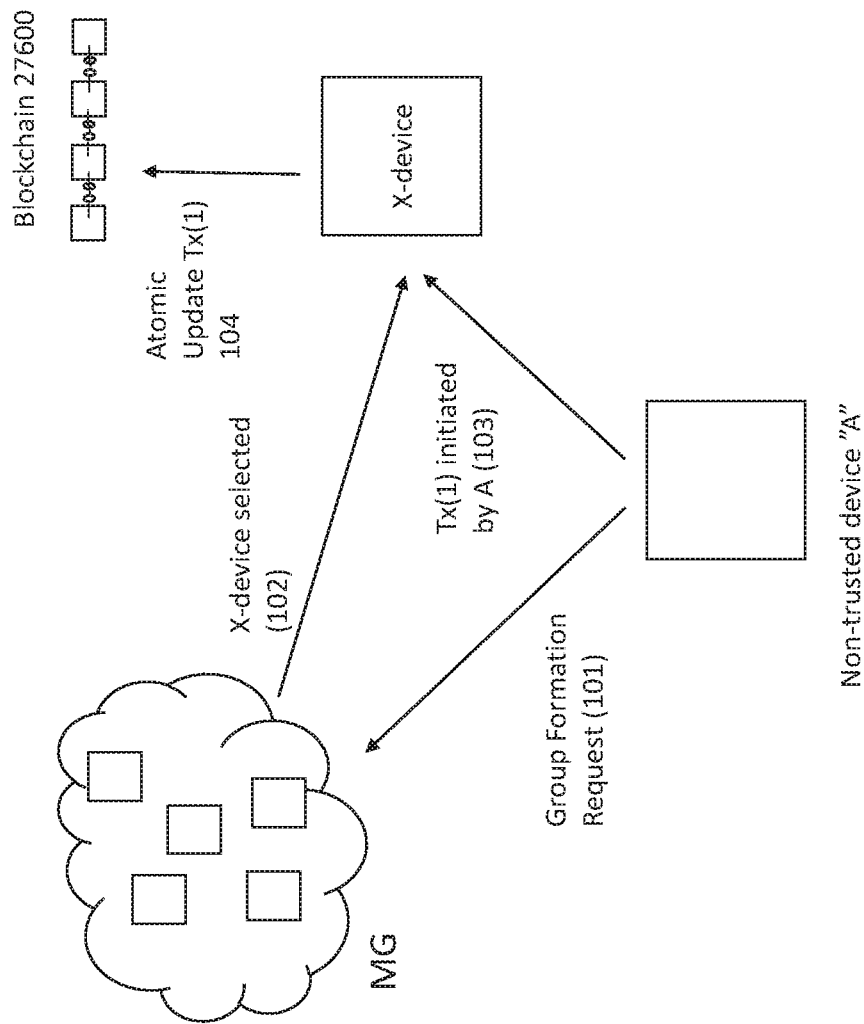
FIG. 27: Embodiment "B" (First Leg)

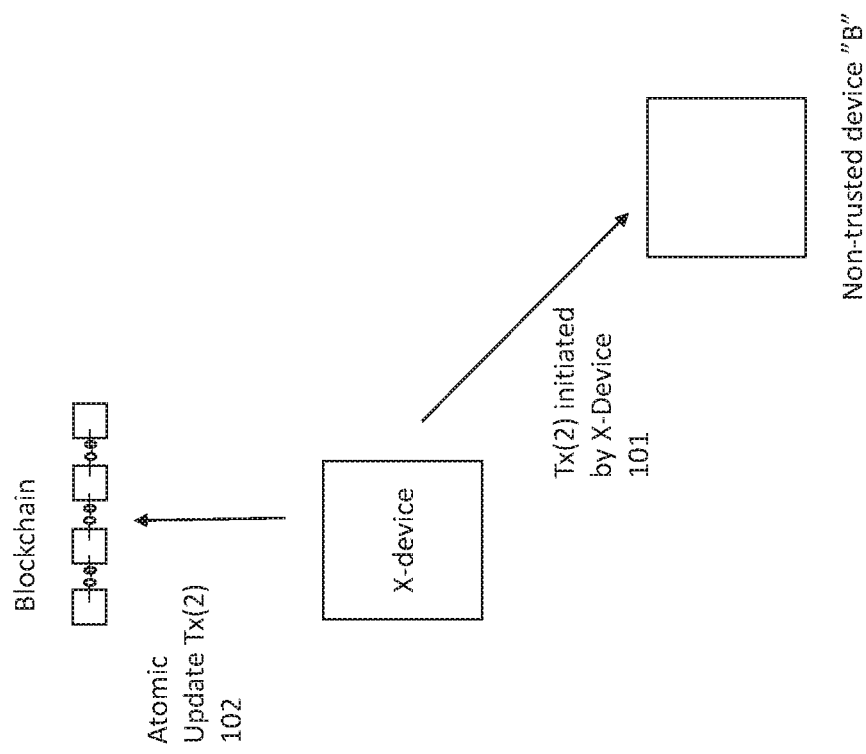
FIG. 28: Embodiment "B" (Second Leg)

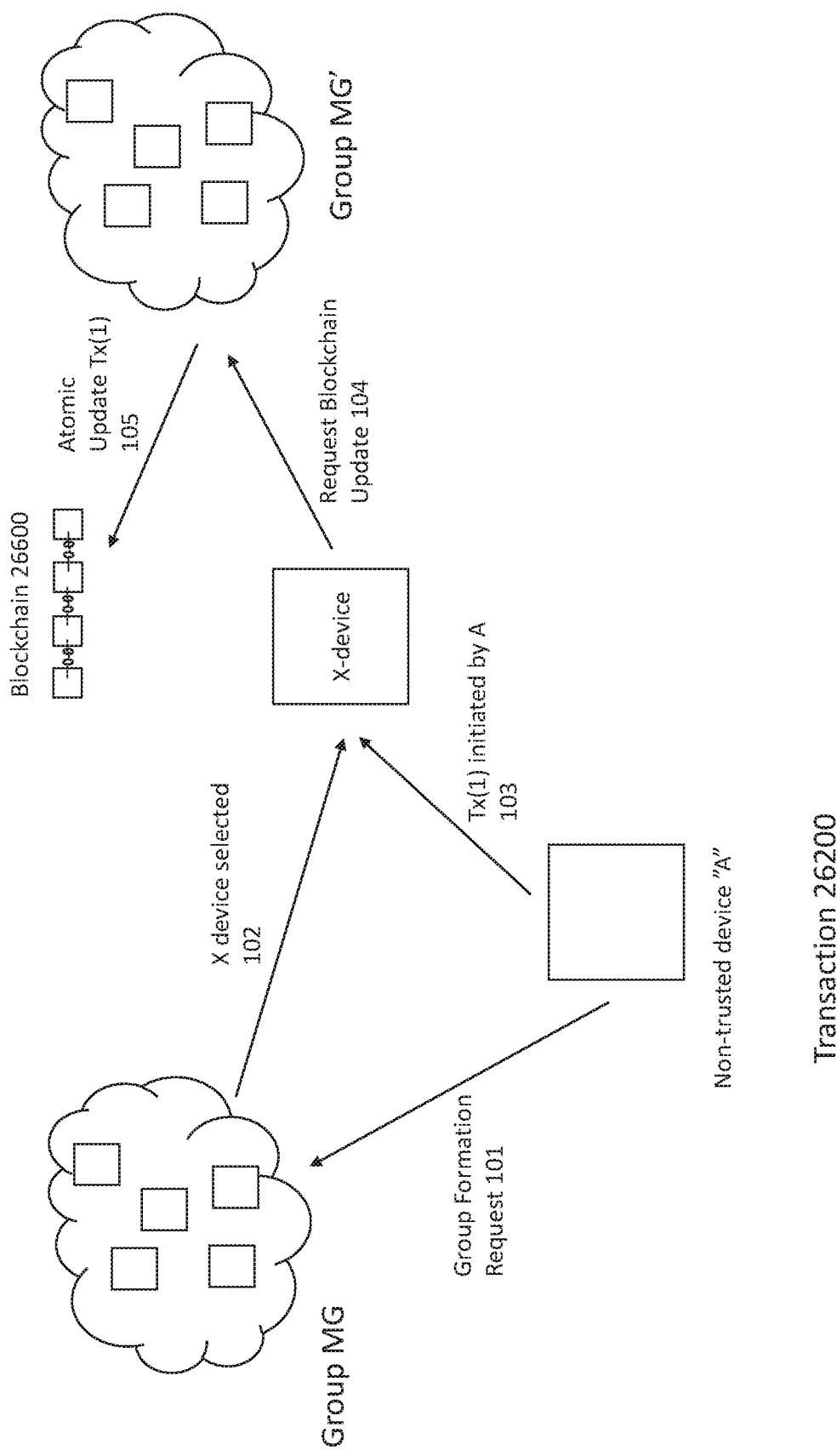
FIG. 29: Embodiment "C" (First Leg of Transaction)

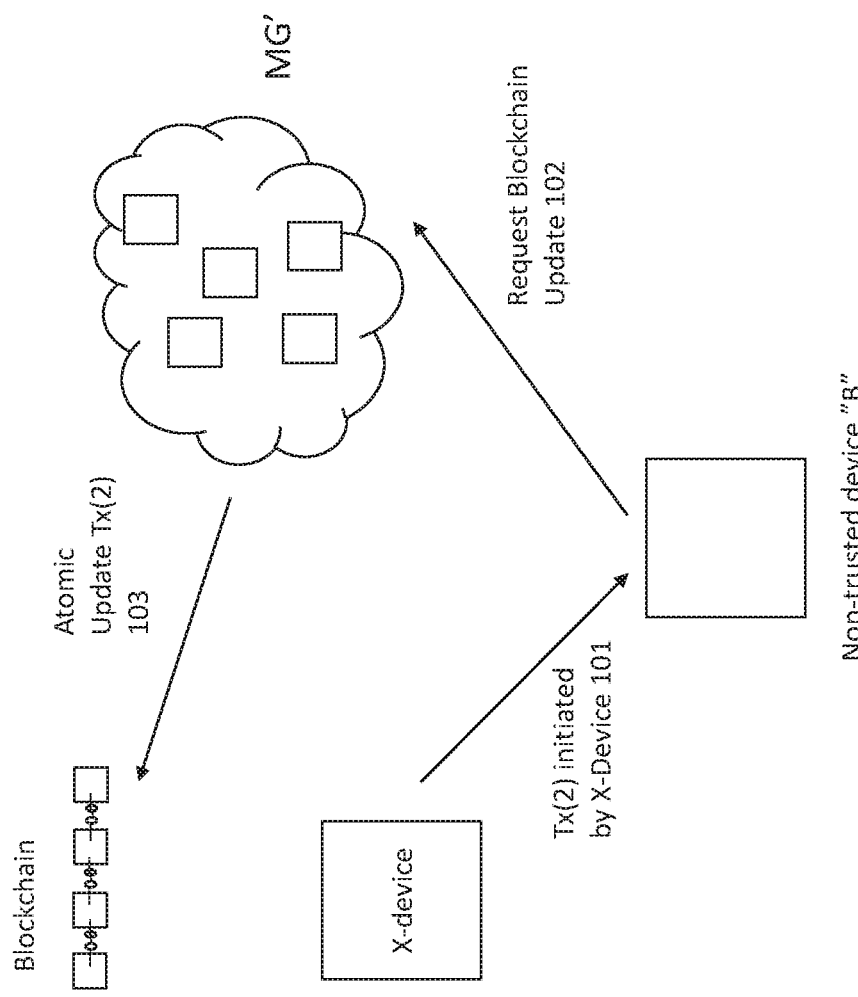
FIG. 30: Embodiment "C" (Second leg of Transaction)

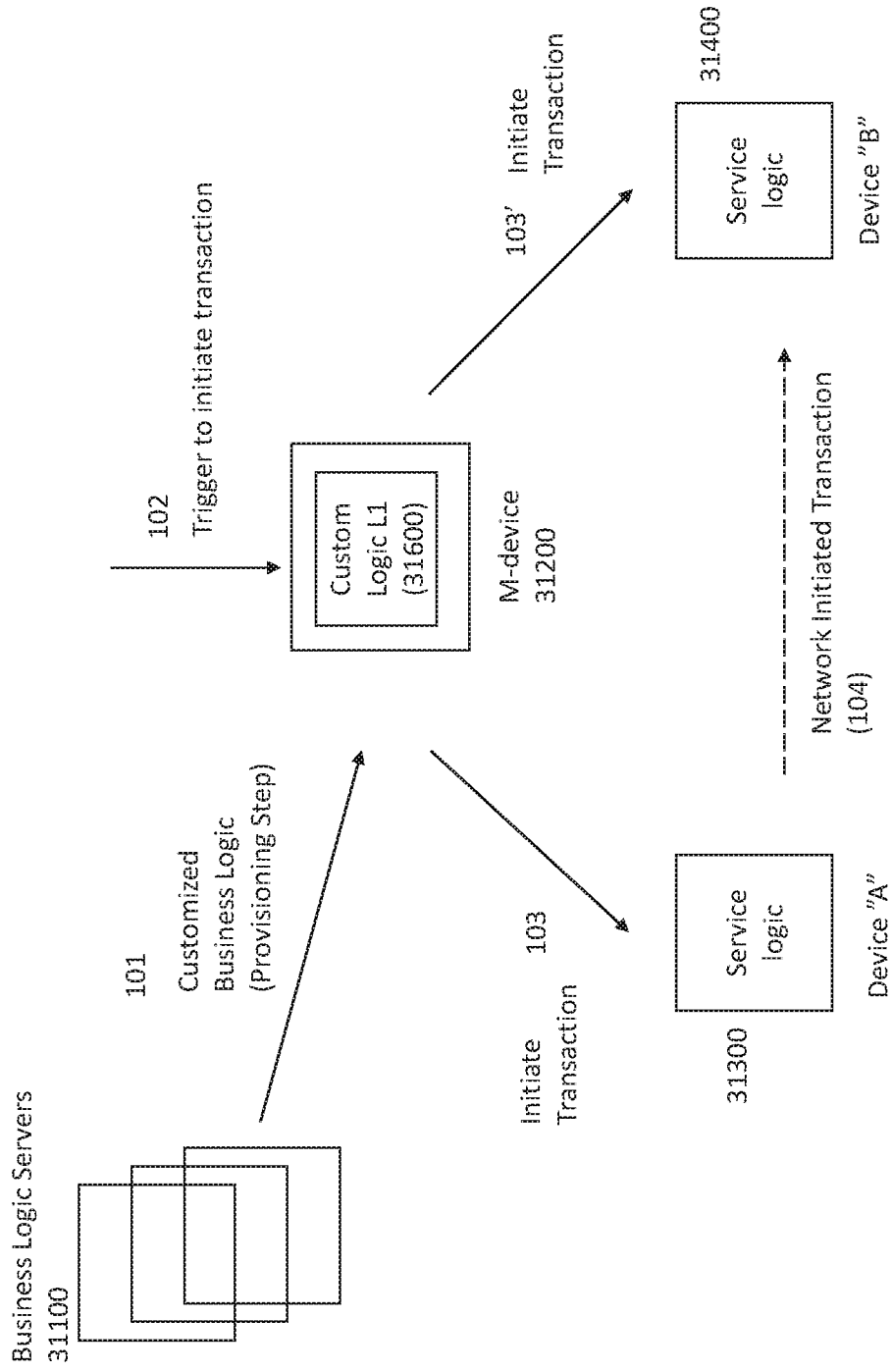
FIG. 31: Transaction Model Using Custom Business Logic

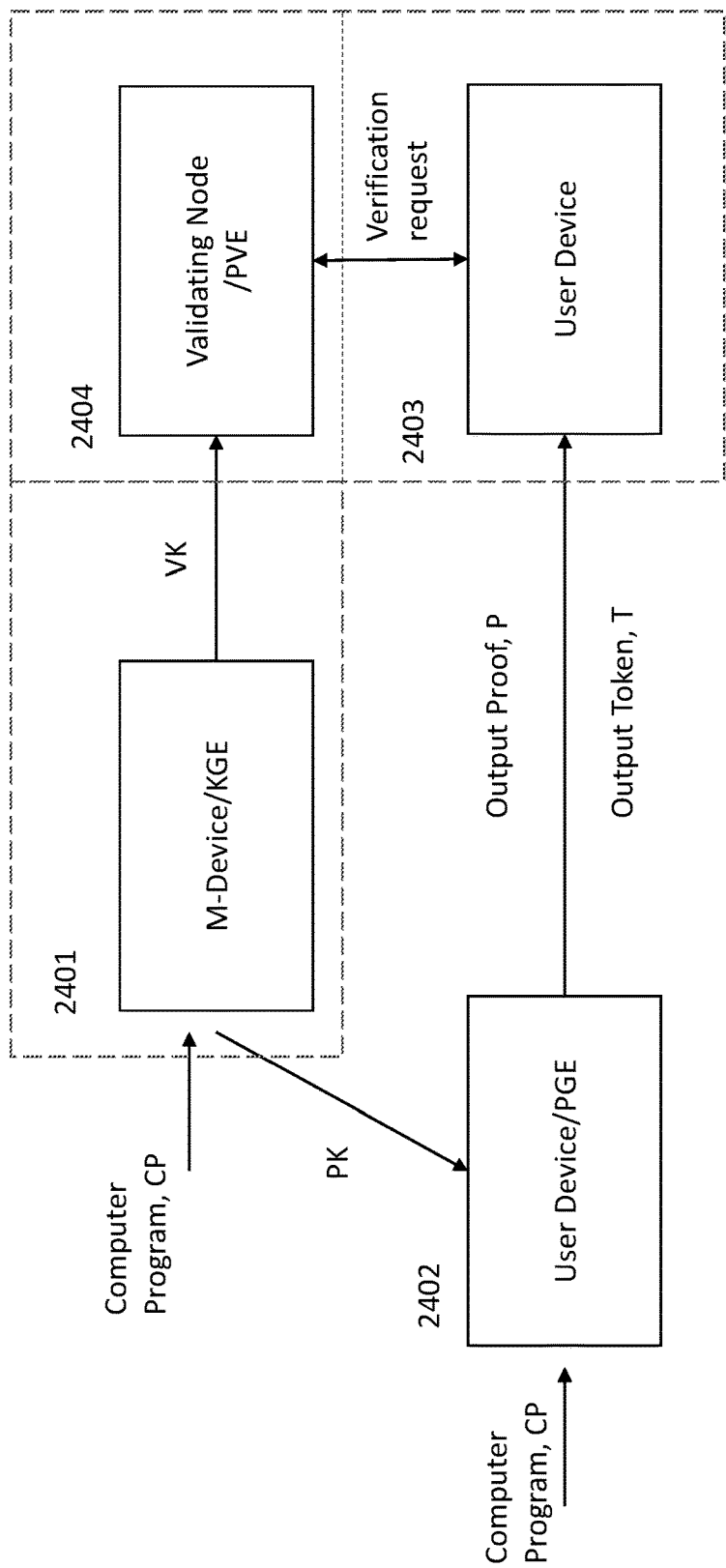
FIG. 32: Summary of Generating and Verifying Proof Objects

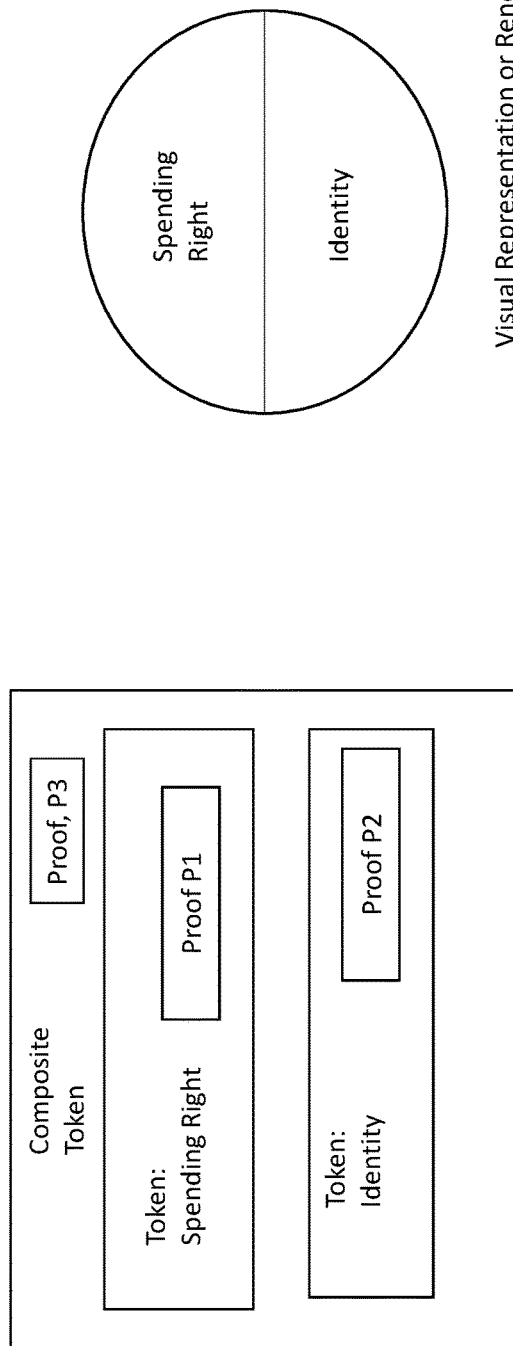
FIG. 33: An example of a composite token with Identity and Payment components

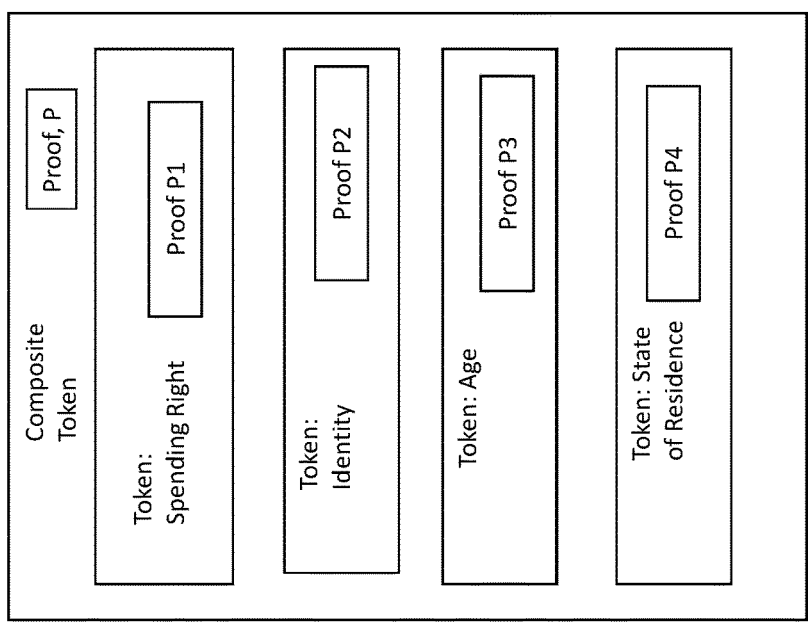
FIG 34: Composite Tokens

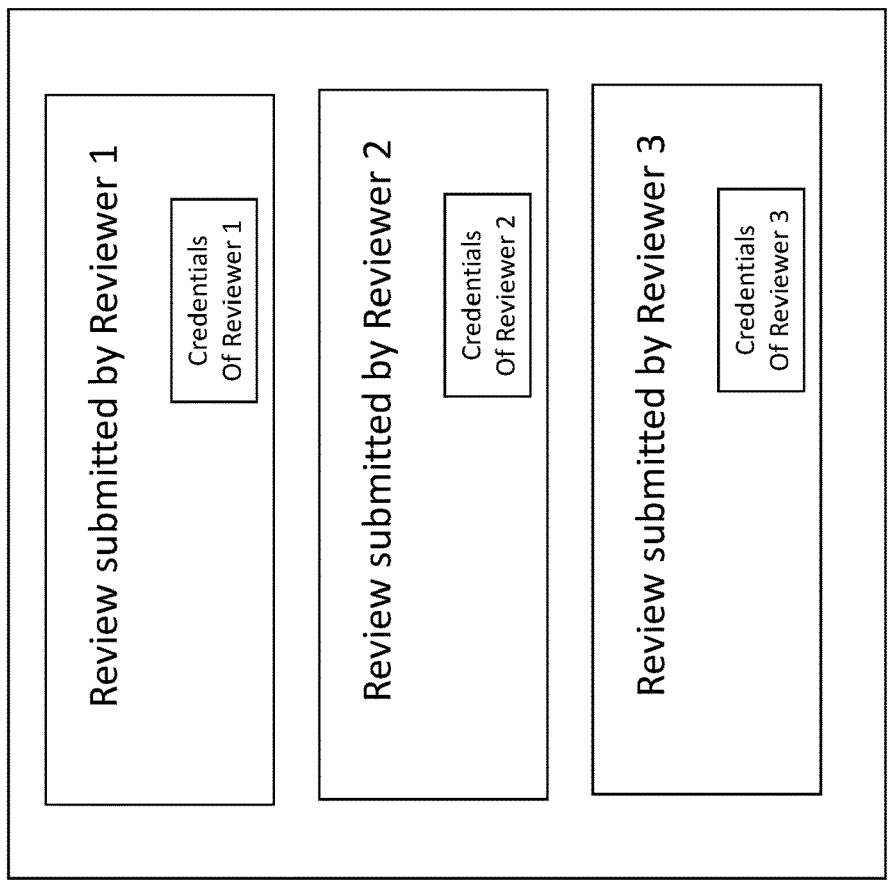
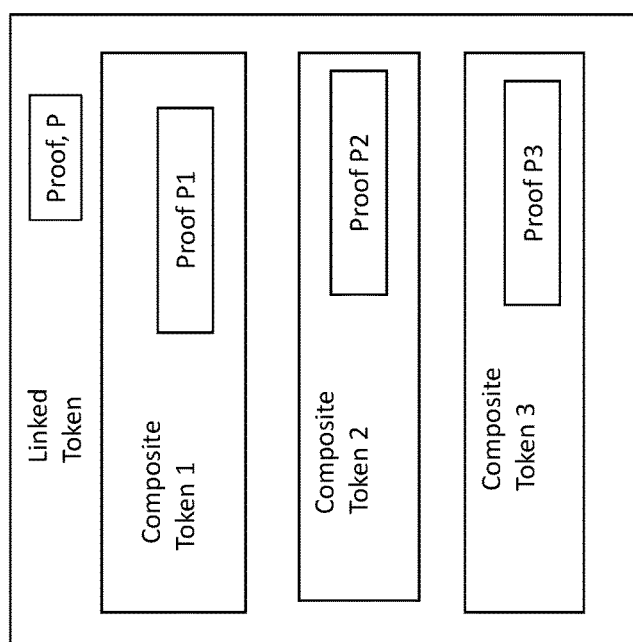
FIG 35: Example of a Linked Token

| Engines | Entities Involved in Transactions |
|---|---|
| KGE, PGE, PVE | Sender (uses PGE), Verifier (uses PVE), Receiver |

Example Implementation Using 4 Computers with KGE & PGE on distinct computers

| Computer 1 | Computer 2 | Computer 3 | Computer 4 |
|---|---|---|---|
| Uses KGE to manage keys | Sender using PGE | Verifier using PVE | Receiver |

Example Implementation Using 3 Computers with KGE & PGE (Sender) on distinct computers

| Computer 1 | Computer 2 | Computer 3 |
|---|---|---|
| Uses KGE to manage keys | Sender using PGE | Verifier using PVE, Receiver |

Example Implementation Using 2 Computers with KGE & PGE (Sender) on distinct computers

| Computer 1 | Computer 2 |
|---|---|
| Uses KGE to manage keys | Sender using PGE, Verifier using PVE, Receiver |

Fig. 36: Example Implementations

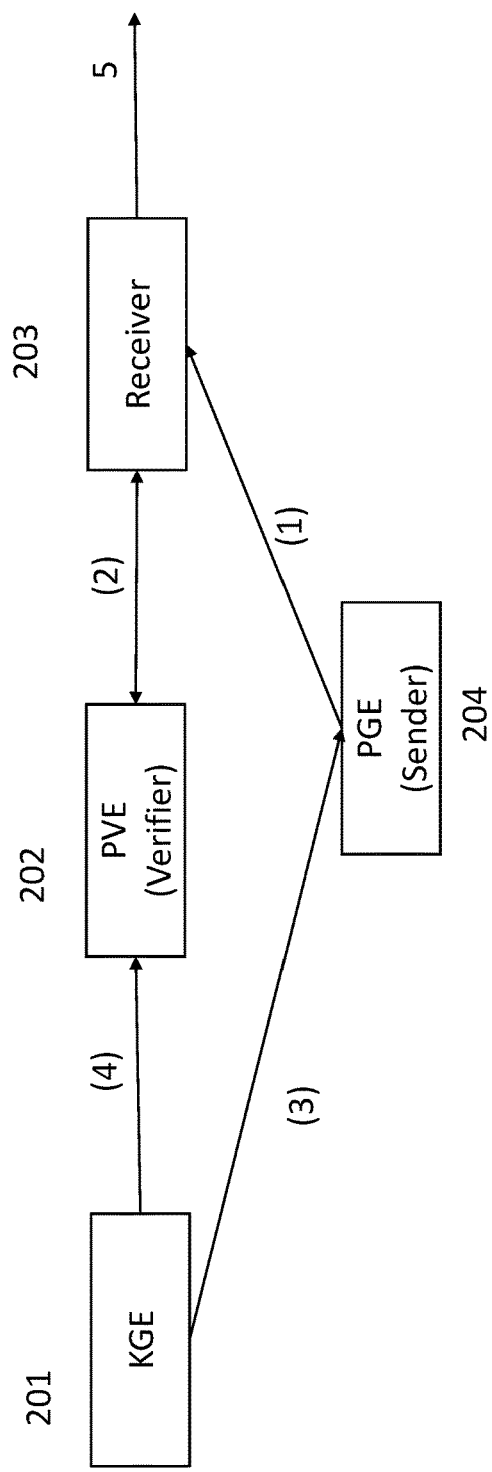
Fig. 37: Implementation Using 4 Computers
Legend:
1 – Transaction
2 – Verification Request & Response
3 – Proving Key
4 – Verifying Key
5 – Action (Yes, No)

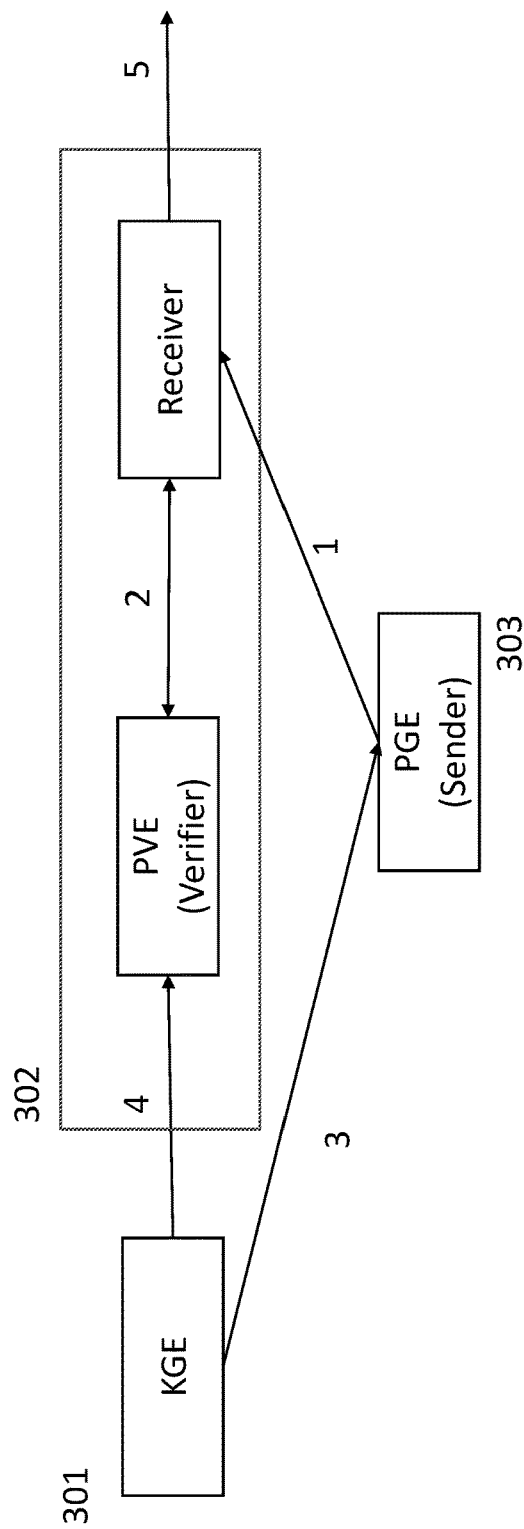
Fig. 38: Implementation Using 3 Computers
Legend:
1 – Transaction
2 – Verification Request & Response
3 – Proving Key
4 – Verifying Key
5 – Action (Yes, No)

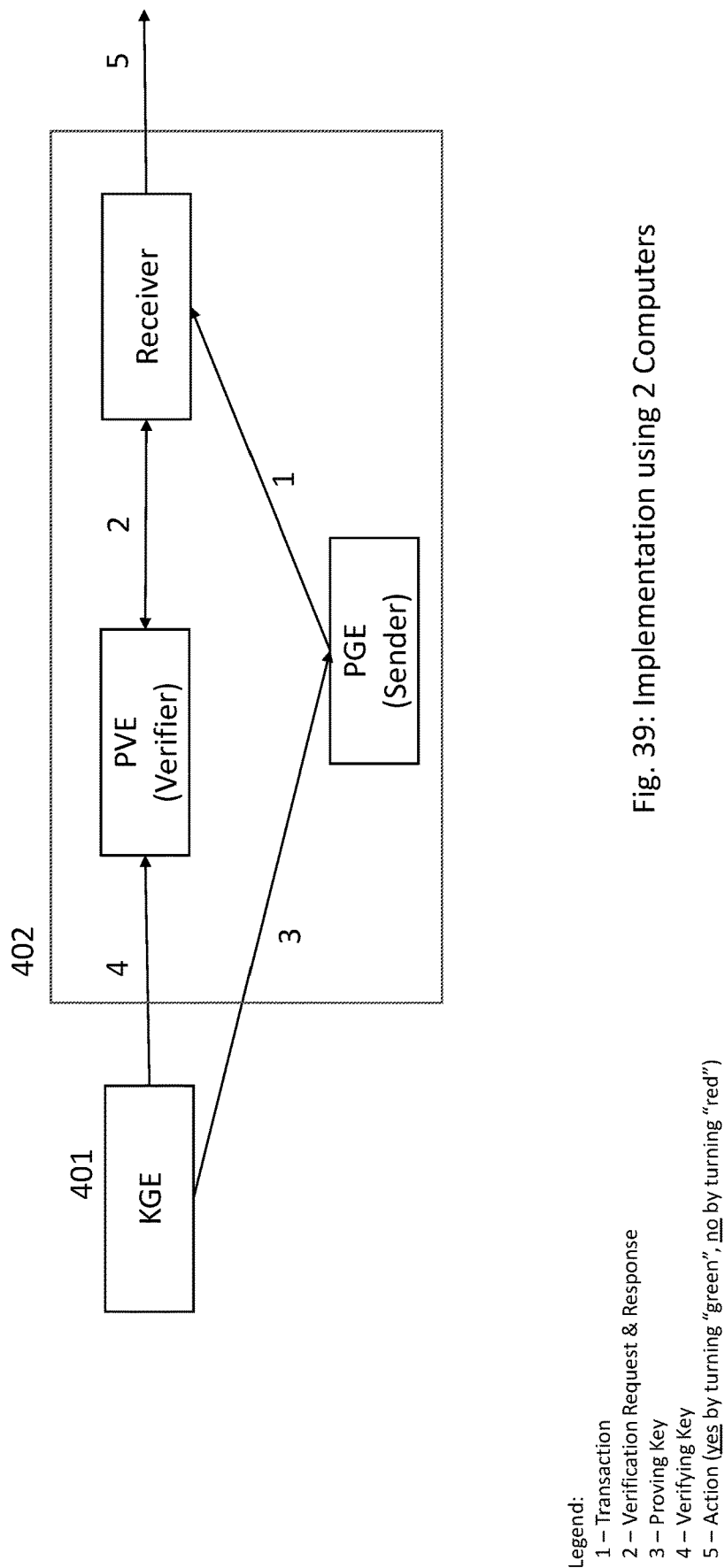
Fig. 39: Implementation using 2 Computers
Legend:
1 – Transaction
2 – Verification Request & Response
3 – Proving Key
4 – Verifying Key
5 – Action (yes by turning "green", no by turning "red")

TESTING AND OTHER DATA COMMUNICATED USING TRUST MODELS IN DECENTRALIZED AND DISTRIBUTED SYSTEMS

BACKGROUND

Distributed and decentralized systems are used in many computing applications where scalability and reliability are important requirements. Applications in transaction processing, digital rights management, cryptocurrencies, travel arrangements, access to resources, financial transactions, etc., make heavy use of distributed and decentralized systems of interconnected computers and components. In such applications, achieving consensus and maintaining a consistent view of the overall system is of great importance and has been the subject of many previous technological innovations and improvements.

Recent applications in cryptographic transactions (e.g., Bitcoin) use consensus methods that use enormous amounts of electrical power and the resulting transaction throughput rates are quite low. The present invention addresses these and other technological problems.

SUMMARY

In accordance with one aspect of the subject matter disclosed herein, a method for communicating information relating to test results of a user, is presented. In accordance with the method, test results of a use are obtained. An assertion is derived from the test results of the user. The test results are input to a pre-provisioned first algorithm. The assertion is encapsulated in a first data object by a PGE that controls an environment in which the first algorithm is executed. A first proof is generated which is configured to be usable to verify that the first algorithm used the test results to produce the assertion when provided to a PVE along with the first data object. The test results itself are excluded from the first proof and the first data object such that privacy of the test results is maintained. The first proof and the first data object are communicated to a receiving communication device from an enterprise communication device associated with the user and an enterprise.

In accordance with another aspect of the invention, a method for communicating information relating to test results of a user includes obtaining test results of a user An assertion is derived from the test results of the user. The test results are input to a pre-provisioned first algorithm. The assertion is encapsulated in a first data object by a PGE that controls an environment in which the first algorithm is executed. A first proof is generated which is configured to be usable to verify that the first algorithm used the test results to produce the assertion when provided to a PVE along with the first data object. The test results itself are excluded from the first proof and the first data object such that privacy of the test results is maintained. The method further includes verifying that the first algorithm used the test results to produce the assertion by providing the first proof and the first data object to the PVE. In response to the verifying, an indicator is presented indicating whether the user has tested positive or negative for a condition.

This Summary is provided to introduce a selection of concepts in a simplified form that are further described below in the Detailed Description. This Summary is not intended to identify key features or essential features of the claimed subject matter, nor is it intended to be used as an aid in determining the scope of the claimed subject matter. Furthermore, the claimed subject matter is not limited to implementations that solve any or all disadvantages noted in any part of this disclosure.

BRIEF DESCRIPTIONS OF THE DRAWINGS

FIG. 1 shows an example of a Bitcoin-style decentralized transaction processing.

FIG. 2 shows the mode of interaction between two client devices in a Bitcoin-style network.

FIG. 3 describes the problem of decentralized transaction processing without a blockchain/ledger.

FIG. 4 shows an arrangement by which decentralized transaction processing may be achieved with asynchronous updating of the blockchain or a distributed database acting as a record-keeper and not being in the path of the transaction.

FIG. 5 shows an alternative arrangement corresponding to FIG. 4.

FIGS. 6A and 6B show models for an exemplary transaction.

FIG. 7A shows an exemplary commitment function and token.

FIG. 7B shows an exemplary verification of tokens.

FIG. 8A shows a review of program proof technology.

FIG. 8B shows exemplary encapsulated messaging/transaction traffic.

FIG. 9 shows an exemplary succinct notation for transactions.

FIG. 10A shows a device with a trusted execution environment.

FIG. 10B shows an arrangement for running a selected program using the engine PGE.

FIG. 10C shows a method for running one of the programs, Transfer, Split/Transfer or Merge using the engine PGE.

FIG. 10D shows a method for running the program GCT using the engine PGE.

FIG. 11 shows a method by which transactions are supported in a decentralized network with asynchronous updating of the record-keeper.

FIGS. 12 and 13 show the method "Transfer" and its corresponding flow chart.

FIG. 14 shows the method of program Generate Commitment Trigger (GCT).

FIG. 15 shows a succinct notation for an exemplary transaction.

FIGS. 16 and 17 show execution plans for a "Split/Transfer" transaction between client devices.

FIGS. 18 and 19 show the method "Split/Transfer" and its flowchart.

FIG. 20 shows the succinct transfer representing the "Merge" transaction.

FIG. 21 shows the execution plan for the "Merge" program.

FIGS. 22 and 23 shows the method and flow chart for the "Merge" program.

FIG. 24 describes the general model of two non-secure devices executing a transaction.

FIG. 25 describes a "two-legged" transaction model to support the transaction of FIG. 24.

FIG. 26 describes embodiment "A" for executing transactions using non-secure devices.

FIG. 27 describes embodiment "B" for executing the "first leg" of transactions using non-secure devices.

FIG. 28 describes embodiment "B" for executing the "second leg" of transactions using non-secure devices.

FIG. 29 describes embodiment "C" for executing the "first leg" of transactions using non-secure devices.

FIG. 30 describes embodiment "C" for executing the "second leg" of transactions using non-secure devices.

FIG. 31 describes a transaction model in which customized logic is used to control elements of transactions.

FIG. 32 summarizes the use of the KGE, PGE and PVE engines.

FIG. 33 shows an example of a composite token with payment and identity sub-components.

FIG. 34 shows an example of a composite token with payment, identity, age and state of residence sub-components.

FIG. 35 shows an example of a linked token.

FIG. 36 shows a simple table listing the various engines and the roles played by physical devices.

FIGS. 37-39 illustrate various alternative arrangements of communication devices that may be used to implement the systems, techniques and methods described herein.

DETAILED DESCRIPTION

Motivation

Transaction processing systems comprise databases, application programs, state monitoring systems, and networks of multiple devices. They occupy a basic place and play a fundamental role by providing support to data operations in communications, finance, manufacturing, travel, entertainment, crypto-currencies and process control.

A database is a dataset that represents the state of a physical or an abstract system. A request or a query is a computer program/command that returns the (current) state of the database. A transaction is a collection of one or more computer programs that transform the state of the database system into one or more new states. A transaction processing system is a collection of computer programs running on computing devices providing operational support for transactions. A distributed system is a collection of inter-connected computers communicating using one or more communication (messaging) protocols. A decentralized system is a (distributed) system in which no single entity controls all the computers.

Maintaining consistency or achieving consensus under state changes is a crucial requirement for transaction processing systems in distributed and decentralized systems and finds its expression in many applications.

In fault tolerance applications the consensus problem relates to ascertaining the reliability of inter-connected computers/components. A group of inter-connected computers may communicate with each other via messages. One or more of the connected computers may become faulty and send out conflicting messages, e.g., it may send messages indicating it is faulty to some components and that it is functioning properly to other components. The problem is to detect faulty components from the received messages and reach consensus throughout the network.

In crypto-currencies and financial transaction systems the consensus problem is usually described as the "double-spend" problem wherein a user (or a group of users) maliciously conspire to spend more than their amount balance. In Bitcoin-style networks (cf. FIG. 1) users may transfer their "unspent transaction outputs" (UTXO) to other users. The problem is to reach consensus amongst the computers managing or executing the transactions that no double-spend events have occurred.

Consider a user, say Alice, having a certain amount of UTXO. In order to transfer some of her spending rights to another user, say Bob, she initiates a transaction request assigning her spending right to Bob by using Bob's address (a hashed number represented by a bit string) and "signs" the transaction by using Bob's public key. (It is well-known that a signed transaction can only be accessed by a user possessing the corresponding private key.) In turn, Bob wishing to transfer the spending right transferred to him by Alice to another user, say Charlie, accesses the transaction using his private key. The UTXO and the associated transfer of spending rights are called transactions that are recorded in a ledger called the blockchain. On occasion, the terms "blockchain" and "ledger" may be used as synonyms.

Generally, the ledger preserves the integrity of the system's transactions and is the sole arbiter of the history of the transaction system. Any third-party client may verify the integrity of a public ledger by re-building the ledger from its initial state. Thus, the blockchain represents the correct and true history of the network. All Bitcoin clients (also called wallets) are user interfaces displaying the state of the data on the blockchain. For example, a wallet displaying a balance of a user shows the UTXO of that user as reflected by the data on the blockchain.

One or more users may conspire to double-spend their UTXO and thus corrupt the blockchain. To avoid the double-spend problem and maintain consistency of or consensus on the blockchain, Bitcoin-style networks use a method that may be described as follows.

A group of inter-connected (networked) nodes, called miners, are especially configured to perform a certain computing task or "work" and provide "proof" that the task or work has been completed. The idea is to determine the first node that provides a successful proof (of work). Each miner receives transaction requests from clients (wallets) and records the requests in a local memory called the "block". All requests received by a miner are broadcast to all the other miners. Thus, every miner has its own identical block of received requests.

We are now required to select one of the miners and allow him to add his block of transactions to the blockchain. The selection metric is the proof of work. A miner announces that it has successfully performed the work and provides a proof. The proof is verified by one or more of his contemporaries, i.e., other miners. Upon verification, the successful miner may add his block to the blockchain. (The verification involves checking the integrity of transactions in the block against the transactions in the overall ledger.)

Inconsistent transaction requests received by two miners cannot be added to the blockchain since only one miner is selected and his block is checked and verified before it can be added to the blockchain. Thus, the proof of work metric may be said to prevent the double-spend problem. Alternatively, we may state that the method to achieve consensus is based on the proof of work metric. An additional step may be added to the above procedure for taking care of network-splits. In relevant literature, the above method by which new blocks are added to the overall blockchain is sometimes referred to as the "eventual consistency" algorithm.

As defined, the proof of work metric requires increasing amounts of computational effort and thus inherently consumes increasing amounts of time and computing resources, e.g., consuming electrical power and requiring special-purpose hardware. Thus, the transaction processing rate of the network, i.e., the number of transactions per unit of time, has to bear the computing load. It is well-known that Bitcoin-style networks do not provide sufficiently fast transaction rates for some types of transactions. Some calculations available in the literature suggest a transaction rate of approximately 7 transactions per second, while other calculations suggest that the Bitcoin mining network uses more than twice the amount of electricity as that used by Scotland, i.e., about 52 terrawatt hours. In contrast, the Visa network processes 65,000 transactions per second (at maximum capacity) using ½ of 1% of Bitcoin's usage. Some variants of Bitcoin such as Lightning claim much faster throughput rates by defining new kinds of transactions, e.g., by supporting off-chain transactions by setting up payment channels between pre-determined parties. New consensus algorithms such as "proof of stake", "proof of authority", etc. have been proposed to reduce the workload required to maintain the blockchain. All such consensus seeking methods use the blockchain mechanism but differ in the manner of selecting a miner node.

Thus, maintaining the consistency of the blockchain costs dearly and slows down the transaction rate to unacceptable levels for many applications.

In one aspect, the present invention is concerned with avoiding the use of blockchain to maintain consistency by providing mechanisms that allow two client devices (e.g. two applications such as wallets residing on the client devices) to transact directly with each other without being able to initiate double-spend transactions.

Since our method avoids the use of blockchain mechanism to guarantee transaction integrity or consistency, relegating the use of blockchain to an optional and asynchronously maintained record-keeper or log in certain embodiments, we save enormous amounts of electrical power. Concomitantly, two transacting devices may operate at the speed of the underlying communication network, thus improving the transaction throughput.

It is important to note that in Bitcoin-style networks, no two client devices (wallets) interact directly. All wallet interactions are indirect in the sense that interactions take place through the blockchain. That is, device to device interactions are achieved by a first client device signing a transaction (Tx) on a block of the blockchain and a second device accessing the same transaction in a subsequent block of the blockchain (cf. FIG. 2) and responding with a new transaction. As explained earlier, the two devices may sign the transactions using each other's public keys. Thus, the blockchain is the medium of interaction.

In contrast, we consider a network of inter-connected client devices (cf. FIG. 3) wherein the client devices 301 and 302 communicate directly with each other via a messaging medium. For regulatory and other reasons such as audit trails, the network may utilize a record keeper (303), but it is not mandatory in the present invention and does not lie in the "path" of the transactions. (In related work we show the utility of a ledger, e.g., in reconstructing a user's wallet who loses his client device.) It therefore does not contribute to transaction overhead. The record keeper may be updated by both the client devices at any time after the transaction between them has committed. The two client devices need not synchronize their updates of the record-keeper with each other or with the transaction process. We refer to such an updating policy as an asynchronous update of the state of the record-keeper.

As used herein, client devices (or simply "devices") refer to communication devices such as mobile phones, personal digital assistants (PDAs), smartphones, desktop computers, wearable smart devices (e.g., fitness bands, smart bandages), tablet computers, GPS devices, gaming consoles, laptop computers and transponders, which are able to communicate over one or more wired and/or wireless communication links that may or may not involve a communications network such as the Internet, Wi-Fi and Bluetooth.

As shown in FIG. 3, a central problem to be solved is for device D2 (302) to trust the transaction from device D1 (301) and ensure that D1 cannot double-spend. In subsequent discussions we show the system and methods of the present invention and use the above case as an exemplary problem.

In embodiments, the record-keeper may be implemented as a blockchain system using a miner selection metric based on proof of work or proof of stake, etc. Network designers may prefer such embodiments since the blockchain mechanism, after a decade of use, is trusted to withstand hacking and corruption attacks. As used herein, since the blockchain is not in the path of the transaction, it will not negatively impact the transaction rate of the system and cause undue workload/stress on the network's resources. It should be noted that the present invention inherently avoids the need for a blockchain system, which in all cases is discussed herein as an optional feature that may be used for recording-keeping if desired.

FIG. 4 shows one such arrangement. An especially designated node called "M" performs, inter alia, two functions described as follows.
1. Provision client devices with account balances, e.g., D1 (401) and D2 (402) so that D1 and D2 have balances B1 and B2, respectively.
2. Client devices, e.g., Devices D1 and D2, report transactional data to "M" (403) after the transaction has occurred (committed). "M" (403) may, in turn, update the blockchain (or distributed database system in some embodiments) asynchronously acting as a record-keeper (404).

In embodiments, "M" may be implemented, for instance, as software running on one or more computers, e.g., a server complex, a server farm, etc.

FIG. 5 shows an alternative arrangement wherein "M" comprises a device (501) running a computer program operating on a blockchain. The computer program may be configured to asynchronously communicate data received from devices D1 (503) and D2 (504) to the blockchain (502). It may also be configured to operate according to business logic as per the requirements of the networking application being implemented by the network. Such computer programs are often called smart contracts.

In this regard, it is pertinent to discuss certain prevalent systems that allow "off-chain" operations, in which operations involving the ledger may be deferred for a time. Such deferments usually involve "trusting" a non-mining entity to "verify" a transaction without an ironclad guarantee based on the system ledger itself. An intermediary node may issue a commit for a series of deferred transactions. However, the ultimate commitment of the system in such a case is not guaranteed and a user may not assume that the transactions have committed in actuality.

In one variation of deferred commitment schemes, the so-called payment channel method, two parties (client devices) wishing to engage in a deferred transaction, set up a payment channel in advance of the transaction. The blockchain records the "intended" transaction. At a later time, the two parties may transact the previously set up transaction. In certain embodiments, intermediate devices may facilitate the transaction by acting as proxies. Thus, nodes "A" and "C" may set up an a priori payment channel. Next, "A" may interact with node "B" and node "B", acting as an intermediary, may transact with "C".

Certain Technical Contributions of the Present Invention

The systems and methods described herein pertain to certain improvements to the technology of transaction processing systems in communication networks. Certain aspects of such improvements may be described, without limitation, as follows.

We propose technologies that support transactions between client devices in which each client device may contain a complete verifiable record of its transactions, without needing to maintain a record in a ledger-based blockchain system or other such state maintenance systems. A set of asynchronous operations may be used to update a state maintenance system, but the invention does not rely on the existence of such a system, nor does it need it in any basic manner.

Each client device may engage in one or more transactions and maintain a record of its own transactions. (A client device need not designate an intended recipient, i.e., no payment channel needs to be set up, etc.) The record so maintained may be used in conjunction with methods described herein to verify the consistency of the transaction. That is, transactional consistency may be checked locally, i.e., consistency checking may involve only the two client devices involved in the transaction. However, local consistency implies global consistency in the invention presented herein. That is, every transaction between two client devices that commits is guaranteed to be both locally and globally consistent. Consistency maintenance includes ensuring the satisfaction of the double-spending constraint.

In one aspect, certain advantages of the present invention arise from a specific type of data structure, referred to herein as a "token," which is designed to improve the way systems store, track and process data.

The present invention reduces the latency of crypto-currency networks in particular and consensus creating methods in distributed networks in general. The concomitant increase in transaction output rate will be significant and will considerably improve the usability and practicality of the technology, thus increasing its general acceptance by the public. The cost of the infrastructure supporting the distributed networks will be considerably reduced since no mining and very little hashing operations will be needed. Finally, the reduced workload of the methods presented herein will contribute to reducing the use of electrical power by the network infrastructure and thus contribute to the improvement in the carbon footprint of the overall system.

The methods of the present invention may apply not only to financial applications such as crypto-currencies, but to a variety of applications including, without limitation, messaging, email, digital content sharing, music sharing, entertainment, travel, digital wallets and credit cards, etc.

In one aspect, the systems and techniques pertain, more generally, to a communications network wherein rights and capabilities are transacted between client devices that serve as network nodes. The rights and capabilities so transacted may be maintained and verified by examining only the state of the devices involved in the transactions. There is no mandatory requirement to consult or maintain a global state maintenance system.

Furthermore, the technology presented herein is applicable to devices engaging in machine-to-machine transactions, possibly involving micro-transactional amounts, for example, autonomous cars making toll payments to roadway toll collection devices.

Basics of the Transaction Model

Client devices are used to represent users of the network, which in some embodiments are pre-provisioned with computer programs or other executable computer code that enable the client devices to transact with each other. We assume an underlying communications network that allows client devices to interact with each other, i.e. send and receive data from other client devices. Thus, each client device is assumed to have a network address, i.e., a bit string, that may be used to locate the client device.

In certain embodiments, communication protocols (e.g., I2P, TOR, etc.) may be used by a network that obfuscates the addresses of client devices. We do not discuss this aspect of the communication protocol herein and consider our invention to be independent of such technologies. That is, we assume an underlying mechanism by which two client devices may communicate with each other using addressing mechanisms that may or may not be obfuscated.

Briefly (cf. FIG. 6A), our transaction model involves two client devices in which a first client device, usually referred to as the initiating device, may initiate a transaction with a second recipient device. The initiating device requests a data item (called the commitment trigger) from the recipient device and runs a computer program to create two data structures called the token, say "T" and a first proof data object, say P1. The token "T" represents the transference of "spending rights" from the initiating device to the "receiving" device. The first proof object, P1, is meant to "verify" the successful running of the computer program effectuating the creation and transference of the token. (In subsequent discussions, we describe the terms "proof", "token" and "verify" in more detail.)

Concomitantly, the recipient device, upon receiving the request for a commitment trigger, runs a computer program to satisfy the received request and generates a second proof data object, P2, meant to verify that it generated the requested commitment trigger.

In crypto-currency applications, the token data structure represents a "spending right" that is transferred from one client device to another. As such, the token data structure will contain (in one of its data fields) the balance/amount that can be spent. Additional fields of the token data structure will contain data computed as described later.

We now explain our basic transaction model with recourse to FIG. 6B.

Notation: We denote commitment triggers by the symbol $r_{xy}$ in which the subscripts "x" and "y" denote that the commitment trigger was generated by client device "x" and sent to client device "y". Also, client devices referred to by numeric names, such as client device "1" or client device "2", etc., typically denote client devices involved in past transactions. When considering client devices involved in a current transaction, we use alphabetic names for client devices, e.g. client device "A", client device "B", etc.

Let us assume that client device "A" has concluded a (previous) transaction with client device "1". During the course of this transaction, client device "1" asked and received a commitment trigger, $r_{A1}$, from client device "A" and used it to create and send a token to client device "A". (That is, client device "A" sent a commitment trigger on request to client device "1"; the latter used the received commitment trigger to create and send a token to client device "A".)

Thus, client device "1" transferred its spending right to client device "A", represented by the token received by "A". (As will be shown later, client device "1" will lose its capability to double-spend its spending right.) Client device "A" saves the commitment trigger, $r_{A1}$, it provided to client device "1".

Thus, at the conclusion of the transaction with client device "1", client device "A" has a token received from client device "1". This token now represents the spending right acquired by client device "A". Client device "A" also has the commitment trigger $r_{A1}$ it had provided to client device "1" during the previous transaction. The token received from client device "1" has a balance representing the acquired spending right.

Let us now assume that client device "A" wishes to transfer its (acquired) spending right to client device "B". It may do so by creating a new token with a new balance (that is less than or equal to the spending right it acquired). To create the needed token, client device "A" requests and receives a commitment trigger, $r_{BA}$, from client device "B". Client device "A" may now construct the new token using its two commitment triggers, $r_{A1}$ and $r_{BA}$ with the new balance and transfer it to client device "B", representing that client device "A" has transferred a spending right to client device "B".

We thus see that, generally, our transaction model involves the transference of tokens from one client device to another, the tokens representing spending rights. To execute a transfer of spending right, a client device needs an input token and two commitment triggers in its memory that it may obtain either as a result of previous transactions or via a provisioning step, e.g., when the client device is being set up.

Having transferred a spending right, we require that the same right cannot be transferred again. As will be shown in more detail later, client device "A", when transferring the newly created token to client device "B", is required to delete the commitment trigger that it had saved during the previous transaction with client device "1". Thus, it is effectively unable to re-compute the needed output token.

Commitment Functions and Tokens

We now describe the notion of tokens further by discussing the computation that yields values that populate the token data structure. We use the words "calculate" and "compute" interchangeably in the descriptions that follow.

The token data structure depends on a type of calculation or function called a commitment. The basic idea behind the calculation is that it is easy and efficient to calculate in one "direction", but no known efficient method is known to calculate it in the "reverse" direction. Many different types of commitment functions may be defined using the notions of complexity in computer science theory. In literature, such functions are also referred to as irreversible or one-way functions.

Consider the following irreversible function F (also shown in 701 cf. FIG. 7A) that will be used in the descriptions that follow. We emphasize that the function "F" as defined herein is illustrative of a general class of functions known in the literature.

$$F(r,m) = (g^r * h^m) \bmod p,$$

where g, h and p are primes and r and m are integers. Generally, we will be concerned with calculating the value of the function F with respect to a given value of "r". We use the notation "C" to denote the value of the function F for a given value of "r". Thus, $F(r, m) = (g^r * h^m) \bmod p = C$.

Let $$F(r_1, m_1) = (g^{r_1} * h^{m_1}) \bmod p = C1,$$

and $$F(r2, m2) = (g^{r2} * h^{m2}) \bmod p = C2$$

Then $$C1 * C2 = ((g^{r_1+r_2} * h^{m_1+m_2}) \bmod p) = C12$$

Consider a client device with a known (integer) network address "m1". It is then easy and efficient to calculate C1 if we are given "r1". However, solving for "r1" requires solving the discrete log problem for which no efficient solutions are known (as is well-known in the literature). Thus, appropriate choices of g, h, m, r1, etc. give a probabilistic guarantee that C1 can only be computed in one direction, i.e., we can compute C1 given "r1", but we are effectively unable to compute "r1" given C1. In embodiments used herein, r1 and r2, etc., may be randomly generated integers and will be referred to as commitment triggers. The variables m1, m2, etc. denote integer addresses or other identifiers of the transacting client devices. Of course, more generally, any suitable parameter values may be used for r and m. More generally still, the parameters that are used as inputs to the particular irreversible function that is employed may vary from system to system. For purposes of illustration, however, the discussion herein will employ the commitment function F with the input parameters r and m as defined above.

(On occasion, in commitment calculations, in addition to the parameters C1 and C2, we define a third parameter C3 ($=F(r3, m3) = (g^{r3} * h^{m3}) \bmod p$) and then define C123 as the product C1*C2*C3.)

Exemplary token data structures are shown in FIG. 7A (702) and also in FIG. 17 as 1710 and 1720.

In the present invention, we use the computational hardness of the discrete log problem (or other such hard problems known in literature) to define the commitment function and to get a probabilistic guarantee that a computer program designed to compute the commitment function cannot be successfully executed.

As briefly described above, a transaction typically involves an initiating device and a recipient device. In such situations, the initiating device requests a commitment trigger from the receiving device.

We have used the parameter "m" in defining the commitment function F above as the address of the client device. In embodiments, commitment functions can be described without such a parameter, i.e., one may only use the commitment trigger as the parameter. Our usage of the address of the client device as a parameter herein stems from our aim to identify the client device performing the indicated calculation. To this purpose, we may alternatively use the serial number of client devices, CPU numbers, or other identifiers that may serve to identify the client device.

Additionally, we may also use the public key of the user as the value of the parameter "m" to identify the user of the client device. As is well-known, a public key can be verified by using a private key known only to the user of the client device. In such usage, the public key is encrypted using a hashing function. When verification is needed, the encrypted public key may be decrypted and verified against the user's private key.

It is well-known that certain one-way functions, such as the Integer Factorization or the Discrete Logarithm functions, are vulnerable to attacks using quantum computers. However, current literature proposes several functions that may be used in lieu of one-way functions known to be vulnerable. Examples of such functions, without limitation, are the NTRU Encrypt, Rainbow, SPHINCS, BLISS-II, New Hope, SIDH, etc. These and other such functions are postulated to be secure against attacks by quantum computers and the present invention envisions using them in calculations involving commitment functions. Details of such so-called "post quantum cryptographic functions" may be found in "Kop, Cetin Kaya (ed.), Open problems in mathematics and computational science, Springer 2014, ISBN 978-3-319-10683-0, 2014". See also, "Bernstein, Daniel, et al., Post quantum cryptography, Springer 2013, ISBN 978-3540887010".

We now turn to the question of constructing and verifying token data structures using the above exemplary transaction from initiating device "A" to recipient device "B" (FIG. 6B). As explained earlier, device "A" requests and receives a commitment trigger, $r_{BA}$, from device "B". Device "A" now computes $C_{BA} = F(r_{BA}, m_A)$ and $C_{A1} = F(r_{A1}, m_A)$ where $m_A$ is the integer address of device "A" and $r_{A1}$ is the commitment trigger it provided to device "1" from whom it acquired spending rights. Using $C_{BA}$ and $C_{A1}$, device "A" may now compute the product $C_{A1}*C_{BA}$.

The corresponding token data structure comprises the values computed above and is denoted as token(Amount, $C_{A1}$, $C_{BA}$, $C_{A1}*C_{BA}$). However, the token sent to device "B" as a part of transferring spending rights does not contain $C_{BA}$, i.e., the component value corresponding to the commitment trigger $r_{BA}$. That component value of the token is left blank and is filled in, for verification purposes, by the recipient device using its commitment trigger.

Recall that the component value $C_{BA}$ may be efficiently calculated using the commitment trigger $r_{BA}$. Without the commitment trigger, we need to calculate the discrete logarithm, i.e., we need to solve for X in $$(C_{A1}*C_{BA})/C_{A1} = F(X, m_A)$$

FIG. 7B illustrates the above description with reference to the exemplary transaction shown in FIG. 6B.

Device "1" having received commitment trigger $r_{A1}$ constructs token $T_{1A}$ denoted as $$\text{Token}_{1A} = (Amt1, C1, \text{blank}, \text{product1})$$

where "Amt1" is the amount of spending right to be transferred, C1 is the component value computed by device "1" using a commitment trigger received from a previous transaction, the missing or blank value represents the value computed using the commitment trigger $r_{A1}$ received from device "A", and product1 represents the value obtained by multiplying the latter two component values.

To verify the token, device "B" performs the function 100 indicated in FIG. 7B.

Similarly, device "A" may now use its two commitment triggers to compute $C_{A1} = F(r_{A1}, m_A)$, $C_{BA} = F(r_{BA}, m_A)$ and $C_{A1}*C_{BA}$. It may then construct the token token$_{AB}$=(Amt2, $C_{A1}$, blank, $C_{A1}*C_{BA}$) where the "blank" value represents $C_{BA}$. Device "B" may verify the received token by performing the calculation shown as 200 in FIG. 7B.

Finally, the token data structure contains a data field that, in currency applications, may be used to convey monetary amounts in a transaction. In non-currency applications, such a data field may be used to convey other types of information, e.g., in fault-tolerance applications, the data field may be used to convey the status of various components or devices in the network.

The Technology of Proof of Program Executions

In the discussion above, we briefly discussed the notions of commitment triggers and tokens and the general model of transactions. In this section, we describe the notion of "proofs" of program executions.

The technology of proof of program executions is concerned with verifying that a given program executed ("ran") with a given input and produced a given output. The execution of a computer program on a given input resulting in a given output may be said to represent a statement, viz., "the program ran on the <given input> and produced <given output>".

In one embodiment, program proof technology compiles input programs into pseudo-code and runs the latter in a suitably instrumented run-time environment. For example, programs written in a (subset) of the C programming language may be compiled into an assembler language and executed on an instrumented virtual (software) computer that supports the assembler instruction set. (Other such instruction sets, and instrumentations may be defined and are known in the literature.) A given program when executed in such an instrumented environment produces its output and a trace of its execution due to the instrumentation. The trace represents the states of the computation, e.g., contents of registers and memories of the virtual computer, values of variables, etc., as a result of the execution of the given program. To verify that the execution actually occurred, we can verify the trace to ascertain that each state follows from the previous state, resulting in the given output. Since the trace could only have been produced by the execution of the program in the instrumented environment, we may then take the trace to be a "proof" of the execution of the given program. To ensure that the trace has not been altered in any way, it may be encrypted by using encryption key technology.

In summary, proof technology is a set of methods (encapsulated in computer programs, also called software engines) that verify executions of programs. That is, a computer program runs, and a trace/record of the program is produced in such a manner that the (alleged) execution may be verified by processing the trace. The trace may be referred to as the "proof", i.e., the data object "proof" serves to verify the execution of the program. In a sense, every computer program when run on a given input and producing a certain output may be thought of as a statement, viz., the program ran on the given input and produced the indicated output. A proof of the execution of the program may then be taken to verify the statement representing the program's execution.

As a simple example, consider a program that multiples two integers to produce a resulting integer and let it accept as input the integers X and Y and produce as output the integer, Z. A proof of the execution of the program may then be taken as a verification of the statement "the program ran on input X and Y and produced output Z".

For more details, see cf. Zero Knowledge Protocols from Succinct Constraint Detection, 15 International Conference, TCC 2017, Baltimore Md., USA. Also, patent application Ser. No. 15/671,021 extends program proof technology in various ways (e.g., in producing proofs of user data privacy and sharing of content between computer programs). In the present invention, we further extend program proof technology to solve the double-spend problem in decentralized and distributed systems.

As mentioned above, the technology of proof of program executions encapsulates given computer programs in software engines. In particular, we outline three such software engines as follows (cf. FIG. 8A).

Key Generating Engine, KGE (801)
Proof Generating Engine, PGE (802)
Proof Verification Engine, PVE (803).

The engine KGE (801) takes as input an exemplary program, CP, and produces two keys as output, $P_k$ and $V_k$. The purpose of the keys is mainly to ensure cryptographic security of data objects produced as described below.

The engine PGE (802) takes the following inputs:
The key $P_K$ produced by the KGE above.
The computer program, CP, that was input to the KGE.
The input token(s) needed by the inputted computer program, CP.

PGE runs the program inputted to it with the given input token(s). The inputted program produces an output, say "output token(s)" and PGE produces a proof object, P, for the given input if it runs successfully. Otherwise, it produces an error response.

The engine PVE (803) takes as input the proof object, P, produced by PGE above, the key $V_k$ produced by KGE above, and the output token(s) produced by the computer program, CP, inputted to PGE above. It produces a "yes" response if the proof P is linked to the indicated output token(s) via the keys $V_k$ and $P_k$ (since the latter two keys are complementary). Otherwise, it produces the response "no".

In embodiments, the key(s) $V_k$ may be provided to one or more client devices in the network. In alternative embodiments, the keys $V_k$, may be provided to one or more distinguished nodes, called validator node(s) in the literature. Note that the running of the engine KGE is a one-time operation whereas PGE may be run whenever additional proofs are needed.

The general process of validation using the $V_K$ keys is as follows. As mentioned earlier, client devices represent users of the network. As these devices engage in transactions, spending rights are transferred between client devices as tokens created by specifically designed computer programs. It is essential that the tokens be validated as being produced by the specified programs. Further, that the programs producing the tokens are uncorrupted from their original provisioned form. This is accomplished by the validator nodes using the $V_K$ keys. That is, generally, a client device receiving a token representing spending rights, requests a validator node to validate the received token. The validator node uses the key $V_k$ corresponding to the received token and the engine PVE as described above.

Encapsulating Messaging/Transaction Traffic

As mentioned earlier, we use user (client) devices to represent users of the network. As these devices engage in transactions, they send and receive data messages representing the transference of spending rights. The resulting data traffic is managed in a way that the history of the transactions may be re-constructed securely as and when needed.

FIG. 8B shows an exemplary scheme wherein device "1" sends a data message to device "A" that, in turn, sends a data message to device "B", etc. The data message from device "1" to device "A" comprises of token$_{A1}$ and a proof $P_{A1}$. We create a hash of the concatenation of the latter two data objects, using a well-known hashing function such as SHA-3, etc., shown in cell number 3 of 100, FIG. 8B.

The data message from device "A" to device "B" is shown as 200, FIG. 8B. Note that message 200 contains a hash of the previous message 100.

Note also that the transaction data from device "A" to device "B" contains the proof, $P_{1A}$, from the previous transaction. Generally, transaction data from an initiating device will contain proofs of all previous transactions (except as noted later), thus enabling recipient devices to re-construct the entire proof chain. As will be shown later, this enables a recipient device to verify all previous transactions.

As will also be described later, a device may (asynchronously) update the network's record-keeper with transaction data from the transactions that the device may have undertaken. A device that has executed such an update procedure is referred to as a "synced" device. The latter may, after a sync, delete its previous proof chain since the record-keeper will contain the necessary transaction data.

In order to simplify the following descriptions, we will assume that both the initiating and recipient devices in a transaction are synced devices.

Succinct Representations of Transactions

Having briefly described messaging or transaction traffic between devices, it is permissible to describe a succinct representation of the same as shown in FIG. 9.

In 901 (cf. FIG. 9), we show an exemplary transaction from device "A" to device "B". We observe that both devices may operate independently and interact by sending data to each other. We describe the actions of each device independently below.

Device "A": Launches engine PGE with one of the programs Transfer, Split/Transfer or Merge (described later), being selected as input to the PGE. As will be seen from its specification, the selected program requests a commitment trigger, $r_{BA}$, from device "B". Next, the selected program produces a token, say T, output data "Bal" and terminates. The PGE produces a proof object, say P1. We can summarize the above actions as "device A uses the selected program and PGE to produce a proof P1, token T and data "Bal". We may represent the interactions of device "A" succinctly using the representation shown below.

Device $A[PGE/CP]\{P1\}\{T\}\{Bal\}$ where "CP" denotes one of the programs "Transfer"", Split/Transfer", or "Merge".

Device "B": Launches engine PGE with program Generate Commitment Trigger (GCT), also described later, that responds to the request from device "A" by generating a commitment trigger. GCT outputs the requested trigger and PGE produces a proof, say P2. We may summarize the actions as "Device B uses the PGE and program "GCT" to generate a commitment trigger and produces a proof, P2. We may represent the actions of device "B" succinctly using the representation below (reading from right-to-left):

$\{P2\}[PGE/GCT]$Device $B$

Combining the two interactions into a single form, we get

<Device $A[PGE/CP]\{P1\}\{T\}\{Bal\}$:$\{P2\}[PGE/GCT]$
  Device $B$> where the angular brackets "<" and ">" are used as delimiters and the colon symbol ":" separates the two individual interactions. We refer to the latter expression as the succinct representation of the interaction between the named devices, "A" and "B". It is also shown as 902 in FIG. 9.

Generally, the succinct representation above, may be described as having the form "<Interactions of initiating device: Interactions of recipient device>". The interactions of the initiating device will always involve one of the programs "Transfer", "Merge" or "Split/Transfer" that produce a proof, token(s) and output data. The interactions of the recipient device always comprise the program "GCT" producing a proof. Note that the succinct representation does not show the commitment trigger since, as will be seen, it will be deleted by design.

We remark that the above succinct notation denoting transactions is meant only for pedagogical reasons and that the actual traffic may use the encapsulations described earlier.

Trusted Execution Environments and Trusted Devices

In an embodiment of the present invention, the client devices in the communication network contain trusted execution environments (TEE) housing the computer programs described below and the data that they operate upon. A user or operating system (OS) application running in a parallel processor may trigger the housed computer programs via an API provided by the system/device. A trusted device is one that contains a TEE.

TEE is an isolated environment composed of hardware and software that runs in parallel with the operating system. It provides a trusted execution environment for computer programs, safeguarding them from software and hardware attacks. The housed programs have access to a storage area within the TEE that they may use to store and read data objects. Software and cryptographic techniques protect the housed computer programs from each other and from (OS or user) applications running in parallel processors.

As is well-known, a hardware-based root of trust is used in a TEE. Thus, an attacker needs to extract root keys from the hardware. In some implementations, extraction of the root keys via reverse engineering or via hardware probes either destroys the keys or may slow down the probing processes. In some cases, an extracted key may only work on one chip/hardware and be useless for all other chips.

TEE based computer systems and devices have been proposed and discussed in industry associations such as Global Platform and Trusted Platform Module.

In the present invention, as shown in FIG. 10A, we assume that the TEE of client devices are pre-provisioned with computer programs, token(s) and commitment triggers. That is, the TEE's processor(s) run computer programs and the data store contains tokens and commitment triggers. FIG. 10 shows an exemplary trusted device whose TEE processor is pre-provisioned with exemplary computer programs, Transfer, Split/Transfer, Generate Commitment Trigger (GCT) and Merge. These programs are further described below. The storage area of the TEE contains tokens and commitment triggers that the illustrative programs operate upon.

Running Programs in Trusted Devices

In embodiments, the client devices in a communications network are provisioned with trusted execution environments (TEE). In a provisioning step, the TEE of client devices in the network are provisioned with the keys $P_k$ and $V_k$ and with the engines PGE and PVE. In alternative embodiments, the key(s) $V_k$ may be provided to one or more distinguished nodes, called a validator node(s) in some literature. Note that the running of the engine KGE is a one-time operation whereas PGE may be run whenever additional proofs are needed.

Additionally, the TEE of client devices is pre-provisioned with illustrative computer programs Transfer, Split/Transfer, GCT and Merge.

FIG. 10B shows the general system for running one of the above illustrative programs. FIG. 10C describes the method used to run one of the illustrative programs.

In FIG. 10C, one of the programs Transfer, Merge, or Split/Transfer is selected and provided to PGE as input. PGE is also provided the input token(s) that may be needed by the selected program. The PGE runs the selected program. The selected program produces output tokens and data (if any). PGE also generates a proof data object using the trace produced by the instrumentation of the PGE. Finally, the method updates the ledger or record-keeper asynchronously.

Overview of Methods Effectuating Transactions

To illustrate the transfer of spending rights from one device to another, we present the following four illustrative programs. These programs have several features. One such feature, for example, is a solution to the double-spend problem. Other programs may also be defined that use various other features of the present invention.

1. Program "Transfer" takes inputs (Amount, $From_{Device}$, $To_{Device}$, Token) and produces as output a data object referred to as an "(output) token". As will be seen from the specification of the program, an execution of the program causes a token with "Amount" to be transferred between the indicated devices, i.e., the "from" and "to" devices. Note that the program depletes the "Amount" completely, i.e., a zero balance remains in the "From_Device" at the end of the transaction. The output "token" details, inter alia, the transferred amount. As will be further seen from the specification of the program, the program becomes incapable of repeating the same execution a second time. Correspondingly, a proof of an execution of the program verifies the statement "amount reflected by token was transferred between the indicated devices and the program cannot repeat the execution".

2. Program "Split/Transfer" takes inputs (Xfer_Balance, From_Device, To_Device1, To_Device2, token) and produces as output two data objects referred to as "token1" and "token2". The first token corresponds to the amount to be transferred to the "To_Device1" from the "From_Device". The second token corresponds to the amount that is to be transferred from the "From_Device" to itself, i.e., it is the balance that remains in the "From_Device" after the transfer to the "To_Device". As will be further seen from the specification of the program, the program becomes incapable of repeating the same execution a second time. A successful execution of the program corresponds to the statement that the program ran successfully and transferred the first token from the "From_Device" to the To_Device1" and the second token from the "From_Device" to itself.

3. Program "Merge" takes as input two token data objects and creates a single token as output. As will be seen from the specification of the program, an execution of the program causes a new token to be generated that represents the sum of the two input tokens. As will be further seen from the specification of the program, the program becomes incapable of repeating the same execution a second time. Correspondingly, a proof of an execution of the program verifies the statement "amount reflected by output token represents the sum of the two input tokens and the program cannot repeat the execution".

4. Program "GCT" takes as input a request for a commitment trigger, generates a random integer of a pre-determined size, saves the generated integer in the TEE's store, and provides the same to the requesting program. It also receives and verifies tokens and proofs.

A distinguishing feature of the above four programs (as will be explained below) is that after a first successful execution, they become incapable of a second successful execution on the same input token(s).

A malicious entity may gain access to these programs and modify them to produce a successful execution on the same input tokens by solving the discrete log problem. This is known to be extremely unlikely in the sense that it may require enormous time and computational effort due to the complexity of the discrete log problem that needs to be solved. Furthermore, the TEE will need to be compromised also since the programs reside and execute in the TEE.

A device upon receiving a proof, say P1 and token T1, may verify the proof as follows. The engine PVE (803) takes as input the proof object, P1, produced by PGE above, the key $V_k$ produced by KGE above, and the output token(s) produced by the computer program inputted to PGE above. It produces a "yes" response if the proof P1 is linked to the indicated output token via the keys $V_k$ and $P_k$ (since the latter two keys are complementary). Otherwise, it produces the response "no".

Decentralized Transactions with Asynchronous State Maintenance

In embodiments, a smart contract, i.e., a computer program, runs on one or more computers (M 1101, cf. FIG. 11) connected to a blockchain system/distributed database/record-keeper 1102. M 801 is shown as a single logical device in FIG. 11. In practice, it may be implemented as software running on a collection of servers. M 1101 is pre-provisioned with engines KGE and PGE (801 and 802, cf. FIG. 8A) and the programs Transfer, Split/Transfer, GCT and Merge. The engines KGE and PGE may be launched by user command or by an application program. These programs may then be provided any one of the programs Transfer, Split/Transfer, GCT and Merge as input.

In the descriptions to follow, we first describe a provisioning phase by which devices in the network are readied for transactions. We then describe the transactions themselves.

Provisioning Keys: M 1101 launches the engine KGE (801, cf. FIG. 8A) to generate the keys $P_k$ and $V_k$ for each of the above four programs individually and distributes them to all client devices in the network such as 1103, 1104 and 1105. As noted above, this is a one-time process. In embodiments, the $V_k$ may be provisioned to especially configured nodes of the network called validator nodes that may be used by client devices to verify transactions.

Provisioning "M" with Initial Spending Right: M 1101 will be provisioned with an initial spending right using a pre-determined amount, say "Amt". First, we provision M1101 with an initial commitment trigger, $r1_{MM}$.

Notation: Recall that the subscripts, e.g., xy, of the commitment trigger "$r_x$," denote that the trigger was generated and sent by device "x" to device "y". In the case above, the term $r1_{MM}$ denotes that the trigger generating and sending device is the same device, M.

Next, we request M 1101 to generate a second commitment trigger, i.e., $r2_{mm}$.

We calculate $C1=F(r1_{MM}, m_M)$ and $C2=F(r2_{MM}, m_M)$, where $m_M$ is the integer address of device M 1101. We now create the data structure "initial-token (Amt, C1, C2, C1*C2)", where "Amt" is the pre-determined amount of the initial spending right. Finally, M 1101 deletes its initial commitment trigger, $r1_{MM}$.

Thus, device M 1101 now possesses the spending right represented by the "initial token" and a saved commitment trigger $r2_{MM}$.

Provisioning Client Devices with Programs: In embodiments, users of the network are provisioned with trusted devices. Examples of such devices, without limitation, are smartphones, laptops, personal computers, etc. Each device contains an app, called a "wallet app", meant to provide transaction services to users. For example, the wallet apps may display the user's token balance, past transaction history, etc. The TEE contained in the trusted devices is pre-provisioned with the computer programs, Split/Transfer, GCT, Transfer and Merge (described in detail later) and the engines PGE and PVE (802, 803 cf. FIG. 8A). Recall, that in the first provisioning step above, the trusted devices are provided the keys $P_K$ and $V_K$.

Three trusted client devices are shown as A, B and C in FIG. 11; these contain wallet apps, wallet$_{803}$, wallet$_{804}$ and wallet$_{805}$, respectively. Note that initially these wallets will show a zero balance and that the devices have no spending rights (tokens). The devices also do not possess saved commitment triggers since they have not engaged in any transactions yet. We assume that the devices "A", "B" and "C" are synced, i.e., they have updated the record-keeper with all their previous transaction data.

M 1101 uses the method shown in FIG. 10C to transfer its spending right to device "A", i.e., M 1101 needs to send an appropriately created token to "A". Recall that as a result of the above provisioning process, "M" has acquired the spending right.

"M" requests "A" to provide it a new commitment trigger, $r_{AM}$. Device "A" runs the following method (cf. FIG. 10D).

Method:
Launch engine PGE with program GCT as input.
PGE runs program GCT.
Program GCT receives request from device initiating device ("M"), produces commitment trigger $r_{AM}$, and saves it in the TEE of recipient device ("A").
GCT receives token and proof from initiating device ("M") and verifies them.
GCT produces a proof object, P, as output.
Program GCT terminates.
Program PGE produces "Proof" object as output.
Ledger/record-keeper is updated asynchronously with proof object, P, (produced as output by GCT).

By running the above method, device "A" provides a commitment trigger, $r_{AM}$, to device "M". Thus, device "M" now possesses two commitment triggers, $r2_{MM}$ (as a result of the provisioning step above) and $r_{AM}$.

Device "M" now initiates the method shown in FIG. 10C that launches the program "Transfer" as input to PGE with input token, say T. PGE runs the program "Transfer" (described below). The program "Transfer" creates the token, token, comprising (Balance, $C_{MM}$, $C_{AM}$, $C_{MM,AM}$) where $C_{MM}=F(r_{MM}, m_M)$, $C_{AM}=F(r_{AM}, m_A)$, $C_{MM,AM}=(C_{MM}*C_{AM})$. Recall that $m_M$ and $m_A$ denote addresses of devices "M" and "A", respectively.

In more detail, the "Transfer" program (FIG. 12) reads the saved commitment trigger, $r1_{MM}$, from its store. If the trigger is not available, the program "Transfer" exits in failure.

Next, the program "Transfer" performs a series of calculations bracketed as "commitment calculation". In the first step of the commitment calculation, we obtain the new commitment trigger, $r_{AM}$, from device "A". In the second step, we use the commitment trigger, $r2_{MM}$, and the address of device "M" to calculate the commitment function "$C_{MM}=F(r_{MM}, m_M)$" (the function "F" is defined in 701, FIG. 7A). In the third step, we use the commitment trigger $r2_{AM}$ and the address of device "A" to calculate the commitment function "$C_{AM}=F(r_{AM}, m_{AM})$". Finally, in the fourth step, we calculate $C_{MM}*C_{AM}$.

The program is now ready to create the needed token with components (Bal, $C_{MM}$, $C_{AM}$, $C_{MM,AM}$).

The program "Transfer" now performs a sequence of steps as an "atomic" operation, i.e., the indicated steps are all performed without "interrupts" or none are performed. The sequence of steps is
Verify Balance is equal to the Amount designated as spending right
Create the token
Destroy the commitment trigger, $r2_{MM}$.

The token and proof are now available and may be sent to device "A". The outputted proof object and token object represent a verification that the program "Transfer" ran and produced the output token, i.e., that the transfer from Device "M" to Device "A" was successfully performed. (We show later that the action also cannot be repeated.)

The method of FIG. 10C updates the ledger/record-keeper 1102 (FIG. 11) asynchronously and terminates execution.

Any entity, say device 1103, can use the engine PVE and key $V_k$ (received in the provisioning steps above) to verify the received outputted token and proof object by using the PVE engine, i.e., the proof object, the received token and the key $V_k$ are input to PVE to get the response "yes". (In practice, the engines KGE, PGE and PVE and the keys $V_k$ may be provisioned under network administrator control, i.e., received from one or more administrative nodes.)

Similarly, if M 1101 does not wish to transfer its entire balance to device "A", it may use the program "Split/Transfer" to transfer a part of its balance. The working of the program "Split/Transfer" is described in detail below.

The two devices, "A" 1103 and "B" 1104, are now ready to initiate transactions since each device has tokens, i.e., spending rights. Note that device "C" 1105 does not have any spending rights and hence can only engage in receiving a transaction.

Note that the method of FIG. 10C may be used as a general method for inputting any of the four programs Transfer, Split/Transfer, Merge and GCT, to the engine PGE. The latter may then run the input program, take its output and generate a proof object that the indicated program was executed and produced the indicated output.

If now device "A" wishes to transact with device "B", we may proceed as follows. (A fuller description follows later.)

Device "A" launches program wallet$_B$ that, in turn, launches the method of FIG. 10C with program "Split/Transfer" as input to engine PGE. The program Split/Transfer outputs two tokens. The PGE outputs a proof object representing the proof that the indicated program (Split/Transfer) ran and produced two tokens.

Device "B" now has two tokens, one token that it received from device "M" (as a consequence of receiving a transaction from device "M") and the second that it received from device "A". It may consolidate the two tokens into a single token and update its state by executing a "Merge" transaction with itself.

We now describe the programs "Transfer", "Split/Transfer" and "Merge" in more detail.

The Program, "Transfer"

Recall that as a result of the provisioning steps above, devices A, B and C contain the programs Transfer, Merge, Split/Transfer, and GCT in their respective TEE. They also contain wallet apps, wallet$_A$, wallet$_B$ and wallet$_C$ (cf. FIG. 11).

We have described above the running of program "Transfer" by the method of FIG. 10C above. We now present the details of program "Transfer" with reference to FIG. 13. An exemplary purpose of the program is for device "M" to give spending rights to device "A".

Device "M" launches its wallet app that, in turn, runs the program "Transfer" which starts by reading its commitment trigger, $r2_{MM}$. (Recall that device "M" generated a commitment trigger for itself as described above.) If the latter is unavailable, the program exits in failure, implying the intended transaction cannot be executed.

Next, program "Transfer" performs the steps of the "commitment calculation" (as described above). Recall that this necessitates requesting a new commitment trigger, $r_{AM}$, from device "A". The program GCT is launched by device "A" when contacted by device "M". FIG. 14 shows the flow chart for the program GCT. If the program GCT runs successfully, it returns the requested new commitment trigger, $r_{AM}$.

Next the program "Transfer" enters an atomic phase (denoted by the square brackets). In an atomic phase, all instructions enclosed in square brackets (e.g., FIG. 12) are executed without interrupts and, furthermore, either all instructions in the block are executed or none are executed. The block in the Transfer program contains three instructions:
1. Verify that the amount of the spending right is equivalent to the balance, Bal, of the token in the store.
2. If that is the case, create a token.
3. Destroy the saved commitment trigger, $r2_{MM}$ (e.g., by clearing a portion of the memory of the TEE).

Note, the program either terminates successfully by creating the token or exits in failure. In the former case, the newly created token (and proof) is sent to program GCT that verifies the received token (and proof).

The above transaction may be described using our succinct representation (introduced above) as follows.

<Device M[PGE/Transfer]{P1}{T1}{Bal}:P2[PGE/GCT]Device A> where P1 denotes the proof that the program "Transfer" ran successfully in PGE and P2 denotes the proof that the program "GCT" running in PGE supplied the new commitment trigger and verified the received token. T1 denotes the token generated by the program "Transfer". "Bal" is produced as output data by program "Transfer".

Thus, the descriptions above illustrate the transference of spending rights from device "M" to device "A" using the program "Transfer". Similarly, device "M" may transfer spending rights to device "B", etc.

Program Split/Transfer

The operation of the Split/Transfer program may be described using our succinct notation (introduced above) as follows. Let us consider that device "A" wishes to initiate a transaction with device "B" using the program "Split/Transfer". Specifically, we consider the exemplary case (FIG. 16) wherein device "A" with balance 100G ("G" being a unit of currency) intends to transfer 5G to device "B" whose balance is, say 50G. Thus, the former's balance needs to be decreased by 5G and the latter's balance needs to be increased by 5G as a result of the transaction. By way of example, the 100G spending right of device "A" may be the result of receiving the indicated spending right from device "M" in a previous transaction. Note that, since device "A" has a spending right, it must have a saved commitment trigger from a previous transaction.

The intended transaction is modeled as a pair of transactions, split/transfer (cf. FIG. 16). In the split/transfer transaction, we split device A's balance into two parts, 95G and 5G. Next, 5G is transferred to device "B" and 95G is transferred by device "A" to itself.

That is, we wish to undertake the following transactions (using the notational representation introduced above wherein "&&" denotes atomic execution of the two transactions); also shown in FIG. 15.

<Device A[PGE/SplitTransfer]{Proof}{Token}{5G}:{Proof}[PGE/GCT]Device B>

&&

<Device A[PGE/SplitTransfer]
{Proof}{Token}{95G}:{Proof}[PGE/GCT]>

Note that we need not specify the "receiving" device in our notation when the initiating and receiving devices are the same.

In the program Split/Transfer, we calculate $C_{MA}$, $C_{AA}$ and $C_{MA}*C_{AA}$ as shown in (1720) FIG. 17. The token that is computed is shown in 1720, FIG. 17 with balance 95G. Next, we compute $C_{BA}$ and $C_{MA}*C_{BA}$. The token that is computed is shown in (1710, cf. FIG. 17) with balance 5G.

FIG. 18 shows the Split/Transfer program and FIG. 19 shows a flow chart of the same. Both figures show the computing of the two needed commitment functions and creating the two needed tokens by device "A". One token is for transferring spending rights from device "A" to device "B" and the second to itself. Note that in the case of the "Split/Transfer" program, two commitment triggers are generated (one for each token).

The Program "Merge"

The "Merge" program is shown in FIGS. 21, 22 and 23. Its succinct representation is shown in FIG. 20. In this case, we assume device B has two tokens with balances "bal_1" and "bal_2". Therefore, it must have two saved commitment triggers from previous transactions. Let device "B" have previous interactions with devices "1" and "2". Thus, it has commitment triggers, $r_{B1}$ and $r_{B2}$, respectively, saved as a result of those previous transactions.

Device "B" uses program "Merge" to do a transaction with itself, hence it generates a commitment trigger $r_{BB}$ for itself Program "Merge" creates a new token whose balance is the aggregate (bal_1+bal_2). Note that in this case, the commitment function uses three parameters. Using the succinct representation introduced above, we may describe the merge transaction as follows.

<Device $B[PGE/\text{Merge}]\{\text{Proof}\}\{\text{Token}\}\{5G\}\{50G\}$:
{Proof}[$PGE/GCT$]>

Optimization

In embodiments, the size of the data messages between two interacting devices, i.e., nodes of the network, may become large since the messages contain proof objects. To reduce the size of the messaging traffic and traffic load on the network, a policy may be instituted that requires client devices to periodically update the record-keeper. One such policy has been described earlier in the context of "synced" devices.

That is, a client device may provide the list of proofs and tokens for all its transactions along with its address serving as a unique identifier, to the record-keeper. In one embodiment, the record-keeper may generate a Merkle node from the provided data (proofs, tokens and addresses) as a special marker to the client device. An initiating device may now present the marker in lieu of its list of proofs while executing a transaction. Upon receipt of a marker, the receiving device may provide the address of the client that sent the marker along with the marker to the record-keeper who may verify the provided data elements using the well-known mechanism of Merkle trees.

Note on Asynchronous Updates

We have previously described the use of commitment triggers and that, if a trigger is unavailable, the ensuing computer program to compute it may require enormous time and resources. Now, as described above, after a transaction is executed, the initiating device executes an asynchronous update of the record-keeper or ledger. We propose that the asynchronous updating method be designed to effectuate the update within a pre-determined time after the conclusion of the transaction. Thus, a malicious attempt to compute the commitment trigger will be time-constrained.

Lost Devices or Loss of Network Connectivity

The following possibility with respect to FIG. 10C and elsewhere should be noted. It is possible that after step 5 has been executed and before step 6 has been initiated or finished, one or both of the devices engaged in the transaction may be lost or malfunction or lose network connectivity, etc. Thus, the transaction would be completed as far as the devices are concerned but the log may not be updated. We resolve this situation as follows.

In embodiments, we require that if two devices, say "A" and "B" are engaged in a transaction, we locate one or more devices, called proxy devices. The number of proxy devices so located may be pre-determined or the number may be a function of the amount of the transaction being executed between devices "A" and "B". The number of proxy devices may also be determined by a system or user stated policy.

Once the required number of proxy devices have been located, "A" and "B" may executed the transaction and provide an update to the one or more proxy devices in an atomic operation. That is, with respect to FIG. 12 (by way of example), the atomic operation in step 7:

7. [Verify Bal==Amount && Create and output token= (Bal, $C_{MM}$, "blank", $C_{MM,AM}$) && Destroy $r1_{MM}$] is replaced by a new step 7 and an additional step number 8 is added as follows.

new step 7. Locate proxy devices. If required number not found, exit.

Additional step 8. [Verify Bal==Amount && Create and output token=(Bal, $C_{MM}$, "blank", $C_{MM,AM}$) && Destroy $r1_{MM}$ && update proxy devices]

Thus, in case device "A" and "B" are lost or malfunction, the proxy devices may be requested to update the log. For example, having received an update, a proxy device may periodically check the log and ascertain that a corresponding update has been done. If, after a pre-determined amount of time, no such update is detected, the proxy device may effectuate the updating of the log.

The systems and methods described herein may be used in a wide variety of applications other than the currency applications described in detail above. For instance, in addition to a currency value or a spending value, the systems and techniques described herein may be used in transactions involving, without limitation, credentials, property rights, status information, real estate, insurance, health care, music and other royalties, and so on. That is, more generally, the systems and techniques described herein may be used to transfer the value of any state between client devices. Such states may specify or otherwise involve, without limitation, financial data, public and private records, identification, attestation, loyalty points, electronic coupons, smart contracts, escrow records, and so on.

Towards this goal, we consider a fault-tolerance application in which various components of the network report their status to a log or record-keeper. One or more entities may then peruse the log to discern the status of the components. It is required that no inconsistent status information be communicated to the log.

To use the methods of the current invention in this application, we may modify the "Transfer" program as follows.

We use the data field of the token data structure computed by the "Transfer" program to encode the status of a device. For example, the status information may indicate that the device is functioning normally or malfunctioning. A device with such a suitably modified program may then be programmed to execute a transaction resulting in the transaction data being logged in the record-keeper.

To execute a transaction, a device needs to be provisioned with a spending right and the suitably modified "Transfer" program. To this purpose, we may use the M-device 1101 of FIG. 11 to provision network devices with spending rights and the modified "Transfer" program. (In the context of the current fault-tolerance embodiment, it may be more appropriate to refer to the spending right as a "communication right".)

Having been provisioned with a communication right and the suitably modified Transfer program, a device may use the latter to execute a transaction with itself. Such a transaction will cause the transaction data to be recorded in the log. If the device is programmed to periodically undertake such transactions, the corresponding log entries will then contain the history of the device's status. As a consequence of a transaction, the device's spending/communication right is effectively renewed.

Further note that if a malicious entity modifies a device's "Transfer" program, the ensuing transaction undertaken by the device will not be verified as per the program proof process described earlier.

Thus, a consistent view of the current and historical status of the network's devices may be obtained from the log's records.

Non-Trusted Devices

We now consider an embodiment in which the user client devices do not contain a Trusted Execution Environment (TEE), i.e., the devices are non-trusted. A problem with a non-trusted device is that malicious entities may gain access to the data and programs, e.g., proofs, tokens, commitment triggers, etc., stored in its memory registers. Thus, the usual problems of double-spending etc. may occur.

To ensure consistency of underlying transactions, we propose using an immutable record-keeping technology of which a blockchain ledger is one example. Another example is provided by the technology of distributed databases with concurrency control software.

Consider an exemplary transaction between an initiating non-trusted device "A" and a recipient non-trusted device "B" (24100, cf. FIG. 24). To effectuate the exemplary transaction 24100, we use the transaction model utilizing the M-device of FIGS. 4 & 5 and depict the model as in FIG. 25.

That is, the exemplary transaction 24100 of FIG. 24 is effectuated by implementing transaction 25200 followed by transaction 25300 shown in FIG. 25. Note that 25200 is a transaction from device "A" to M-device and 25300 is a transaction from M-device to device "B". Further, we require that 25200 and 25300 update the ledger atomically. Conventionally, this type of transaction structure is called a "two-legged" transaction model.

Specifically, with respect to FIG. 10C, steps 5 & 6 are modified as follows.

New step 5: [Output proof and data & tokens, if any
&&
New step 6: Update ledger/record-keeper to record output proof and data & tokens, if any]

where, as previously described, the square brackets and the "&&" operator indicate that the enclosed transactions are to be executed atomically.

Further, with respect to FIG. 10D, steps 6&7 are modified as follows.

New step 6: [GCT produces proof object "proof" as output
&&
New step 7: GCT updates ledger/record-keeper to record proof]

However, the method described above does not adhere to the principle of decentralization commonly accepted in cryptographic transactions. That is, we have presumed that M-device of FIG. 25 acts non-maliciously. In cryptographic transaction systems, trust is typically placed on a collection of devices (from which one device is selected using an openly described method such as "proof of stake") and not on a single device.

We propose to resolve this issue by using three different embodiments A, B and C as follows.

1. [Embodiment A] We select a group of devices and collect them into a group called the mining group (MG). (The group formation method is described below.) To effectuate transaction 25200 (cf. FIG. 25), the M-device 25400 receives the transaction and submits it to the MG group. One of the members of the MG group is selected (using a method described below) to record the transaction in the blockchain 25600. Next, the M-device initiates transaction 25300. Device "B" requests a mining group to be formed and submits an update request to the group members. A member device is selected to perform the requested update of the blockchain.

2. [Embodiment B] We select a group of devices and collect them into a group called the mining group, MG. We replace M-device 25400 (cf. FIG. 25) with one of the member devices of the MG group, say device X, and use the latter, in lieu of the M-device, to act as the intermediate device, i.e., device X receives the transaction 25200 and updates the blockchain 25600. Subsequently, it also initiates the transaction 25300 to non-trusted device "B". At the conclusion of transaction 25300, device X updates the blockchain 25600.

3. [Embodiment C] We select a group of devices and collet them into a group called the mining group, MG. We replace M-device 25400 (cf. FIG. 25) with one of the member devices, say device X, of the MG group and designate the remaining members of the group as MG'. We use device X, in lieu of the M-device, to act as an intermediate device. To effectuate transaction 25200, device X receives the transaction and submits it to the MG' group members (i.e., the group of devices excluding itself). The MG' group members now select one of their member devices to record the transaction in the blockchain 25600.

We now describe the methods used to form the mining group MG and to select one of its members and then describe embodiments A, B and C in more detail.

Mining Group

We introduce the notion of selecting a group of devices that have registered in the transaction network. We then select one of these devices in such a manner that collusion becomes difficult. Conventionally, devices performing such functions are referred to as miners. The miners may be dedicated servers. Alternatively, or in addition, the client devices themselves (i.e., the devices that perform transactions) may be used as miners in the mining group. Members of the mining group engage in a conventional consensus method such as a "proof of work" or "proof of stake" method. The purpose of these methods is to allow one of the member devices in the group to be selected and the selection method to be unbiased and rule out collusion and malicious devices. These methods have been described earlier and are known in the art. If client devices are used as miners, a proof of stake method will generally be preferable because of the reduced processing and power resources that are required in comparison to proof of work methods.

A subset of all the potential miners are selected to perform the mining in any given transaction. This subset of miners is referred to herein as the mining group. The members of the mining group for any given transaction may be selected in accordance with the Group Formation Method described below.

For convenience, in some embodiments each client device in the network may be associated with a particular segment of the blockchain, the segments of the blockchain being logical partitions based on geographical criteria (e.g., in the US, we may have one segment for client devices registered on the East Coast and another segment for client devices registered on the West Coast). When conducting a transaction, the miners that are selected only need the segment of the blockchain with which the transacting client devices are associated.

Mining Group Formation Method

We introduce a notion of group diversity that is used to select those registered devices that can be included as members of a mining group. That is, members are selected using criteria that attempts to ensure that a diversity of miners are selected so that the likelihood of collusion between miners is minimized. To that end one criterion that may be used is the amount of spending rights in the possession of a potential member since the greater the amount, the more the potential miner has at stake and hence the greater the potential miner's interest in protecting the integrity of the system. Other criteria that may be employed include the amount of the proposed transaction, the number of times the potential member was chosen in the past "N" transaction requests (where "N" is a network parameter determined by system administrators), and the segment of the blockchain to which the potential member belongs (members may be selected from the same segments as the client devices involved in the transaction, from different segments or they may be selected from multiple segments). Any combination of these and other parameters may be used to calculate a group diversity metric that is used to select the members of the mining group. The group diversity metric may be, for instance, a weighted average of the selected parameters.

System administrators may set minimum and maximum size of mining groups.

Mining Group Member Selection Method

Members of the mining group perform the "proof of stake" method to select a member to atomically update the blockchain.

Using the Mining Group in Embodiments A, B and C

[Embodiment A]: To effectuate transaction 25200 (cf. FIG. 25), we proceed as shown in FIG. 26. Client device "A" initiates a transaction Tx(1) with M-device. The latter requests a mining group 26400 to be formed using the group formation method described above. M-device submits an update request to the mining group 26400. The mining group selects one member using the member selection method described above to perform the requested update of the blockchain. This completes the first leg (26200) of the transaction.

To effectuate the second leg (26300) of the transaction, M-device initiates a transaction Tx(2) with device "B". The latter requests that a mining group 26500 be formed using the method described above. Once the group has been formed, device "B" sends an update request to all members of the group. The group 26500 selects one member, using the method described above, to perform the update of the blockchain.

[Embodiment B]: To effectuate transaction 25200 (cf. FIG. 25), we proceed as shown in FIG. 27. Client device "A" requests (101) formation of a mining group, MG. Illustrative criteria that may be used to select the members of the mining group MG has been discussed above in connection with the Group Formation Method. One device is selected (102) from the group, MG. The method of selection has been described above. Let the selected device be designated as "device X".

Client device "A" initiates a transaction (103) Tx(1) with the device X. We may refer to this as the "first leg" of the transaction. Device X requests (104) an atomic update of the ledger 27600 to record all elements (e.g., proofs, data, tokens) of the transaction from client device A to device X.

Continuing with embodiment B, we turn to the second leg of the transaction (cf. FIG. 28). Device X initiates a transaction (101) with client device "B". At the conclusion of the transaction, device X requests (102) an update of the ledger to record the second leg of the transaction.

[Embodiment C]: To effectuate transaction 26200 (cf. FIG. 26), we proceed as shown in FIG. 29. Client device "A" requests (101) formation of mining group MG. The group is formed using the group formation method described above. A member of the group is selected (102) using the member selection method described above. Let the selected member device be designated as "X". Next, the client device initiates a transaction (103) to the X device, which in turn requests a blockchain update (104) from the group MG'. Recall that MG' comprises of devices that belonged to the group MG except the device "X". The group MG' uses a proof of stake method to select a member that performs the requested update (105) of the blockchain. This completes the first leg of the transaction.

To complete the second leg of the transaction, we proceed as shown in FIG. 30. Device X initiates a transaction (101) with device "B". The latter requests a blockchain update (102) from the group MG'. A member device of MG' is selected using the method described above, i.e., the proof of stake method. The selected member device performs the requested update (103) of the blockchain.

In general, the selection of devices to be included in the group of miners and the selection of an individual member of a mining group to update the ledger or to serve as the intermediary device may be performed in different entities in different embodiments. For example, in various embodiments the system administrator, the transacting devices, or the potential miners themselves may make these selections.

Network-Initiated Transaction Model

The embodiments discussed above have used a transaction model wherein transactions are initiated by a client device that may be a secure device (device possessing a trusted execution environment) or a non-secure device (device not possessing a trusted execution environment). We now present an embodiment wherein the network initiates a transaction.

In general, some transactions may require special handling and, e.g., enterprises may impose requirements to be observed by the various actions undertaken by transactions. For example, transactions involving the purchase of certain goods may need to contain steps that include taxation elements. Furthermore, the amount of tax may vary based on the goods being purchased. Likewise, a recipient of a transaction may require that the initiating party submit a signed document, e.g., an invoice, along with a payment amount, for the former to accept the transaction.

As shown in FIG. 31, one or more servers may be configured to provide custom business logic that specifies the various rules and conditions that need to be observed by a transaction of a certain type. That is, transactions may be distinguished by type and rules and conditions may be specified that apply to the various types of transactions. In a provisioning step (101), the M-device (31200), which may or may not be a trusted device, may be provisioned with the rules and conditions, i.e., the custom business logic, for one or more types of transactions.

M-device 31200 may now be triggered (102) to initiate a transaction. The trigger may emanate from a third-party device or from one or more client devices registered in the network. For example, a third-party server may be configured to provide a trigger on a periodic or timely basis to the M-device, e.g., on the first day of the month. Alternatively, a client device, e.g., device "A", contemplating a transaction with a device "B", may provide a trigger to the M-device. Recall that client devices may be secure or non-secure.

A trigger to the M-device distinguishes or specifies a type of transaction. Thus, the M-device, upon receiving a trigger, may be configured to identity a particular custom business logic. In embodiments, the M-device may now create a computing environment in which the identified business logic runs and which, in turn, may trigger one or more client devices to execute a transaction, as per the dictates of the business logic.

As shown in FIG. 31, M-device (31200) may identify, e.g., custom logic L1, and run the latter in a specially configured computing environment 31600. (For example, the computing environment 31600 may be configured for security reasons to only allow authorized, e.g., cryptographically signed, logic to be executed. In embodiments, a virtual machine technology or a "sandbox" may be employed to configure environment 31600 as is well-known in practice.) The logic L1 may then instruct devices "A" (31300) and "B" (31400) to engage in a transaction (103 and 103'). The devices "A" and "B", in turn, may contain service logic that ensures that the dictates of the logic L1 are observed. For example, devices "A" and "B" may contain service logic that computes the proper tax amount to be included in the proposed transaction executed between devices "A" and Thus, client devices "A" and "B" may engage in a (network initiated) transaction (104). The trigger for initiating the transaction may emanate from one or more client devices (registered in the network) or from external third-party servers. Note that the specific operations of the transaction are controlled by the service logic in the respective devices that, in turn, is controlled by the custom logic, e.g., L1, in the M-device 31200. The latter may be provisioned by one or more provisioning servers 31100.

User Identity

The embodiments described so far are concerned mainly with spending rights. We now discuss other kinds of rights, e.g., rights associated with identity and producing and consuming information.

To summarize the methods described above, consider the situation shown in FIG. 32.

M-device (cf. 1101 FIG. 11), acting as a Key Generating Engine, KGE (cf. 801, FIG. 8A), when provided with a computer program CP as input, produces two keys, a proving key, $P_K$, and a verifying key, $V_k$. The M-device may then provide the proving key, $P_K$, to a user device, 2402, along with the computer program, P. It may also provide the verifying key, $V_k$, to a validating device/node, 2404.

Using the program CP and a dataset X as inputs, device 2402, acting as a proof generating engine, PGE (cf. 802, cf.

FIG. 8A), may produce two outputs, an object called the proof, P, and a dataset called the token, T. Device 2402 may now transmit P and T to a second user device, 2403.

In turn, Device 2403 may transmit the received data objects, P and T, to validating device 2404 that, acting as a proof verification engine, PVE (cf. 803, FIG. 8A), may verify the relationship between the input dataset X and the output dataset T as being captured by the proof, P. Furthermore, as stated before, the verification also ascertains that the computer program CP was used to generate the proof P and that the former remains unchanged from its original form as presented to the KGE.

General Description of the Method (cf. FIG. 32).

Input computer program CP to M-Device acting as KGE.

KGE generates keys $P_k$ and $V_k$. Transmits the latter to the Validating Node 2402 and the former to user device 2402. (In embodiments, KGE may also transmit computer program CP to 2402.)

User device 2402, acting as PGE, generates proof object P and output token T; both are transmitted to user device 2403.

User device 2403 transmits a verification request to Validating Node/PVE 2404. The latter, acting as a PVE, proceeds to verify the incoming request and responds with "yes/no" to user device 2403 accordingly.

In embodiments, 2401 & 2404 may be implemented on a single computer or on or on one or more computers. Also, 2403 & 2404 may be implemented on a single computer or on multiple computers. Different enterprises may operate 2401 & 2404.

In the descriptions above, various embodiments of the computer program, CP, have been shown, e.g., the programs Split/Transfer, Transfer, Merge, etc.

In the present embodiment, we consider different forms of the input computer program, CP. In particular, consider the well-known collection of computer programs that has been released in the public domain by many Internet service providers that process biometric data (e.g., facial, fingerprint data), recognize features in this data (such as whorls in fingerprints and facial features in photographs) and create output datasets of such features. Computer programs are also available that process image data, e.g., by scanning consumer driver licenses or other user credentials. By way of examples of the general availability of such computer programs we list the following.

Websites operated by Amazon, Trueface, Animetrics and Skybiometry list computer programs (or their APIs) that process facial images of consumers and are available to the public. The vendor "IDscan" provides computer programs to process consumer driver licenses.

Furthermore, as shown in (cf. System and Methods for Sharing and Trading User Data and Preferences Between Computer Programs and Other Entities While Preserving User Privacy, U.S. application Ser. No. 15/475,748, which is hereby incorporated by reference in its entirety) such computer programs may be used in the Proof of Program Executions technology, i.e., using KGE, PGE and PVE engines, to produce credentials denoting user identity.

The functioning of the FP class of programs may be described as follows. When fingerprint data is input to such a program, it may produce as output a matrix of (gray scale) image intensity data that, in turn, may be converted into a matrix of integer values. It has been reported that such matrices may have e.g., 1000×1000 values. In turn, such matrixes may be further processed to identify features in the image intensity data. For instance, if the image intensity data represents fingerprints, features such as whorls, ridges and the like may be identified. Such features may themselves be stored in new feature datasets. It is expected that two different fingerprints, when input to such a computer program, will produce distinguishable feature sets. This distinguishability aspect is currently the basis by which many smartphones use fingerprint data to authenticate users. Similar observations may be made about the class of commercially available programs that process facial or other biometric data.

We now observe that by using suitable computer programs in conjunction with the general method described above, we may achieve the capability of generating user identity credentials and verify the same as needed. The method comprises two phases. We describe this embodiment as follows.

Phase 1.

A computer program CP is selected that takes as input biometric data of a user. For example, it may accept the user's fingerprint data as captured by a fingerprint scanner implemented on a smartphone. (In practice, the computer program CP may be available publicly or may be developed using commercially known techniques.) In a provisioning step, we input the selected computer program to M-device 2401 (cf. FIG. 32), which acting as a KGE produces the keys $V_k$ and $P_k$. The key $P_k$ is transmitted to user device 2402 along with the computer program CP. The key $V_k$ is transmitted to the validating node 2402.

User device 2402, acting as a PGE, launches the computer program CP that, in turn, requests the user to input his fingerprint dataset and processes it to produce an output token, T1, the feature set corresponding to the input fingerprint dataset. It also produces a proof object, P1, indicative of the action that the program CP ran to produce T1 from the input dataset. The object T1 is transmitted to the validating node 2404, which stores the object T1 for later use. (In some embodiments, the object T1 may be encrypted and digitally signed.) This completes the setup phase of the method.

Phase II

In this phase, a consumer using device 2402 wishes to authenticate himself/herself to another device, say 2403. The latter may be a user device or a website, etc.

Consumer initiates the software engine PGE on his device 2402. Note that, in practice, the engine PGE may be encapsulated in an application. PGE launches the computer program CP (made available to it in phase 1 above) that requests the consumer to input his fingerprint data. The program CP proceeds to process the input data and produces output token object T2 and proof object P2. Both P2 and T2 are transmitted to the device 2403.

Device 2403 receives the objects T2 and P2 and transmits them to the validating node 2404 as a part of a verification request.

Device 2404, acting as PVE, verifies P2 using the previously received key $V_k$. Furthermore, it ensures that T1=T2. Recall that both T1 and T2 represent feature sets derived from fingerprint datasets. Hence, this comparison involves comparing two groups of feature sets. If the comparison of Ti and T2 succeeds and the verification of P2 succeeds, PVE returns "true/yes" to the device 2403. Else it responds with "false/no".

In some embodiments, the object T1 may be transmitted to a blockchain system for storage. In such a case, the validating node 2404 needs to access the blockchain system to perform its comparison operations. Alternatively, the object T1 may be stored in the user device 2402 in which case the comparison between T1 and T2 needs to be performed by the user device 2402.

We have thus shown in this embodiment that a consumer may create an identity credential and use it to authenticate himself to a third party that may use an independent validating node to achieve the authentication.

In previously described embodiments we have shown that a consumer may generate a token representing spending rights.

We now observe that a consumer may wish to encapsulate a spending right token and a user identity token into a single new token that may be referred to as a composite token. Such a composite token may then be transmitted to, e.g., a vendor, that may, based upon the result of a successful verification of the composite token, may trust the latter to represent a payment from an authenticated user.

Since, in general, the computer program CP may be representative of a variety of computer programs, we may use the above method to create a variety of credentials for consumers. For example, a computer program may scan the data on a driver license of a consumer and extract age and address information. Such a program may then be used to create credentials a la the user identity credential. We may then refer to such credentials as "age" and "address" credentials.

Furthermore, we may then create composite tokens that comprise payment, identity, age and address components. Such tokens may then be presented to vendors that may use them, after successful verifications, as satisfying their compliance and tax regulations. For example, many states in the US require proof of age and residence in order to sell alcoholic beverages to consumers. Sports gaming websites require proof of age and residence, etc.

The use of composite tokens requires additional technology for proper implementation. It is important to note that a vendor, upon receiving a composite token, say comprising payment and identity components, needs to not only verify the identity and payment components individually, but it also needs to verify that the two components were collected or encapsulated together into the same token. Otherwise, a malicious entity may use an identity component from a first person and a payment component from a second person to gain the trust of the vendor.

To achieve this verification, the user device 2402, acting as a PGE, needs to not only construct a proof, say P1 for the payment component, proof P2 for the identity component, etc., but it also needs to create a third proof, say P3, representing the combining of the two (or more) components into a single token.

That is, a new computer program is needed that performs the functionality of each of the three programs CP1, CP2 and CP3 described in the following.

Computer program CP1 processes consumer fingerprint data to produce token Ti representing feature sets of consumers.

Computer program CP2 processes consumer spending right data to produce payment token, T2.

Computer program CP3 encapsulates T1 and T2 into a token T3.

In some embodiments, CP3 may be constructed so as to contain CP1 and CP2 as sub-routines.

We may now modify the above general method to input a computer program CP having the functionality of computer programs CP1, CP2 and CP3 to device 2402 that, acting as a PGE, generates three proofs, say P1, P2 and P3, (along with the corresponding tokens T1, T2, T3) representing an identity token, a payment token and a composite token comprising the identity and payment tokens, respectively.

FIG. 33 shows an example composite token with payment and identity sub-components. Note that in an embodiment, a visual rendering of the token on a display screen may be configured to display the token, with each component being separately identified by text and/or some other visual identifier. For instance, as shown in FIG. 33 the composite token may be visually represented as a "coin" (or currency note) with two different regions representing the two different components of the token. The different regions may be distinguished and identified using text, different colors, shading, etc. In some embodiments each region, or a portion of each region, may be configured as a hyperlink that points to the corresponding proof for that component. The proofs, in turn, may be linked to the validating device for verification purposes.

In some embodiments, the composite token may contain more than two components. Furthermore, while the illustrative composite token discussed above included a payment component, in some cases the composite token need not contain a payment component. For instance, depending on the particular application in which the composite token is being employed, it may only contain, e.g., two or more identity tokens. For example, a composite token may contain an identity credential component based on the user's employment ID card and another identity credential component based on his driver license. Of course, in yet other embodiments the composite token may contain components other than, or in addition to, payment and identity components Tokens Encapsulating Information Rights In another embodiment, a user may wish to share information with another party and include with it user credentials that allows the user to verified without revealing the underlying identity data of the user. In this way the user's privacy can be maintained. For instance, a consumer may wish to submit a review, i.e., an opinion piece, about some issue or subject. We may provision the PGE with a computer program, say CP, to which the user may provide his biometric dataset and his review to the PGE as input. The computer program processes the user's biometric data and review data or other information and produces a token object comprising the contents of the review and a proof linking the identity information of the user to the review.

In this manner, a consumer may establish credibility in his posting since the underlying biometric dataset acts as a sort of "biometric" signature. As described above, the user's (biometric) data is not revealed, i.e., we may only verify that a user, known to the website, is the author of the posted article. That is, the identity of the author has been verified by the website.

Thus, by encapsulating information about themselves in one or more tokens, consumers may enhance their credibility with vendors, third parties and other consumers.

The techniques described in the previous section are not limited to use in datasets pertaining to identity information. Consider, by way of example, an input dataset containing a user's date of birth. For instance, a user may provide his driver license as input to a computer program that extracts, using image analysis techniques, the user's date of birth. Using knowledge of the current date, the computer program may be able to ascertain that the user is more than 18 years old. It may thus generate an output (e.g., age is greater than 18).

When fed as input to the PGE engine, we may therefore produce a proof from the input date of birth demonstrating that the user is more than 18 years old. Furthermore, the proof may be verified by a third-party device possessing the corresponding verifying key. That is, the PGE may output a token T representing that the age if the consumer is greater than 18 and a proof object that may be used by a third party to issue a verification request to a validating node. Upon successful verification, the third party may trust the user as satisfying the asserted "age" credential.

Method to Create "Age" Token (cf. FIG. 32)

Assume we have a computer program to process a consumer provided data object containing date of birth data (e.g., driver license, birth certificate, etc.)

Input program CP to device 2401.

Device 2401 derives keys $P_k$ and $V_k$. Sends the latter to validating node and the former to device 2402. (In embodiments, 2401 may also send computer program CP to 2402.)

Device 2402, acting as a PGE, derives token, T, representing "age" and a proof, P, using program CP. Device 2402 sends T and P to device 2403.

Device 2403 issues verification request to validating node 2404.

Device 2404 verifies request using previously received V_k and the token and proof object obtained from the incoming verification request.

If verification succeeds, device 2404 responds with "True/Yes"; otherwise it responds with "False/No".

Any number of computer programs may be written for processing data for different purposes and when used in the PGE engine they may produce proofs derivable from the input user data, e.g., user lives in the state of New Jersey, user is more than 18 years old, etc. In some cases the input data may be obtained directly from the user's client device. For instance, the input data may be obtained from one or more sensors (e.g., GPS, temperature, camera, accelerometer) incorporated in or associated with the client device. For instance, a consumer's current location may be converted into a credential using the consumer's smartphone containing a GPS location sensor. A computer program running on the smartphone reads the GPS sensor data, processes it and may then use the PGE to produce a proof and a token, the latter representing the current location of the consumer.

Furthermore, we may encapsulate one or more of these proofs along with the corresponding output of the PGE into a single token with multiple components. For example, we may have a single composite token that contains a payment component, a state of residence component and an age component. Such a composite token may then be used to satisfy purchase requirements of different vendors, e.g., a website selling alcoholic drinks may require age and state of residence proofs to satisfy its compliance requirements.

FIG. 34 shows an example of a composite token comprising of four (4) component tokens, representing the payment (spending right) token, an identity token, an age token and a state of residence token. Note that in an embodiment, a visual rendering of the token on a display screen may be configured to display the token as a "coin" (or currency note) with four different regions, possibly denoted by different colors or other indicators, representing the four different components of the token.

Linked Tokens

We now consider the case of a vendor who receives a (composite) token, T1, comprising of two components, (T11,P11) and (T12, P12), where T11 denotes the output of PGE and P11 denotes the proof object outputted by the PGE, etc.

$$T1=[(T11,P11),(T12,P12)]$$

The vendor now creates a second token with components (T21, P21) and encapsulates T1 into the former:

$$T2=[(T21,P21),T1]$$

We refer to such tokens as linked tokens, i.e., tokens T2 and T1 are linked. In a sense, linked tokens contain composite tokens as sub-components.

To illustrate the utility of such a scheme, consider a restaurant that maintains a website. The latter allows patrons to write reviews of the restaurant, e.g., quality of the food, service, ambience, etc. We wish to ensure that the website shows all reviews, i.e., that no reviews can be (selectively) deleted by the website.

When a first user requests the website that it wants to write a review, the latter sends it a linked token that contains all the previous tokens submitted by various users. The first user now writes his review, creates new token components (proof and output of PGE), possibly containing his identity and other information, e.g., location, and inserts his new components into the received linked token. Thus, the linked token now contains the components of the first user along with the tokens of all the previous users who may have submitted reviews.

The website may now publish the linked token as it contains all the reviews and no review component may be deleted since the resulting altered token will not be verifiable.

FIG. 35 shows an example of a linked token containing multiple review objects submitted by different users acting as reviewers. A visual rendering of the linked token may be displayed on a webpage as shown in the figure.

It should be noted that in some cases it is possible that the double spend problem addressed above by the use of the commitment trigger mechanism and irreversible functions will not arise. For instance, the double spend problem may arise in situations where a token does not include a payment component. Accordingly, in these cases the use of the techniques described herein for overcoming the double spend problem may not be necessary. Nevertheless, even in these situations these techniques may still be employed, if desired.

Additional Embodiments

In the above discussion we have considered the operation of the Key Generating Engine (KGE), the Proof Generating Engine (PGE) and the Proof Verification Engine (PVE). As presented above, the KGE, PGE and PVE can be implemented in various physical devices generally referred to as communication devices. We now consider implementations of these three engines in various physical devices and discuss some illustrative use cases emanating from such implementations. We point out that the use cases discussed below are for illustrative purposes and various choices of implementations begat many more use cases.

We summarize the engines and the choice of physical devices as follows.
1. The engines are KGE, PGE, and PVE.
2. These engines may be implemented on one or more communication devices.
3. When a communication device implements the PGE, it gains the capability to create and send tokens, i.e., it may act as a Sender that is able to send (i) information embodied in tokens or other data structures and (ii) one or more proofs that are associated with the data structures and which can be used to verify the accuracy of the proofs.
4. When a communication device implements the PVE, it gains the capability to verify the data structures, i.e., it may act as a Verifier.
5. A communication device does not necessarily need to implement the engines KGE, PGE or PVE to act as a Receiver that receives the data structure.

FIG. 36 shows a simple table listing the various engines and the roles played by physical devices.

Without limitation, some realizations stemming from the above choices are as follows. All collections of communication devices comprise one or more communication devices.

A. In one realization, the KGE is implemented on a first collection of communication devices. A second collection of communication devices implement the PVE and acts as Verifiers in transactions. A third collection of communication devices implements the PGE and acts as Senders in transactions. One or more third-party communication devices act as Receivers. All physical devices are inter-connected by one or more (private, public, wired, wireless or any combination thereof) data communication networks. FIG. 37 shows physical devices and their implementations as follows. Device 201 is a trusted third party that implements the KGE. Device 202 implements the PVE and acts as a Verifier. Device 203 acts as a Receiver. Device 204 implements the PGE and acts as a Sender. This realization uses 4 collections of devices, viz., devices 201, 202, 203 and 204.

B. In another realization, the KGE and PVE are implemented on a first collection of communication devices. The PGE is implemented on a second collection of communication devices which acts as a Sender in a transaction. Members of the first collection of communication devices that implement the PVE act as a Verifier. All physical communication devices are inter-connected by one or more (private, public, wired, wireless or any combination thereof) data communication networks. FIG. 38 shows the physical devices and their implementations. Device 301 implements the KGE. Device 302 implements the PVE and acts as a Verifier. Device 301 also acts as a Receiver. Device 303 implements the PGE and acts as a Sender. This realization uses three collections of physical devices, viz., devices 301, 302, and 303.

C. In yet another realization, the KGE is implemented on a first collection of communication devices. The PGE and PVE are implemented on a second collection of communication devices which act as Senders, Receivers and Verifiers. All physical communication devices are inter-connected by one or more (private or public) data communication networks. FIG. 39 shows the physical devices and their implementations. Device 401 implements the KGE. Device 402 implements the PVE which enables it to act as a Verifier. It also implements the PGE which enables it to act as a Sender. Lastly, it acts as a Receiver. This realization uses 2 collections of devices, viz., 401 and 402.

We now present some illustrative examples, without limitation, of the above embodiments A, B & C.

Example(s) Arising from Embodiment A:

An enterprise, say ACME, is interested in ensuring that its employees are tested for some personal characteristic such as whether they have or had a disease or infection. In this example ACME may only allow an employee to report for work if their tests are negative, e.g., only non-infected employees are allowed entry to the enterprise premises.

Enterprise ACME implements the engine KGE on its communication device(s). ACME provisions the user communication devices of its employees with the proving keys $P_K$; these user communication devices implement the PGE and play the role of Sender in a transaction. ACME provisions a second collection of communication devices with the verification key $V_K$; these communication devices act as Verifiers. A third-party communication device (e.g., belonging to security personnel) acts as a Receiver of a transaction.

The embodiment operates as follows.
1. An employee presents himself/herself to a testing facility which authenticates the identity of the employee and administers a test. The testing facility transmits the test results and the confirmation of the user's identity to the employee's enterprise user communication device. Optionally, a secure communication channel may be used for this purpose.
2. The employee user communication device receives the user identifier information and the test results and inputs them, along with the appropriate computer programs (CPs) or algorithms that processes them, to the PGE. The PGE in turn generates a composite data object or token and the associated proofs. As discussed above, the composite data object may include the individual data objects with their associated proofs as well as the proof for the composite data object itself. In this way the composite data object links the test result and the user identity information. The employee user communication device is now ready to act as Sender.
3. The Sender transmits the composite data object to a third-party communication device acting as the Receiver, which requests a Verifier to verify the composite data object in the manner described above.
4. The Receiver receives a verification notification from Verifier and acts according to its pre-determined logic (which may be incorporated, for example, in an app or the like provided by the enterprise and which receives the composite data object from the sender). For instance, the Receiver may present a visual and/or audible indicator indicating that the user's test results are positive or negative, which may be used to allow (in the case of a negative test result) or deny (in the case of a positive test result) the user entry to ACME's premises. In addition to or instead of a visual and/or audible indicator, the Receiver may communicate a signal (e.g., a near-field communication (NFC) signal) to a lock that automatically opens an entryway to the premises if the test results are negative. Of course, in alternative implementations the Receiver may take a wide variety of actions in response to the verification notification.

Example(s) Arising from Embodiment B:

An enterprise, say ACME, is interested in ensuring that its employees are tested for some personal characteristic such as whether they have or had a disease or infection. In this example ACME may only allow an employee to report for work if their tests are negative, e.g., only non-infected employees are allowed entry to the enterprise premises.

Enterprise ACME implements the engines KGE and PVE (with verifying key $V_K$) on a first collection of communication devices. These communication devices act as Receivers and Verifiers of transactions. ACME provisions the user communication devices of its employees with the proving keys $P_K$; these user communication devices implement the PGE and play the role of Sender in a transaction.

The embodiment operates as follows.
1. An employee presents himself/herself to a testing facility which authenticates the identity of the employee and administers a test. The testing facility transmits the test results and confirmation of the user's identity to the employee's user communication device. Optionally, a secure communication channel may be used for this purpose.
2. The employee user communication device receives the user identifier information and the test results and inputs them to the PGE, along with the appropriate computer programs (CPs) or algorithms that processes them. The PGE in turn generates a composite data object or token and the associated proofs. As discussed above, the composite data object may include the individual data objects with their associated proofs as well as the proof for the composite data object itself. In this way the composite data object links the test result and the user identity information. The employee user communication device is now ready to act as Sender.
3. The Sender transmits the composite data object to a Receiver who verifies the received composite data object.
4. The Receiver receives a verification notification from Verifier and acts according to its pre-determined logic (which may be incorporated, for example, in an app or the like provided by the enterprise and which also implements the PGE). For instance, the Receiver may present a visual and/or audible indicator indicating that the user's test results are positive or negative, which may be used to allow (in the case of a negative test result) or deny (in the case of a positive test result) the user entry to ACME's premises. In addition to or instead of a visual and/or audible indicator, the Receiver may communicate a signal (e.g., a near-field communication (NFC) signal) to a lock that automatically opens an entryway to the premises if the test results are negative. Of course, in alternative implementations the Receiver may take a wide variety of actions in response to the verification notification.

Example(s) Arising from Embodiment C:

An enterprise, say ACME, is interested in ensuring that its employees are tested for some personal characteristic such as whether they have or had a disease or infection. In this example ACME may only allow an employee to report for work if their tests are negative, e.g., only non-infected employees are allowed entry to the enterprise premises.

Enterprise ACME implements the engine KGE on its communication device(s). ACME provisions user communication devices of its employees with the proving and Verifying keys $P_K$ and $V_k$. These user communication devices act as the Sender, Verifier and Receiver in transactions.

The embodiment operates as follows.
1. An employee presents himself/herself to a testing facility which authenticates the identity of the employee and administers a test. The testing facility transmits the test results and confirmation of the user's identity to the employee's user communication device. Optionally, a secure communication channel may be used for this purpose.
2. The employee user communication device receives the user identifier information and the test results and inputs them to the PGE, along with the appropriate computer programs (CPs) or algorithms that processes them. The PGE in turn generates a composite data object or token and the associated proofs. As discussed above, the composite data object may include the individual data objects with their associated proofs as well as the proof for the composite data object itself. In this way the composite data object links the test result and the user identity information. The employee user communication device is now ready to act as Sender.

3. The Sender transmits the composite data object to the Receiver, which requests the Verifier to verify the composite data object.

The Receiver receives a verification notification from Verifier and acts according to its pre-determined logic (which may be incorporated, for example, in an app or the like provided by the enterprise and which also implements the PVE and the PGE). For instance, the Receiver may present a visual and/or audible indicator indicating that the user's test results are positive or negative, which may be used to allow (in the case of a negative test result) or deny (in the case of a positive test result) the user entry to ACME's premises. In addition to or instead of a visual and/or audible indicator, the Receiver may communicate a signal (e.g., a near-field communication (NFC) signal) to a lock that automatically opens an entryway to the premises if the test results are negative. Of course, in alternative implementations the Receiver may take a wide variety of actions in response to the verification notification.

In the examples discussed above in connection with Embodiments A, B and C the information that is incorporated in the data object is a personal characteristic of an employee, where the personal characteristic defines whether or not they have or had a disease or infection. More generally, the personal characteristic may be any permanent or temporary characteristic associated with an individual, including, without limitation, a physical trait (e.g., eye color, blood type, a current or past body temperature), a current or past location of the individual, or anything else that may be used to describe or distinguish some aspect of the individual, whether permanent or transient. Of course, as previously discussed, the data object may incorporate any type of information and not simply a personal characteristic such as discussed in these examples.

The computer program or algorithm that is input to the PGE processes underlying data such as test result data (as in the examples of Embodiments A, B and C above) or, in other examples discussed above, biometric data, other identity data, proof of age data, proof of residency data, and so on. Of course, more generally, this underlying data more generally may be any type of data, some of which represent personal characteristics of the user but others of which may represent a wide variety of other types of data such as the previously discussed spending rights. The information output from the PGE will include an assertion that is verified by the proof that is also output by the PGE. The proof verifies the assertion in the manner described above.

The nature of the assertion output by the PGE will depend on the nature of the underlying data from which it is generated. For instance, if the underlying data is a test result data, the assertion may be that the test results are positive or negative. However, the underlying test data is not itself revealed. If on the other hand the underlying data is biometric data, the assertion may verify that the user is known to the vender or provider of the computer program or algorithm and is who he purports to be. However, the actual biometric data itself is not revealed as part of the assertion. Likewise, if the underlying data is proof of age data (such as shown, for instance, in a state-issued driver's license) the assertion may be the user's actual age or an indication that is user is over a certain age (e.g., 18, 21 years of age). However, the actual driver's license data is not revealed.

The assertions themselves may take many forms. For instance, if the assertion is that test results are positive or negative, the assertion may be a cleartext statement or a visual or audio indicator of this result. Alternatively, or in addition thereto, the assertion may be reflected in an action that is taken such as the communication of a signal that automatically allows entry to a premises.

As used herein the terms "software," computer programs," "programs," "computer code" and the like refer to a set of program instructions running on an arithmetical processing device such as a microprocessor or DSP chip, or as a set of logic operations implemented in circuitry such as a field-programmable gate array (FPGA) or in a semicustom or custom VLSI integrated circuit. That is, all such references to "software," computer programs," "programs," "computer code," as well as references to various "engines" and the like may be implemented in any form of logic embodied in hardware, a combination of hardware and software, software, or software in execution. Furthermore, logic embodied, for instance, exclusively in hardware may also be arranged in some embodiments to function as its own trusted execution environment.

Illustrative Computing Environment

As discussed above, aspects of the subject matter described herein may be described in the general context of computer-executable instructions, such as program modules, being executed by a computer. Generally, program modules include routines, programs, objects, components, data structures, and so forth, which perform particular tasks or implement particular abstract data types. Aspects of the subject matter described herein may also be practiced in distributed computing environments where tasks are performed by remote processing devices that are linked through a communications network. In a distributed computing environment, program modules may be located in both local and remote computer storage media including memory storage devices.

Also, it is noted that some embodiments have been described as a process which is depicted as a flow diagram or block diagram. Although each may describe the operations as a sequential process, many of the operations can be performed in parallel or concurrently. In addition, the order of the operations may be rearranged. A process may have additional steps not included in the figure.

The claimed subject matter may be implemented as a method, apparatus, or article of manufacture using standard programming and/or engineering techniques to produce software, firmware, hardware, or any combination thereof to control a computer to implement the disclosed subject matter. For instance, the claimed subject matter may be implemented as a computer-readable storage medium embedded with a computer executable program, which encompasses a computer program accessible from any computer-readable storage device or storage media. For example, computer readable storage media can include but are not limited to magnetic storage devices (e.g., hard disk, floppy disk, magnetic strips . . . ), optical disks (e.g., compact disk (CD), digital versatile disk (DVD) . . . ), smart cards, and flash memory devices (e.g., card, stick, key drive . . . ). However, computer readable storage media do not include transitory forms of storage such as propagating signals, for example. Of course, those skilled in the art will recognize many modifications may be made to this configuration without departing from the scope or spirit of the claimed subject matter.

Moreover, as used in this application, the terms "component," "module," "engine," "system," "apparatus," "interface," or the like are generally intended to refer to a computer-related entity, either hardware, a combination of hardware and software, software, or software in execution.

For example, a component may be, but is not limited to being, a process running on a processor, a processor, an object, an executable, a thread of execution, a program, and/or a computer. By way of illustration, both an application running on a controller and the controller can be a component. One or more components may reside within a process and/or thread of execution and a component may be localized on one computer and/or distributed between two or more computers.

The foregoing described embodiments depict different components contained within, or connected with, different other components. It is to be understood that such depicted architectures are merely exemplary, and that in fact many other architectures can be implemented which achieve the same functionality. In a conceptual sense, any arrangement of components to achieve the same functionality is effectively "associated" such that the desired functionality is achieved. Hence, any two components herein combined to achieve a particular functionality can be seen as "associated with" each other such that the desired functionality is achieved, irrespective of architectures or intermediary components. Likewise, any two components so associated can also be viewed as being "operably connected", or "operably coupled", to each other to achieve the desired functionality.

The invention claimed is:

1. A method for communicating information relating to test results of a user, comprising:
   obtaining test results of a user;
   deriving an assertion from the test results of the user, the test results being input to a pre-provisioned first algorithm, the assertion being encapsulated in a first data object by a proof generating engine (PGE) that controls an environment in which the first algorithm is executed;
   generating a first proof configured to be usable to verify that the first algorithm used the test results to produce the assertion when provided to a proof verifying engine (PVE) along with the first data object, the test results itself being excluded from the first proof and the first data object such that privacy of the test results is maintained, wherein the first proof is generated by the PGE using as inputs the first algorithm and a first cryptographic key that is derived from the first algorithm using a key generating engine (KGE); and
   communicating the first proof and the first data object to a receiving communication device from an enterprise communication device associated with the user and an enterprise.

2. The method of claim 1, wherein the assertion links user identity information with the test results and indicates whether the user has tested positive or negative for a condition.

3. The method of claim 2, wherein the condition is a disease or infection.

4. The method of claim 1, wherein the obtaining, deriving, generating and communicating is performed by the enterprise communication device.

5. The method of claim 1, wherein the communicating includes sending the first proof and the first data object to the receiving communication device over a communications network, wherein the receiving communications device is associated with the enterprise.

6. The method of claim 1, wherein the environment in which the first algorithm is executed is provided by the PGE.

7. The method of claim 1, wherein the first cryptographic key is provided to the enterprise communication device by the enterprise.

8. The method of claim 1, wherein the first proof is configured to be usable to verify that the first algorithm used the underlying data to produce the assertion when provided to a PVE along with the first data object and a second cryptographic key that is complementary to the first cryptographic key and derived from the first algorithm using the KGE.

9. The method of claim 8, wherein the pre-provisioned first algorithm, the first and second cryptographic keys, the PGE and the PVE are provided by the enterprise.

10. The method of claim 9, wherein the PVE is implemented on the receiving communication device such that verification that the first algorithm used the underlying data to produce the assertion is able to be performed by the receiving communication device.

11. The method of claim 1, wherein communicating the first proof and the first data object to the receiving communication device includes causing a visual and/or audio indicator to be presented by the receiving communication device upon verification of the first data object, the visual and/or audio indicator indicating whether the user has tested positive or negative for a condition.

12. A method for communicating information relating to test results of a user, comprising:
    obtaining test results of a user;
    deriving an assertion from the test results of the user, the test results being input to a pre-provisioned first algorithm, the assertion being encapsulated in a first data object by a PGE that controls an environment in which the first algorithm is executed;
    generating a first proof configured to be usable to verify that the first algorithm used the test results to produce the assertion when provided to a PVE along with the first data object, the test results itself being excluded from the first proof and the first data object such that privacy of the test results is maintained, wherein the first proof is generated by a proof generating engine (PGE) using as inputs the first algorithm and a first cryptographic key that is derived from the first algorithm using a key generating engine (KGE); and
    verifying that the first algorithm used the test results to produce the assertion by providing the first proof and the first data object to the PVE; and
    in response to the verifying, presenting an indicator indicating whether the user has tested positive or negative for a condition.

13. The method of claim 12, wherein the indicator permits access to information and/or a premises associated with the enterprise.

14. The method of claim 12, wherein the assertion links user identity information with the test results and indicates whether the user has tested positive or negative for a condition.

15. The method of claim 14, wherein the condition is a disease or infection.

16. The method of claim 12, wherein the obtaining, deriving, generating and communicating is performed by the enterprise communication device.

17. The method of claim 12, wherein the communicating includes sending the first proof and the first data object to the receiving communication device over a communications network, wherein the receiving communications device is associated with the enterprise.

18. The method of claim 12, wherein the environment in which the first algorithm is executed is provided by the PGE.

19. The method of claim 17, wherein the first cryptographic key is provided to the enterprise communication device by the enterprise.

20. The method of claim 18, wherein the first proof is configured to be usable to verify that the first algorithm used the underlying data to produce the assertion when provided to a PVE along with the first data object and a second cryptographic key that is complementary to the first cryptographic key and derived from the first algorithm using the KGE.

21. The method of claim 20, wherein the pre-provisioned first algorithm, the first and second cryptographic keys, the PGE and the PVE are provided by the enterprise.

* * * * *